United States Patent
Stemmer et al.

(10) Patent No.: US 11,161,902 B2
(45) Date of Patent: Nov. 2, 2021

(54) TISSUE-SPECIFIC EXOSOMES AS BIOMARKERS

(71) Applicant: HELMHOLTZ ZENTRUM MÜNCHEN—DEUTSCHES FORSCHUNGSZENTRUM FÜR GESUNDHEIT UND UMWELT (GMBH), Neuherberg (DE)

(72) Inventors: Kerstin Stemmer, Munich (DE); Matthias Tschöp, Munich (DE); Michaela Bauer, Landshut (DE); Reinhard Zeidler, Olching (DE); Regina Feederle, Munich (DE)

(73) Assignee: Helmholtz Zentrum Muenchen—Deutsches Forschungszentrum Fuer Gesundheit Und Umwelt (GmbH), Neuherberg (DE)

( * ) Notice: Subject to any disclaimer, the term of this patent is extended or adjusted under 35 U.S.C. 154(b) by 449 days.

(21) Appl. No.: 16/300,019

(22) PCT Filed: May 9, 2017

(86) PCT No.: PCT/EP2017/060989
§ 371 (c)(1),
(2) Date: Nov. 8, 2018

(87) PCT Pub. No.: WO2017/194499
PCT Pub. Date: Nov. 16, 2017

(65) Prior Publication Data
US 2019/0391163 A1    Dec. 26, 2019

(30) Foreign Application Priority Data
May 9, 2016 (LU) .......................................... 93058

(51) Int. Cl.
*C07K 16/28* (2006.01)
*G01N 33/68* (2006.01)

(52) U.S. Cl.
CPC .......... *C07K 16/28* (2013.01); *G01N 33/6893* (2013.01); *G01N 2800/04* (2013.01); *G01N 2800/042* (2013.01); *G01N 2800/044* (2013.01)

(58) Field of Classification Search
CPC ................................ C07K 16/18; C07K 16/28
See application file for complete search history.

(56) References Cited

U.S. PATENT DOCUMENTS

| | | | |
|---|---|---|---|
| 2014/0141986 A1* | 5/2014 | Spetzler ................. | G01N 33/50 506/9 |
| 2015/0330997 A1* | 11/2015 | Paramithiotis ...... | G01N 33/6893 506/9 |
| 2016/0220613 A1* | 8/2016 | Lim ........................ | A61P 37/06 |
| 2018/0066307 A1* | 3/2018 | Ter-Ovanesyan .... | A61K 9/5176 |

FOREIGN PATENT DOCUMENTS

| | | |
|---|---|---|
| WO | 2008129124 A1 | 10/2008 |
| WO | 2012048372 A1 | 4/2012 |
| WO | 2015082839 A1 | 6/2015 |
| WO | 2016201220 A1 | 12/2016 |

OTHER PUBLICATIONS

Connolly et al. "Characterisation of adipocyte-derived extracellular vesicles released pre- and post-adipogenesis" J Extracell Vesicles. Nov. 24, 2015;4:29159. doi: 10.3402/jev.v4.29159 (Year: 2015).*
Raposo, G., et al. (1996) "B lymphocytes secrete antigen-presenting vesicles", J. Exp. Med. 183:1161-1172.
Escola, J.M., et al. (1998) "Selective Enrichment of Tetraspan Proteins on the Internal Vesicles of Multivesicular Endosomes and on Exosomes Secreted by Human B-lymphocytes", J. Biol.Chem., 273:20121-20127.
Cheruvanky, A., et al. (2007) "Rapid isolation of urinary exosomal biomarkers using a nanomembrane ultrafiltration concentrator", Am. J .Physiol. Renal Physiol., 292:F1657-61.
Barrès, C., et al. (2010) "Galectin-5 is bound onto the surface of rat retiulocyte exosomes and modulates vesicle uptake by macrophages", Blood, 115:696-705.
Chen, C., et al. (2010) "Microfluidic isolation and transcriptome analysis of serum microvesicles", Lab Chip, 10: 505-11.
Dean, C.B., et al. (2007) "Generalized linear mixed models: a review and some extensions," Lifetime Data Anal., 13:497-512.
Hoshino, A., et al. (2015) "Tumour exosome integrins determine organotropic metastasis", Nature 527:329-335.
Thery, C., et al. (2006) "Isolation and characterization of exosomes from cell culture supernatants and biological fluids", Curr Protec Cell Biol Chapter 3, Unit 3.22.1, 29 pages.
Muller, G., et al. (2009) "Induced release of membrane vesicles from rat adipocytes containing glycosylphosphatidylinositol-anchored microdomain and lipid droplet signalling proteins", Cell Signal, 21:324-338.
Kanneganti, T.D., et al. (2012) "Immunological complications of obesity", Nat. Immunol., 13:707-712.
De Gassart, A., et al. (2003) "Lipid raft-associated protein sorting in exosomes", Blood, 102:4336-4344.
Ratajczak, J., et al. (2006) "Embryonic stem cell-derived microvesicles reprogram hematopoietic progenitors: evidence for horizontal transfer of mRNA and protein delivery", Leukemia, 20:847-856.
Ebert, M.S., et al. (2012) "Roles for microRNAs in conferring robustness to biological processes", Cell, 149:515-524.

(Continued)

*Primary Examiner* — Christine Foster
(74) *Attorney, Agent, or Firm* — Kagan Binder, PLLC

(57) ABSTRACT

In general, the present invention relates to the field of (bio-)medicine and in particular to various metabolic diseases. Specifically, the invention provides means and methods for diagnosing, monitoring and predicting the risk for developing metabolic diseases. The invention uses exosomes as biomarkers for the aforementioned purposes. Moreover, an antibody of the present invention capable of specifically recognizing tissue-specific exosomes is also provided.

6 Claims, 39 Drawing Sheets
Specification includes a Sequence Listing.

(56) References Cited

OTHER PUBLICATIONS

Ceppo, F., et al. (2014) "Implication of the Tpl2 kinase in inflammatory changes and insulin resistance induced by the interaction between adipocytes and macrophages", Endocrinology, 155:951-964.

Perfield II, J.W., et al. (2011) "Tumor progression locus 2 (TPL2) regulates obesity-associated inflammation and insulin resistance", Diabetes, 60:1168-1176.

Arkan, M.C., et al., (2005) "IKK-beta links inflammation to obesity-induced insulin resistance", Nat. Med., 11:191-198.

Lehr, S., et al. (2012) "Adipokines: a treasure trove for the discovery of biomarkers for metabolic disorders", Proteomics Clin. Appl., 6:91-101.

Bobrie, A., et al. (2011) "Exosome secretion: molecular mechanisms and roles in immune responses", Traffic, 12:1659-1668.

Rainer, J., et al. (2006) "CARMAweb: comprehensive R- and bioconductor-based web service for microarray data analysis", Nucleic Acids Res., 34: W498-503.

Muller, G., et al. (2009) "Induced translocation of glycosylphosphatidylinositol-anchored proteins from lipid droplets to adiposomes in rat adipocytes", Br. J. Pharmacol., 158:749-770.

Weisberg, S.P. et al., (2003) "Obesity is associated with macrophage accumulation in adipose tissue", J. Clin. Invest., 112:1796-1808.

Sun, D., et al. (2010) "A novel nanoparticle drug delivery system: the anti-inflammatory activity of curcumin is enhanced when encapsulated in exosomes", Mol.Ther., 18:1606-1614.

Takahashi, Y., et al. (2013) "Visualization and in vivo tracking of the exosomes of murine melanoma B16-BL6 cells in mice after intravenous injection", J. Biotechnol., 165: 77-84.

Ouchi, N., et al. (2011) "Adipokines in inflammation and metabolic disease", Nat. Rev. Immunol., 11:85-97.

Dumitru, C.D., et al. (2000) "TNF-alpha induction by LPS is regulated posttranscriptionally via a Tpl2/ERK-dependent pathway", Cell, 103:1071-1083.

Partecke, L.I., et al. (2011) "A syngeneic orthotopic murine model of pancreatic adenocarcinoma in the C57/BL6 mouse using the Panc02 and 6606PDA cell lines", Eur. Surg. Res., 47:98-107.

Wisniewski, J.R., et al. (2009) "Universal sample preparation method for proteome analysis", Nat. Methods, 6:359-362.

Grosche, A., et al. (2015) "The proteome of native adult Muller glial cells from murine retina", Mol. Cell Proteomics, 61 pages.

Hauck, S.M., et al. (2010) "Deciphering membrane-associated molecular processes in target tissue of autoimmune uveitis by label-free quantitative mass spectrometry", Mol. Cell Proteomics, 9:2292-2305.

Merl, J., et al. (2012) "Direct comparison of MS-based label-free and SILAC quantitative proteome profiling strategies in primary retinal Muller cells", Proteomics, 12:1902-1911.

Barapatre, N. et al., (2015) "Quantitative detection of drug dose and spatial distribution in the lung revealed by Cryoslicing Imaging", J. Pharm. Biomed. Anal., 102:129-136.

Pfaffl, M.W. (2001) "A new mathematical model for relative quantification in real-time RT-PCR", Nucleic Acids Res., 29:2002-2007.

Aoki et al. (2007) "Identification and Characterization of Microvesicles Secreted by 3T3-LI Adipocytes: Redox- and Hormone Dependent Induction of Milk Fat Globule-Epidermal Growth Factor 8-Associated Microvesicles", Endocrinology 148:3850-3862.

Ferrante, S.C., et al. (2015) "Adipocyte-derived exosomal miRNAs: a novel mechanism for obesity-related disease", Pediatric Research 77:447-454.

Kranendonk, M.E.G., et al. (2014) "Extracellular vesicle markers in relation to obesity and metabolic complications in patients with manifest cardiovascular disease", Cardiovascular Diabetology 13:1-11.

Chen, Y., et al. (2016) "Exosomal microRNA miR-92a concentration in serum reflects human brown fat activity", Nature Communication 7:1-9.

Deng, Z-b., et al. (2009) "Adipose Tissue Exosome-Like Vesicles Mediate Activation of Macrophage-Induced Insulin Resistance", Diabetes, 58:2498-2505.

Koeck, E.S., et al. (2014) "Adipocyte exosomes induce transforming growth factor beta pathway dysregulation in hepatocytes: a novel paradigm for obesity-related liver disease", Journal of Surgical Research, 192:268-275.

"GeneChip Human Genome U 133 Arrays" (2003) Affymetrix Datasheet, pp. 1-8.

"Agilent SurePrint G3 Human Catalog CGH Microarrays" (2009) Agilent Technologies, pp. 1-8.

Souto, et al. (2003) "Immunopurification and Characterization of Rat Adipocyte Caveolae Suggest Their Dissociation from Insulin Signaling", The Journal of Biological Chemistry, 278: 18321-18329.

Pasarica, M., et al. (2009) "Adipose Tissue Collagen VI in Obesity", J. Clin. Endocrinol Metab. 94: 5155-5162.

Skogberg, G., et al. (2015) "Human thymic epithelial primary cells produce exosomes carrying tissue-restricted antigens," Immunology and Cell Biology, 93:727-734.

Gusachenko, O.N., et al. (2013) "Nucleic Acids in Exosomes: Disease Markers and Intercellular Communication Molecules", Biochemistry, 78:1-7.

Mizutani, K., et al. (2014) "Isolation of Prostate Cancer-related Exosomes", Anticancer Research 34:3419-3424.

\* cited by examiner

A-1

A-2

A-3

A-4

A-5

E-1

E-2

A

B

C

D

H

Tissue: DIO vs lean

Exosomes DIO vs lean

| miRNA Species | Fold change | P-value | BH adj.p-value | Targets | Functions |
|---|---|---|---|---|---|
| mmu-miR-101a-3p | -1,6715 | 7,3E-05 | 0,01368054 | PTGS2 TGFβ1 TGFβR1 | Cox-2 regulation Inhibition of apoptosis |
| mmu-miR-143-3p | -1,6183 | 0,00021 | 0,01368054 | KRAS HK2 ORP8 | Apoptosis Glycolysis Cholesterol metab |
| mmu-miR-222-3p | 4,09468 | 0,00025 | 0,01368054 | PTEN TIMP3 | Fibrosis Inflammation |
| mmu-miR-150-5p | -2,4025 | 0,00028 | 0,01368054 | CEBPβ PRDM16 PGC1α | Browning |
| mmu-miR-345-5p | -2,5334 | 0,00033 | 0,01368054 | ??? | ??? |
| mmu-miR-27b-3p | 1,6139 | 0,00056 | 0,018270556 | PPARγ PRDM16 LPL CD36 | Browning Adipocyte differentiation Cholesterol handling |
| mmu-miR-139-3p | 5,65576 | 0,00066 | 0,018270556 | no target | ??? |
| mmu-miR-181a-5p | -1,6744 | 0,00071 | 0,018270556 | no target | Inflammation associated with obesity |
| mmu-miR-322-5p | -1,7413 | 0,00089 | 0,018911082 | BCL2 | apoptosis |
| mmu-miR-142-3p | 2,43017 | 0,00091 | 0,018911082 | TGFβR1 | Macrophage diff/polarization |
| mmu-miR-126a-3p | -1,7111 | 0,00139 | 0,026208655 | ??? | T2D Biomarker, down |
| mmu-miR-24-3p | 1,57565 | 0,00156 | 0,026889647 | Bax | Alzheimer biomarker Tumor proliferation |
| mmu-miR-376a-3p | 3,37427 | 0,00286 | 0,044009108 | Grp78? | ??? |
| mmu-miR-342-3p | 4,35548 | 0,00321 | 0,044009108 | CtBP2 | Adipogenesis |
| mmu-miR-425-5p | -1,4712 | 0,00336 | 0,044009108 | ??? | ??? |
| mmu-miR-146b-5p | 1,7666 | 0,00363 | 0,044009108 | Smad4 PDGFRα | regulates TGFβ signaling |
| mmu-miR-29b-3p | -1,4181 | 0,00379 | 0,044009108 | ??? Foxa2 | ??? Regulation of lipid metabolism |
| mmu-miR-18a-5p | 1,79243 | 0,00383 | 0,044009108 | ??? | ??? |
| mmu-miR-450a-5p | -2,6134 | 0,00447 | 0,048687198 | ??? | ??? |
| mmu-miR-26a-5p | -1,5945 | 0,00528 | 0,054651667 | ??? | represses TLR4 activation and inflammation in microglia |

Diff: differentiated adipocytes, undiff: undifferentiated adipocytes)

TISSUE-SPECIFIC EXOSOMES AS BIOMARKERS

CROSS-REFERENCE TO RELATED APPLICATIONS

The present Application claims priority to International Application No. PCT/EP2017/060989, filed May 9, 2017, and titled "TISSUE-SPECIFIC EXOSOMES AS BIOMARKERS," which claims priority to Luxembourg Application No. 93058, filed on May 9, 2016, which is incorporated herein by reference in its entirety. Also, the entire contents of the ASCII text file entitled "IPM0088US_Sequence_Listing.txt" created on Nov. 8, 2018, having a size of 23 kilobytes is incorporated herein by reference.

BACKGROUND

Obesity, a condition associated with excessive fat storage in the adipose tissue, has reached epidemic proportions worldwide and is a leading cause of preventable illness and death. Besides its role as main storage organ for triglycerides, adipose tissue has moreover been recognized as endocrine organ that secretes various humoral factors named adipokines. An imbalance of adipokine profiles in obese individuals has been linked to obesity-associated complications like diabetes type 2, atherosclerosis and certain types of cancer.

According to World Health Organization (WHO) projections, up to 57.8% of the world's adult population could be either overweight or obese by 2030. Hypercaloric overnutrition and a sedentary way of life in combination—as common in industrialized societies—can result in an excess energy intake leading to fat accumulation, and, eventually, metabolic dysfunction. These correlations make obesity and its related metabolic disorders a major health problem causing serious economic and social burdens.

The WHO defines obesity as 'a body mass index (BMI) greater than or equal to 30 kg/m$^2$'. However, while the BMI can easily be determined, it is unable to distinguish between differences in fat mass and muscle mass, factors which have opposite impacts on health. Various alternative or additional measures have been advocated to improve estimates of adiposity, including waist circumference (WC), waist-hip ratio (WHR), waist-height ratio, neck circumference, conicity index and body adiposity index, but do not fare much better. Importantly, the aforementioned measures only indicate obesity-associated pathological changes in the tissue, where excess fat has accumulated and potentially already induced deregulation of metabolic pathways.

There is thus a critical need in the art for means and methods that allow for easy, reliable, non- or minimally invasive (and thus risk-minimized) and efficient diagnosis or prediction of obesity and also other metabolic diseases such as metabolic syndrome, prediabetes, diabetes and associated co-morbidities that may or may not be associated with obesity.

Exosomes belong to extracellular vesicles (EVs) that carry functional proteins, lipids and RNA species. In general, EVs consist of exosomes, microvesicles (MVs) and apoptotic bodies. EVs provide a source for diagnostic analyses and are released by healthy and diseased cells into bodily fluids. They are considered as stable carriers of genetic material, proteins and lipids, which represent the physiological state of the secreting cell.

From the time when exosomes were first described in the 1970s by the group of Johnstone and Stahl, exosomes are a target of constant research. Initially considered as cellular waste disposal system, both exosomes and MVs are now recognized as important signaling molecules that help reprogram cellular function in a paracrine or endocrine fashion. Once secreted, the tissue distribution and uptake of EVs is less clear. Recent reports suggest that exosomes are directed towards specific target cells and tissues by distinct integrins. Such organotrophic specificity may explain why exosomes are linked to distinct pathological conditions such as tumor metastasis, immunological disorders and neurodegenerative diseases. With the capability of transferring proteins, lipids and nucleic acids to recipient cells, they have become a focus of research for different therapeutic applications, including treatment of autoimmune syndromes and neurodegenerative disorders such as Alzheimer's and Parkinson's disease, in addition to infectious diseases such as tuberculosis, diphtheria, and toxoplasmosis as well as infections caused by prions or viruses such as HIV. Moreover, exosomes have been recognized as a versatile tool for biomarker identification for early diagnosis of different types of cancer. However, the role of exosomes in etiology and pathogenesis of obesity, its sequelae and related metabolic diseases are yet to be understood.

Since at present, extracting EVs from a variety of samples has still major limitations due to a lack of technology that allows discriminating between EVs of different tissues, it is the object of the present invention to comply with the needs set out in the prior art and provide an improved strategy for extracting tissue specific EVs from a sample obtained from a subject to be diagnosed.

SUMMARY

The present invention provides an antibody-based strategy for extracting tissue-specific EVs, preferably isolatable by an antibody of the present invention, which is highly specific for said tissue-specific EVs.

Further, the invention is based on a two-fold finding: First, the present inventors established novel means and methods for isolating exosomes from bodily tissues and fluids, specifically from white adipose tissue and serum by isolating tissue-specific exosomes with an antibody of the present invention capable of specifically binding to a tissue-specific exosomal surface marker, and discovered that exosomes comprise a molecular cargo that is reminiscent of their origin. Second, the inventors demonstrated that molecular constituents of exosomes, particularly exosomal proteins and RNAs, reflect not only the source tissue, but also its metabolic state.

The present inventors demonstrated that exosomes are highly specific diagnostic biomarkers that are capable of conveying "real-time" information about cells and tissues involved in metabolic diseases; thereby enabling diagnosis or even prognosis of metabolic diseases before any symptoms occur. In particular, the present inventors discovered that the molecular cargo of adipocyte-derived exosomes reflects both body composition and environmental conditions such as diet. Tissue-specific exosomes thus hold particular potential as a "liquid biopsy" of healthy and diseased tissue that allows for non-invasive, early and highly specific detection of markers attributed to various metabolic diseases. Exosomes therefore hold great promise as novel biomarkers for clinical diagnosis of metabolic diseases.

We here hypothesize that increased adiposity leads to the release of exosomes from adipocytes that carry unique and disease relevant signaling moieties, thereby affecting selected target cells and organs in a paracrine and endocrine fashion. We further propose that adipocyte exosomes are biomarker for clinical diagnosis of adipose tissue function, which may preferably be isolatable by an antibody of the present invention being able to bind to an exosomal surface marker specific for said tissue-specific EVs.

In a first aspect, the present invention provides tissue-specific exosomes for use in a method of diagnosing, monitoring and/or predicting the risk for developing a metabolic disease in a subject, wherein said tissue-specific exosomes are isolatable by an antibody capable of specifically binding to a tissue-specific exosomal surface marker, wherein said antibody comprises a) the following $V_H$ and $V_L$ domain CDRs having the amino acid sequence shown in SEQ ID Nos. 1 to 3 and 4 to 6, b) the following $V_H$ and $V_L$ domain CDRs having the amino acid sequence shown in SEQ ID Nos. 7 to 9 and 10 to 12, c) the following $V_H$ and $V_L$ domain CDRs having the amino acid sequence shown in SEQ ID Nos. 13 to 15 and 16 to 18.

Monitoring in this respect may mean evaluating treatment efficacy and/or progression of the metabolic disease.

The tissue-specific exosomes may be derived from white adipose tissue.

Metabolic disease envisaged for diagnosis, montoring and/or prediction with the help of the tissue-specific exosomes described herein may include obesity, hyperglycaemia, insulin resistance, prediabetes, type 1 or type 2 diabetes, adipose tissue inflammation, adipose tissue browning, fatty liver disease (FLD), glycogen storage disease (GSD), galactosemia, lactose intolerance, fructose intolerance, sucrose intolerance, phenylketonuria (PKU), glutaric aciduria type 1, organic acidemia, lysosomal storage diseases, including lipid storage disorders, mucopolysaccharidoses, mucolipidoses, Systemic primary carnitine deficiency, (SPCD), haemochromatosis, and glycoproteinosis.

The tissue-specific exosomes may be isolated from a sample of the subject, which may be selected from a blood sample, a plasma sample, a serum sample, lymph, saliva, bile, feces, breast milk, urine sample, cerebrospinal fluid sample, amniotic fluid, or an organ or tissue biopsy.

Further, an exosomal biomarker may be detected that is indicative for the metabolic disease in question.

Additionally, the subject being diagnosed, monitored and/or predicted with the help of the tissue-specific exosomes described herein may be a mammal, in particular a human, non-human primate, dog, cat, guinea pig, rabbit, rat or mouse.

In a further aspect, the present invention provides for the use of a tissue-specific exosomal surface marker for isolation of exosomes from a sample of a subject, wherein said tissue-specific exosomes are isolatable by an antibody capable of specifically binding to a tissue-specific exosomal surface marker, wherein said antibody comprises a) the following $V_H$ and $V_L$ domain CDRs having the amino acid sequence shown in SEQ ID Nos. 1 to 3 and 4 to 6, b) the following $V_H$ and $V_L$ domain CDRs having the amino acid sequence shown in SEQ ID Nos. 7 to 9 and 10 to 12, c) the following $V_H$ and $V_L$ domain CDRs having the amino acid sequence shown in SEQ ID Nos. 13 to 15 and 16 to 18.

Moreover, the present invention relates to an antibody of the present invention capable of specifically binding to a tissue-specific exosomal surface marker, wherein (i) said antibody comprises a) the following $V_H$ and $V_L$ domain CDRs having the amino acid sequence shown in SEQ ID Nos. 1 to 3 and 4 to 6, b) the following $V_H$ and $V_L$ domain CDRs having the amino acid sequence shown in SEQ ID Nos. 7 to 9 and 10 to 12, c) the following $V_H$ and $V_L$ domain CDRs having the amino acid sequence shown in SEQ ID Nos. 13 to 15 and 16 to 18, or wherein (ii) said antibody competes for the same epitope as that recognized by the antibody of (i) and wherein the antibody can block the binding of the antibody of (i) by at least 20% compared with the affinity obtained in a control test performed in the absence of the competing antibody.

Further, the present invention relates to a kit comprising means for detecting the presence of a tissue-specific exosomal surface marker and optionally means for isolating tissue-specific exosomes from a sample of a subject, wherein said tissue-specific exosomes are isolatable by an antibody capable of specifically binding to a tissue-specific exosomal surface marker, wherein said antibody comprises a) the following $V_H$ and $V_L$ domain CDRs having the amino acid sequence shown in SEQ ID Nos. 1 to 3 and 4 to 6, b) the following $V_H$ and $V_L$ domain CDRs having the amino acid sequence shown in SEQ ID Nos. 7 to 9 and 10 to 12, c) the following $V_H$ and $V_L$ domain CDRs having the amino acid sequence shown in SEQ ID Nos. 13 to 15 and 16 to 18, and means for detecting the presence of at least one exosomal biomarker indicative for the metabolic state of a tissue, tissue health or disease.

The invention also relates to an in vitro method of diagnosing or monitoring a metabolic disease in a subject or predicting the risk of a subject of developing a metabolic disease, said method comprising the following steps: (i) isolating tissue-specific exosomes from a sample of the subject, wherein said tissue-specific exosomes are isolatable by an antibody capable of specifically binding to a tissue-specific exosomal surface marker, wherein said antibody comprises a) the following $V_H$ and $V_L$ domain CDRs having the amino acid sequence shown in SEQ ID Nos. 1 to 3 and 4 to 6, b) the following $V_H$ and $V_L$ domain CDRs having the amino acid sequence shown in SEQ ID Nos. 7 to 9 and 10 to 12, c) the following $V_H$ and $V_L$ domain CDRs having the amino acid sequence shown in SEQ ID Nos. 13 to 15 and 16 to 18, and (ii) determining the presence of at least one biomarker in said exosomes that is indicative for a metabolic disease and/or its co-morbidities or for the risk of developing a metabolic disease.

Also provided by the present invention is a method for isolating tissue-specific exosomes from a sample, said method comprising a step of contacting said sample with an antibody capable of specifically binding to a tissue-specific exosomal surface marker, wherein said antibody comprises a) the following $V_H$ and $V_L$ domain CDRs having the amino acid sequence shown in SEQ ID Nos. 1 to 3 and 4 to 6, b) the following $V_H$ and $V_L$ domain CDRs having the amino acid sequence shown in SEQ ID Nos. 7 to 9 and 10 to 12, c) the following $V_H$ and $V_L$ domain CDRs having the amino acid sequence shown in SEQ ID Nos. 13 to 15 and 16 to 18.

Moreover, the present invention relates to the use, the antibody of the present invention, the kit, the in vitro method and the method as mentioned above, wherein said tissue may be white adipose tissue.

Additionally, the present invention relates to the use of a tissue-specific exosomal surface marker, the kit, the in vitro method as mentioned above, wherein the subject may be a mammal, in particular a human, non-human primate, dog, cat, guinea pig, rabbit, rat or mouse.

Further, the present invention relates to the use of a tissue-specific exosomal surface marker, the antibody of the present invention, the kit, the in vitro method and the method as mentioned above, wherein said sample may be selected from a blood sample, a plasma sample, a serum sample, lymph, saliva, bile, feces, breast milk, urine sample, cerebrospinal fluid sample, amniotic fluid, or an organ or tissue biopsy.

(A) Schematic protocol for the isolation of exosomes from the adipocyte fraction of the epididymal (eWAT) and inguinal white adipose tissue (iWAT) or from serum. (B) Representative transmission electron microscopy of exosomes isolated from eWAT- or iWAT adipocytes or serum (scale bar: 200 nm). (C) Dot blots of eWAT adipocyte and serum exosome surface markers GM1, CD63, CD9 and CD81 (n=4 mice per group). (D) Exosomal secretion rates from eWAT and iWAT adipocytes of lean and DIO mice, as determined by exosomal protein per tissue weight per hour (eWAT n=9 per group, iWAT n=5 for lean and n=10 for obese). Dot blots of exosomes derived from eWAT (upper panels) and iWAT (lower panels) of lean and DIO mice (eWAT=9 per group, iWAT=10 per group) and corresponding signal intensities of GM1 (E, F) and CD63 (G, H). Cd63 mRNA expression of eWAT (I) and iWAT (J) from lean (n=7) and obese (n=8) mice. Statistical significance was analyzed using One-Way ANOVA followed by Sidak's multiple comparisons test (D, F, H), or two-tailed student's t-test (I, J).

Figure 2:
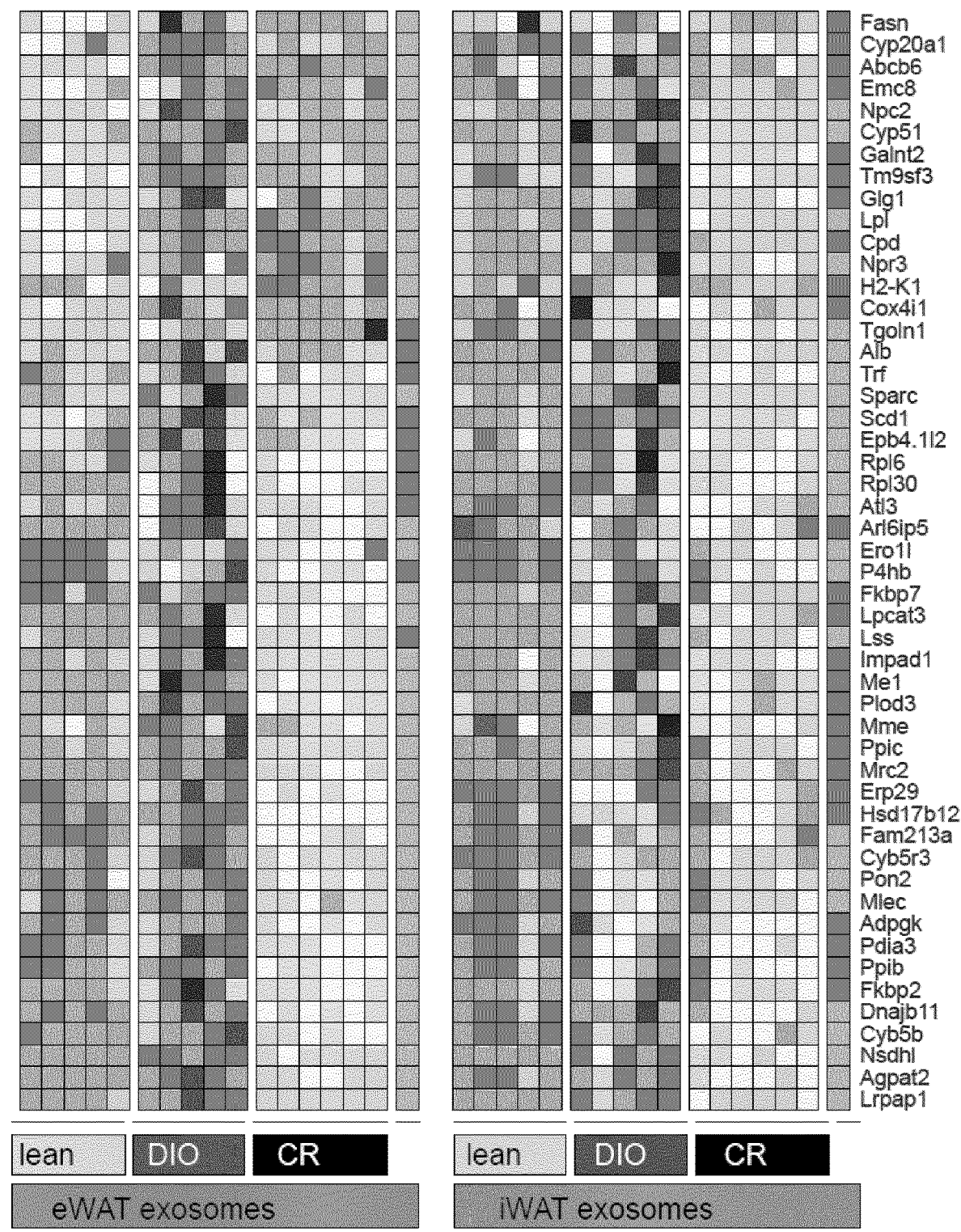
Figure 2:
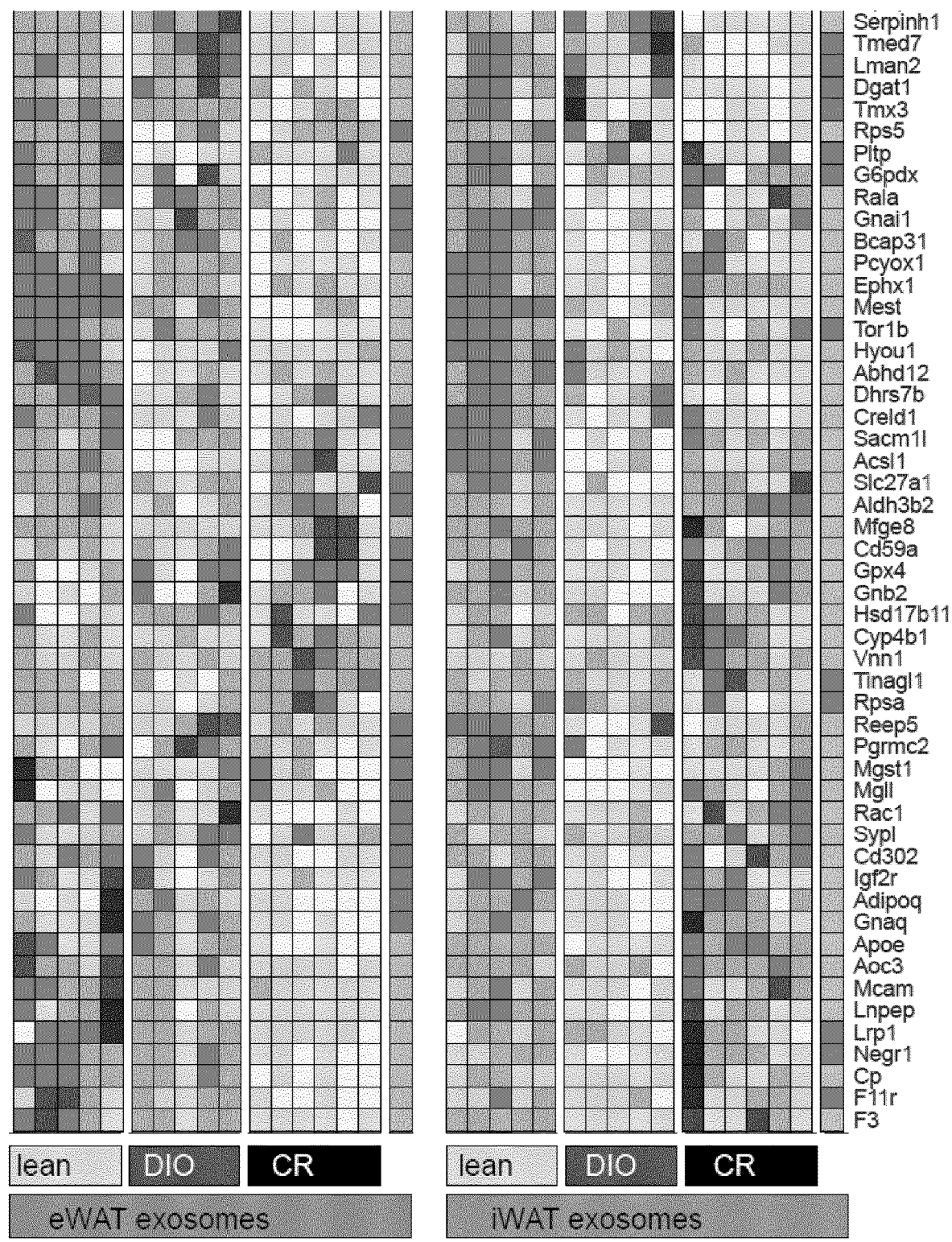
Figure 2:
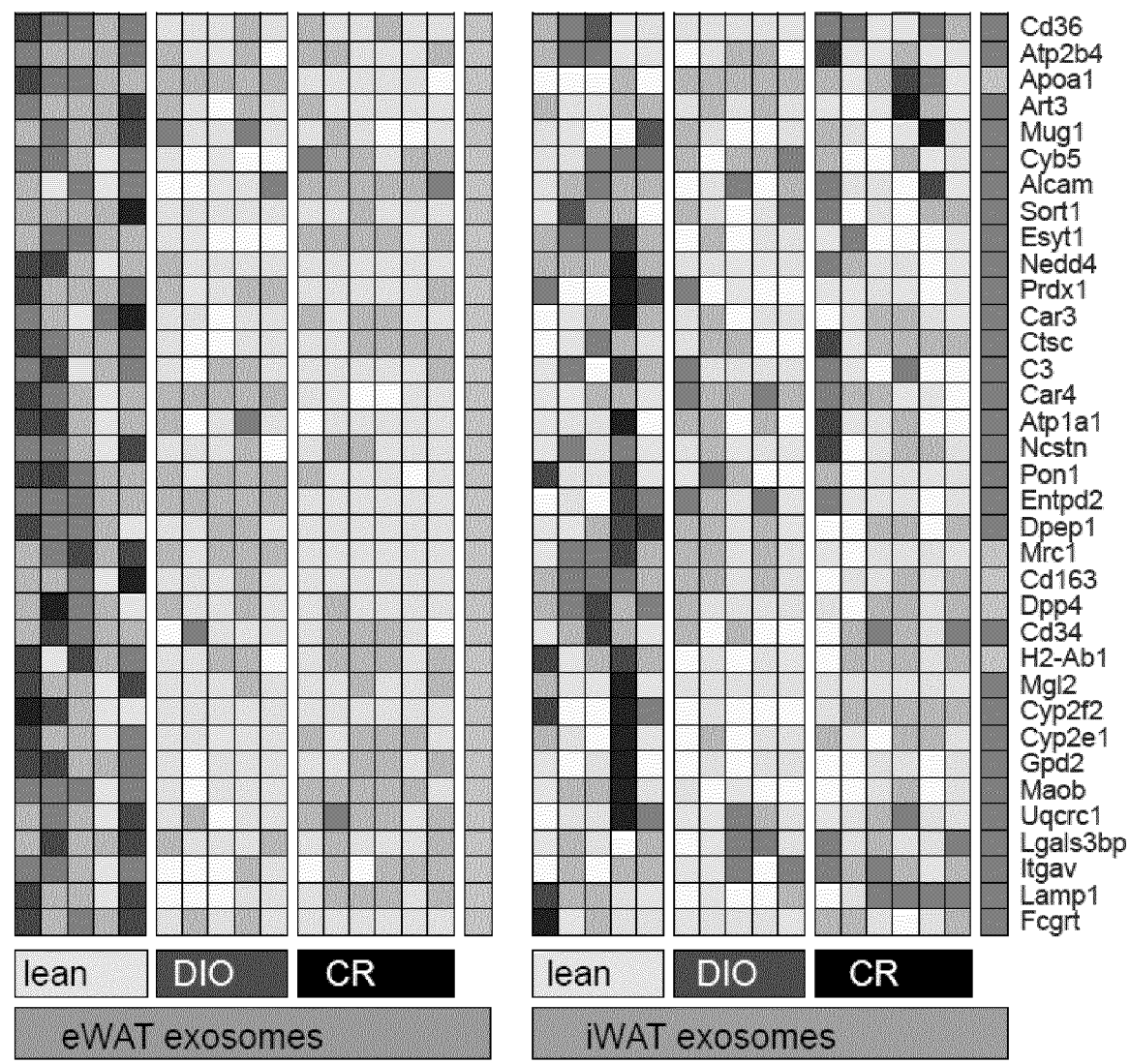
Figure 2:
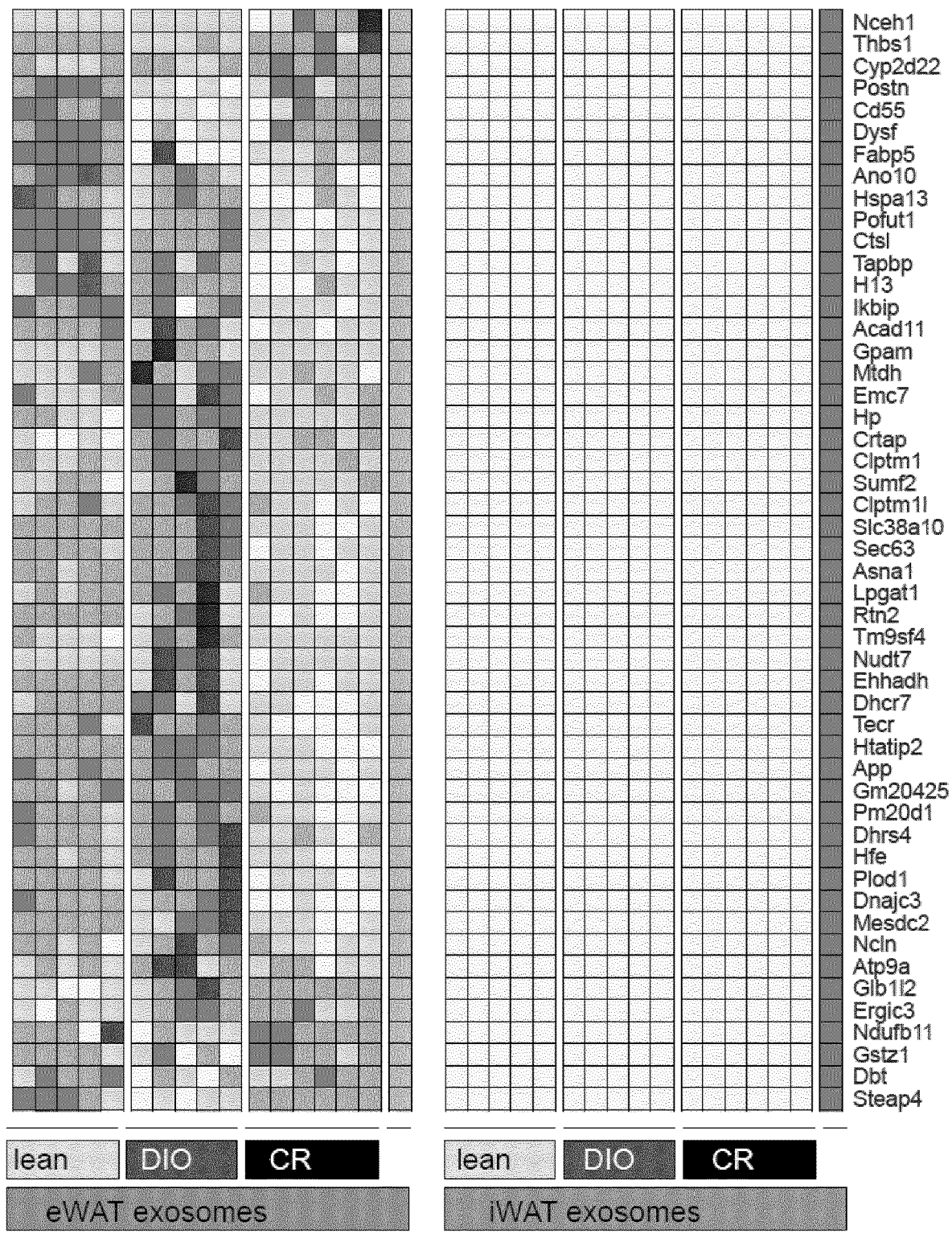
Figure 2:
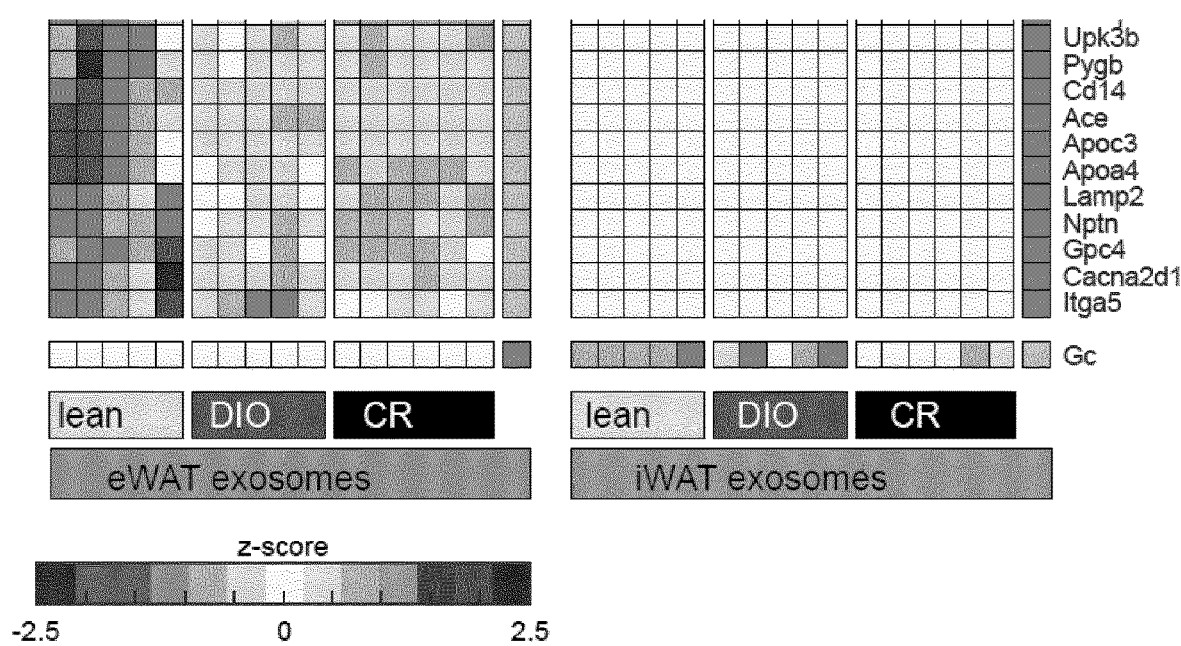
Figure 2:
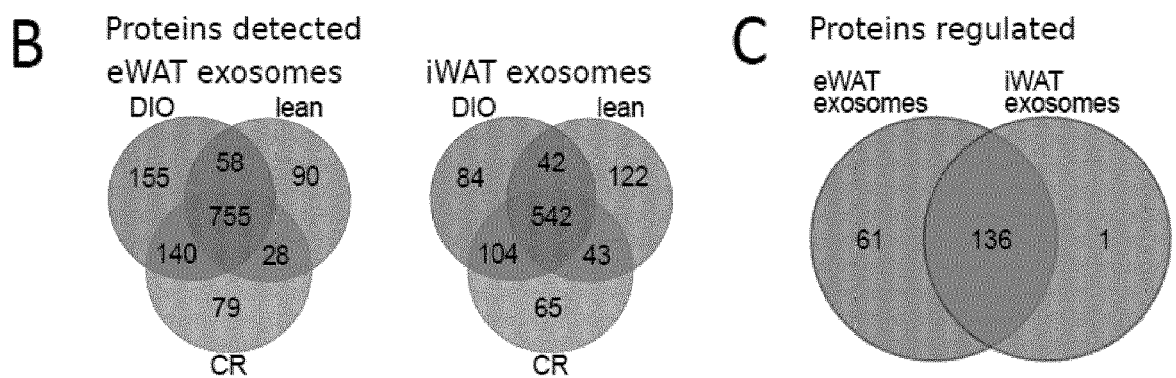
Figure 2:
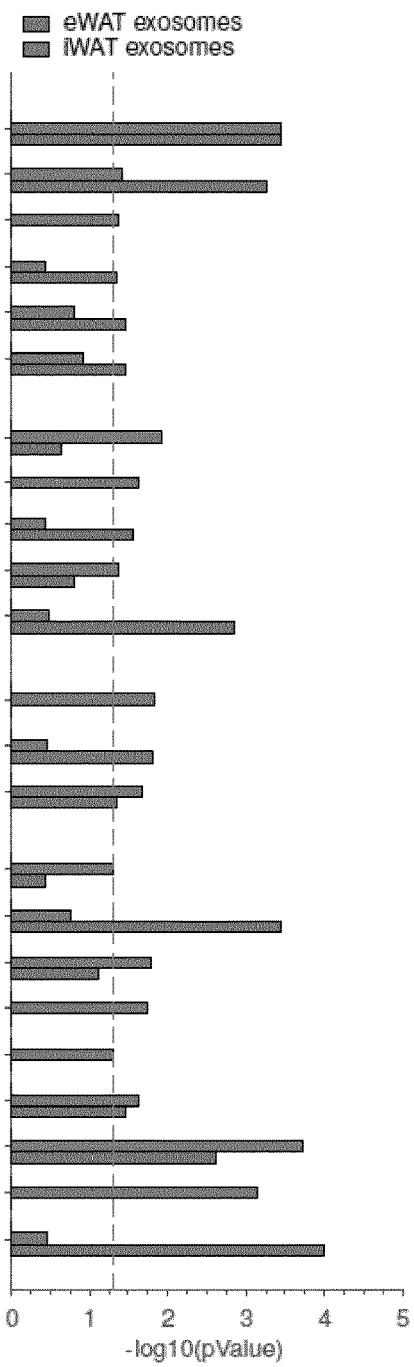
Figure 2:
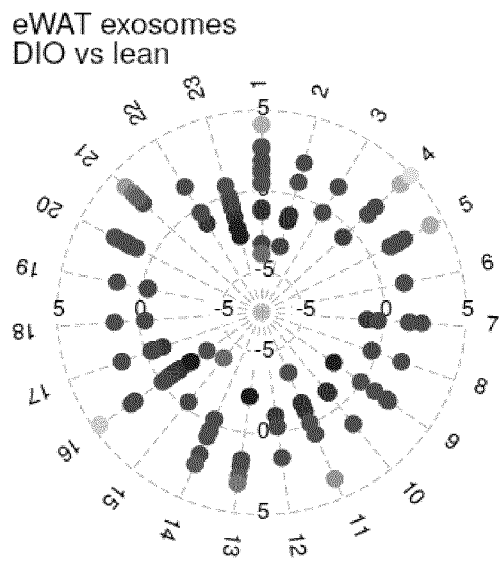
Figure 2:
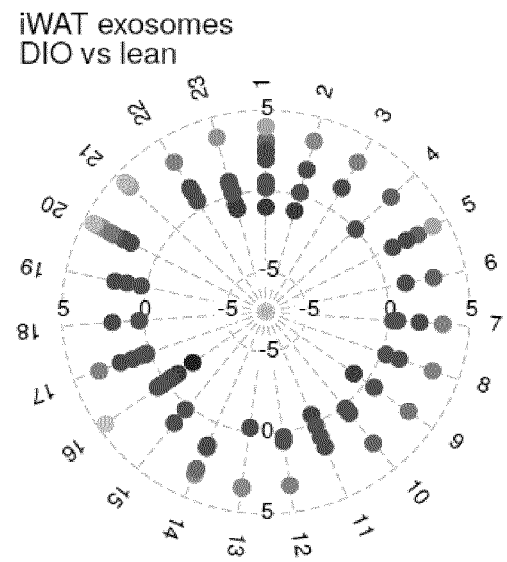
Figure 2:
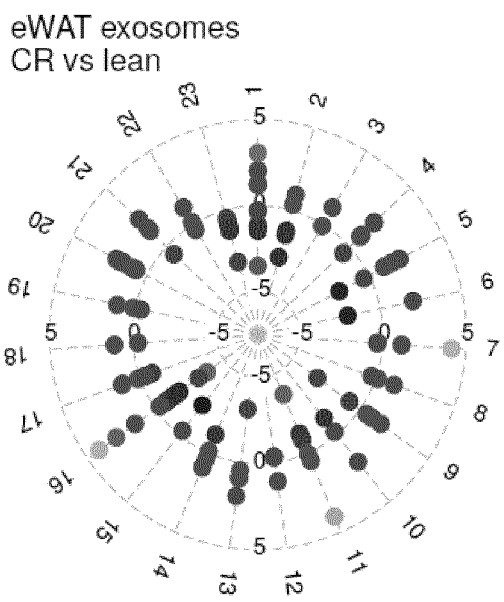
Figure 2:
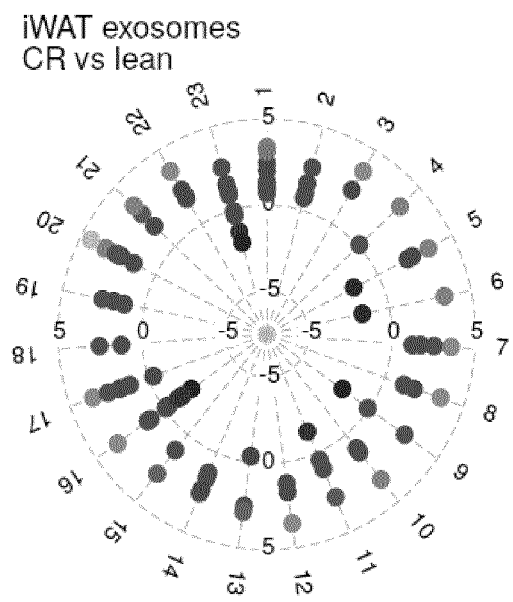
Figure 2:
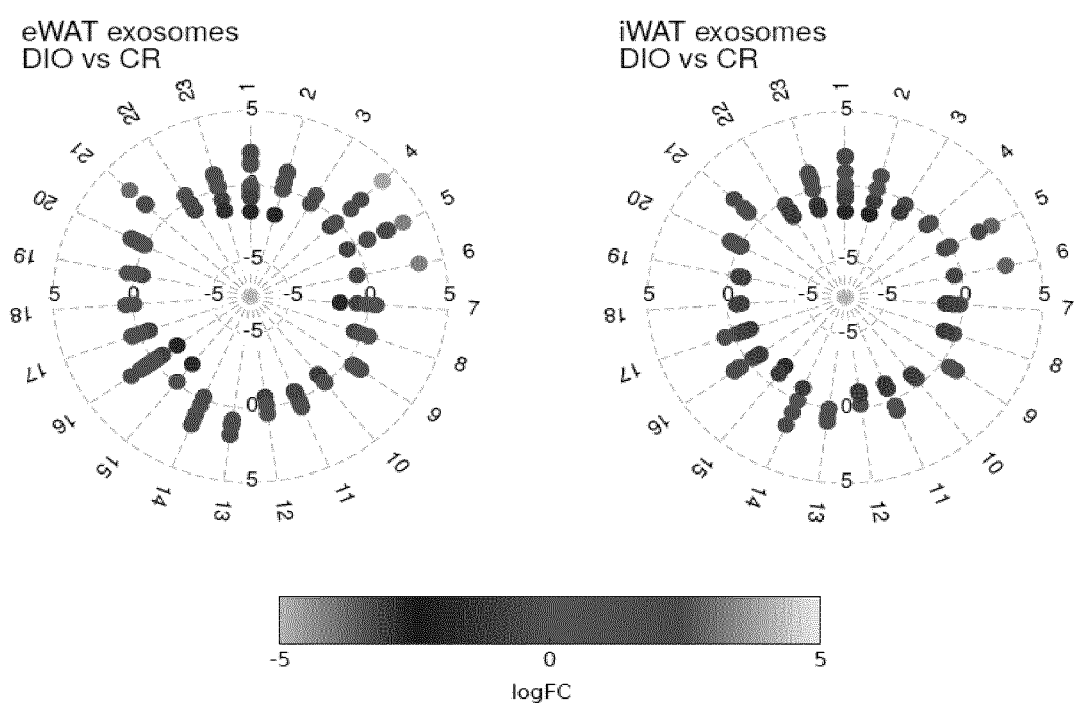

FIG. 2: Distinct exosomal protein signatures in adipocytes of lean, diet-induced obese and calorie restricted mice.

(A) Heatmap of significantly up- or down-regulated exosomal proteins from eWAT and iWAT of lean (n=5), diet induced obese (DIO) (n=5) and caloric restricted (CR) (n=6) samples. Exosomes from 5 mice were pooled for one sample replicate. Grey and yellow squares at the right side of the heat map indicate non-significant vs. significant regulation, respectively. (B) Venn diagrams showing total numbers of detected exosomal proteins in eWAT (left panel) and iWAT (right panel) in lean, DIO and CR mice. Venn diagram (C) displaying the overlap of significantly regulated proteins. (D) Selected enriched KEGG pathways sorted by functional classification. Log 10 p-values are shown as horizontal bars, a significance level of 0.05 is indicated as dashed line. (E) The regulation of exosomal proteins from eWAT and iWAT that were significantly up- or down-regulated by at least one dietary condition is shown in circle dot-plots. Each dot refers to the log Fold Change (color coded) of one protein mapped to the pathway displayed (1-23). Statistical significance was analyzed by ANOVA with Bonferroni false positive correction. Enrichment of KEGG Pathways was estimated using hypergeometric distribution tests.

Figure 3:
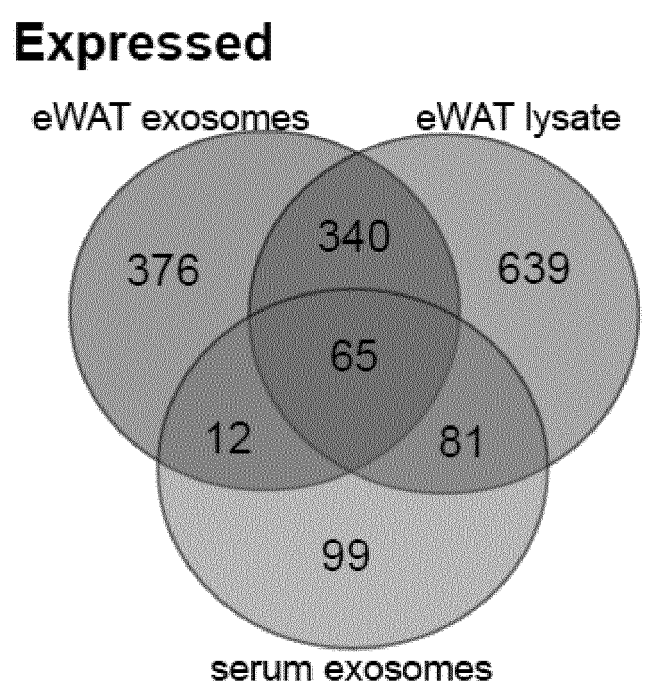
Figure 3:
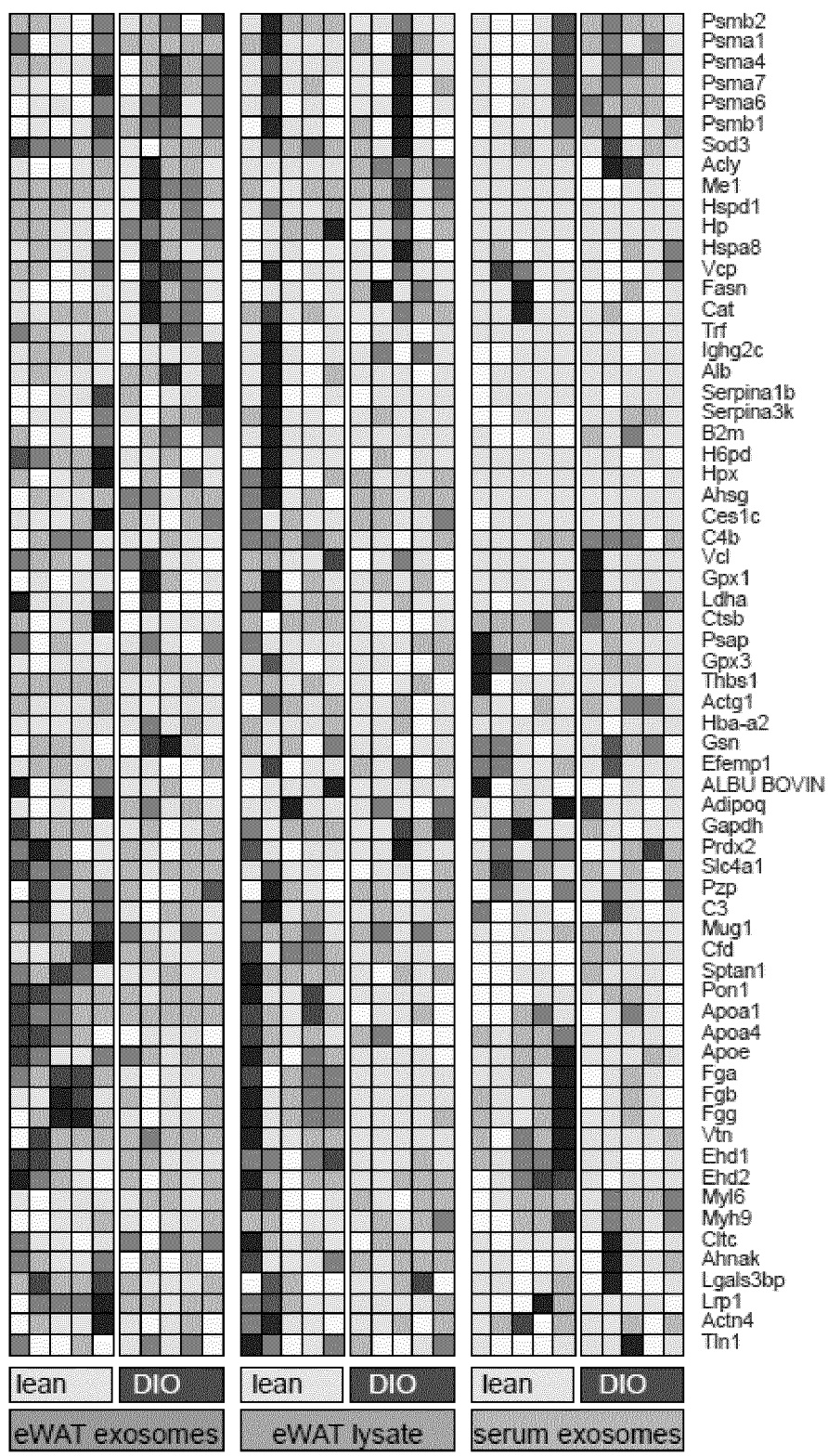
Figure 3:
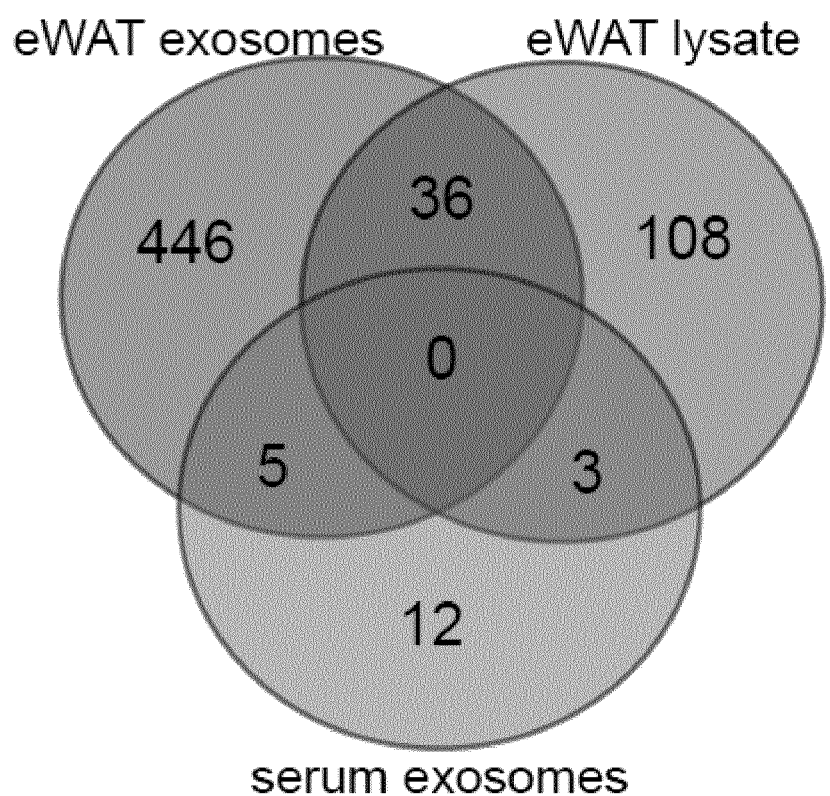
Figure 3:
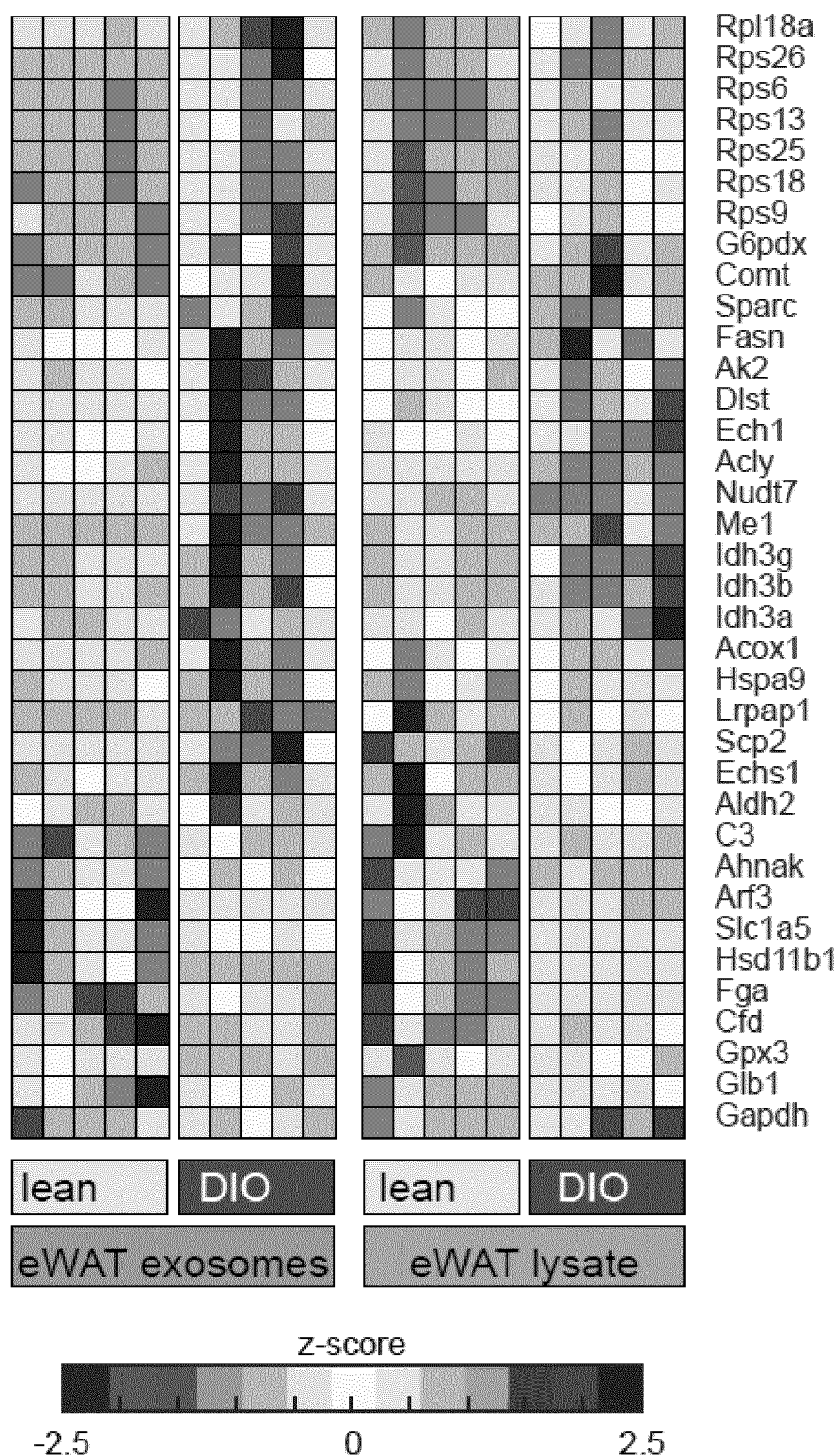
Figure 3:
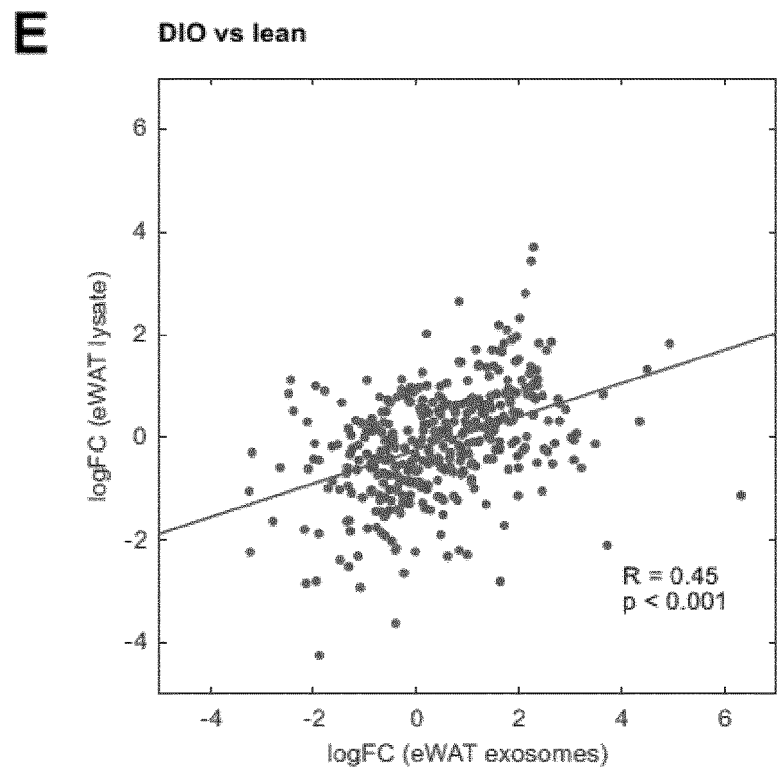
Figure 3:
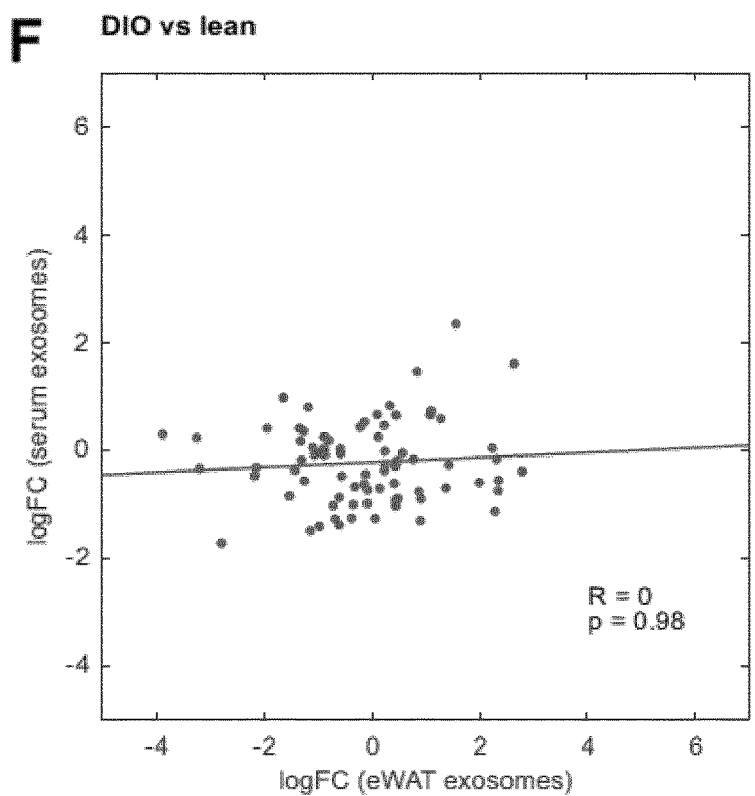
Figure 3:
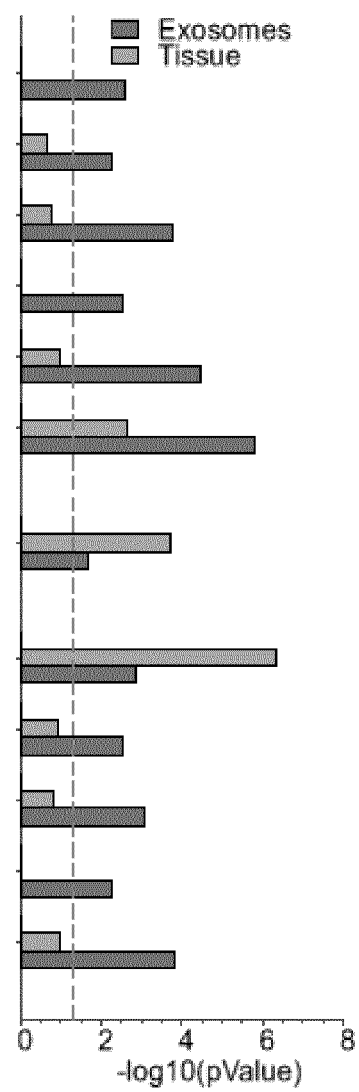
Figure 3:
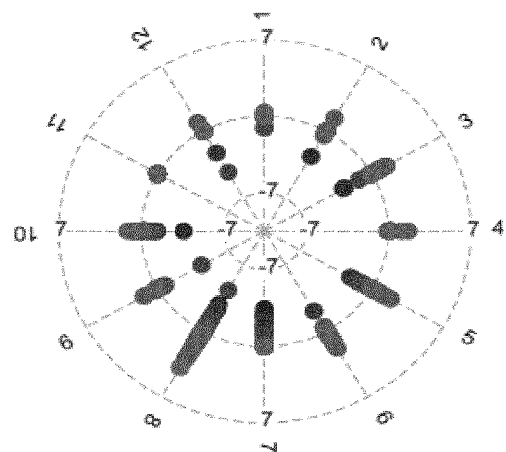
Figure 3:
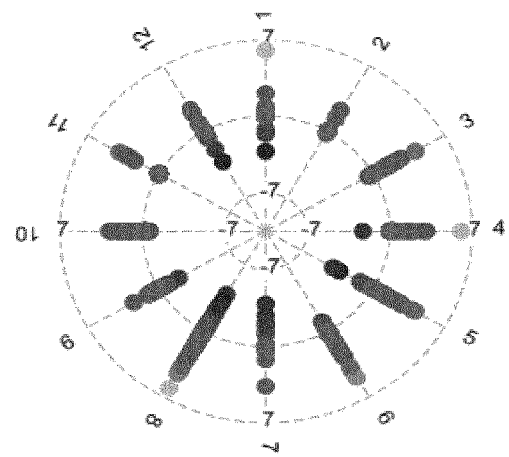
Figure 3:

FIG. 3: Comparative analysis of proteome profiles in eWAT adipocyte exosomes, eWAT tissue lysates and serum exosomes (A).

(A) Venn diagram showing total numbers of detected proteins isolated from eWAT- or serum exosomes in comparison with proteins from eWAT tissue lysates (combined hits from chow and DIO groups). (B) Heatmap of 65 common proteins detected in eWAT lysate and exosomes from eWAT and serum. (C) Venn diagram with significantly regulated proteins in eWAT or serum exosomes and eWAT lysates of lean vs. DIO mice (D) Heatmap of the 36 proteins with differential expression between eWAT exosomes and eWAT lysate. (E, F) Correlation of log FoldChange (log FC) expression levels (DIO vs. lean) between eWAT lysates and eWAT exosomal proteins (E), or between eWAT exosomes and serum exosomes (F) from lean and DIO mice. (G) Selected enriched KEGG pathways listed in functional classification order; log 10 p-values are shown as horizontal bars, a significance level of 0.05 is indicated as dashed line. Circle plots (H) show log FC expression of the regulated proteins identified in (C) and (D) mapped to KEGG pathways. Each dot refers to the log FC (color coded) of one protein mapped to the pathway displayed (1-12). Statistical significance was analyzed by ANOVA with Bonferroni false positive correction. Significance of correlation was tested using spearman rank correlation test. Enrichment of KEGG Pathways was estimated using hypergeometric distribution tests.

Figure 4:
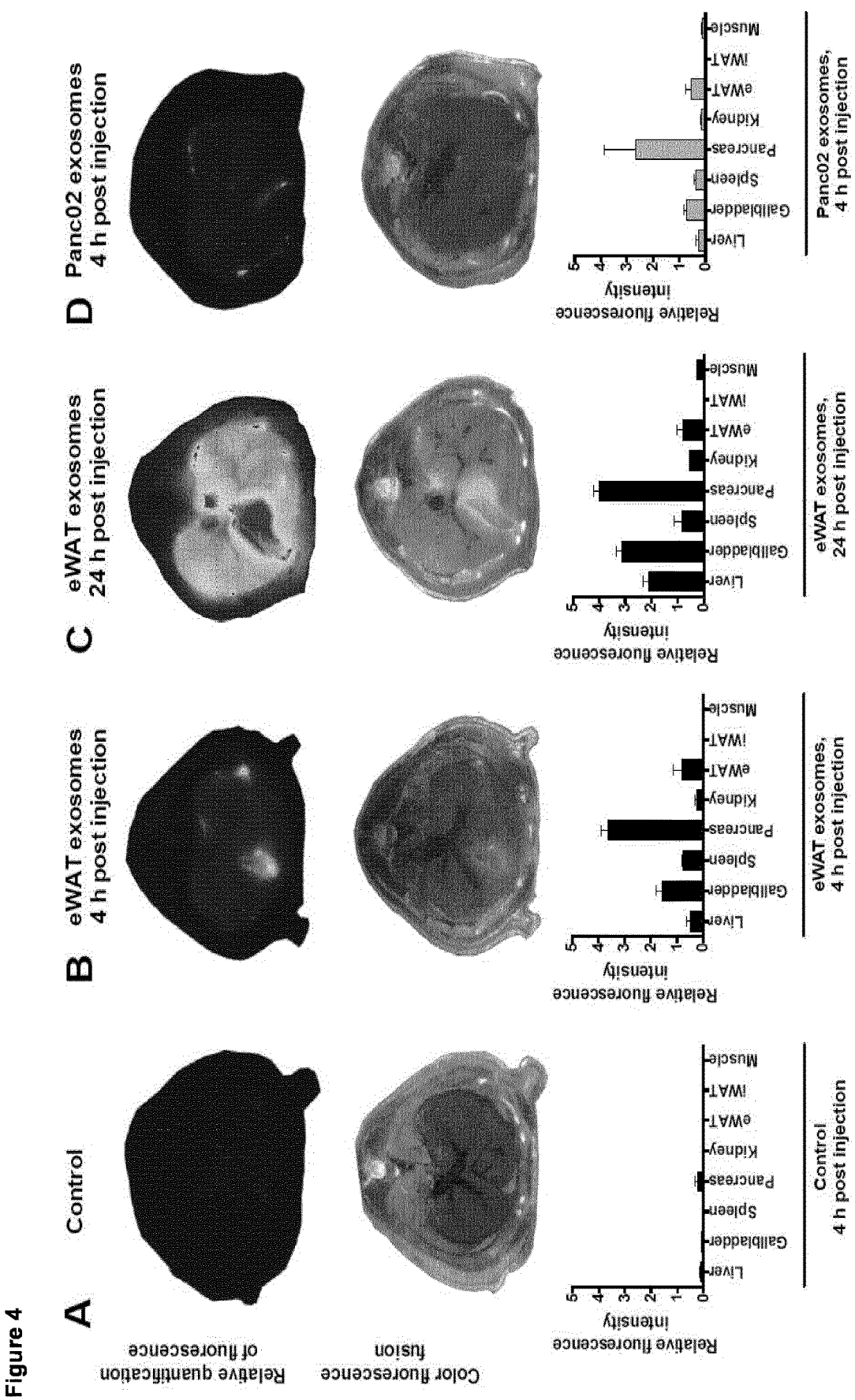

FIG. 4: Tissue specific uptake of fluorescently labeled eWAT exosomes in mice.

Representative cross-sections of multiscale and multispectral images of the whole cryosliced murine torso along the axial planes after fluorescence detection (upper panels), after color and fluorescence image fusion (middle panels) and relative quantifications of fluorescence intensities between the target organs (lower panels) in (A) DiR injected control mice, mice injected with (B) DiR labeled epididymal white adipose tissue (eWAT) (also called gonadal white adipose tissue (gWAT)) exosomes 4 h after injection, (C) DiR labeled eWAT (also called gWAT) exosomes 24 h after injection, or (D) DiR labeled Panc02 exosomes 4 h after injection. Data represent duplicate injections per condition.

Figure 5:
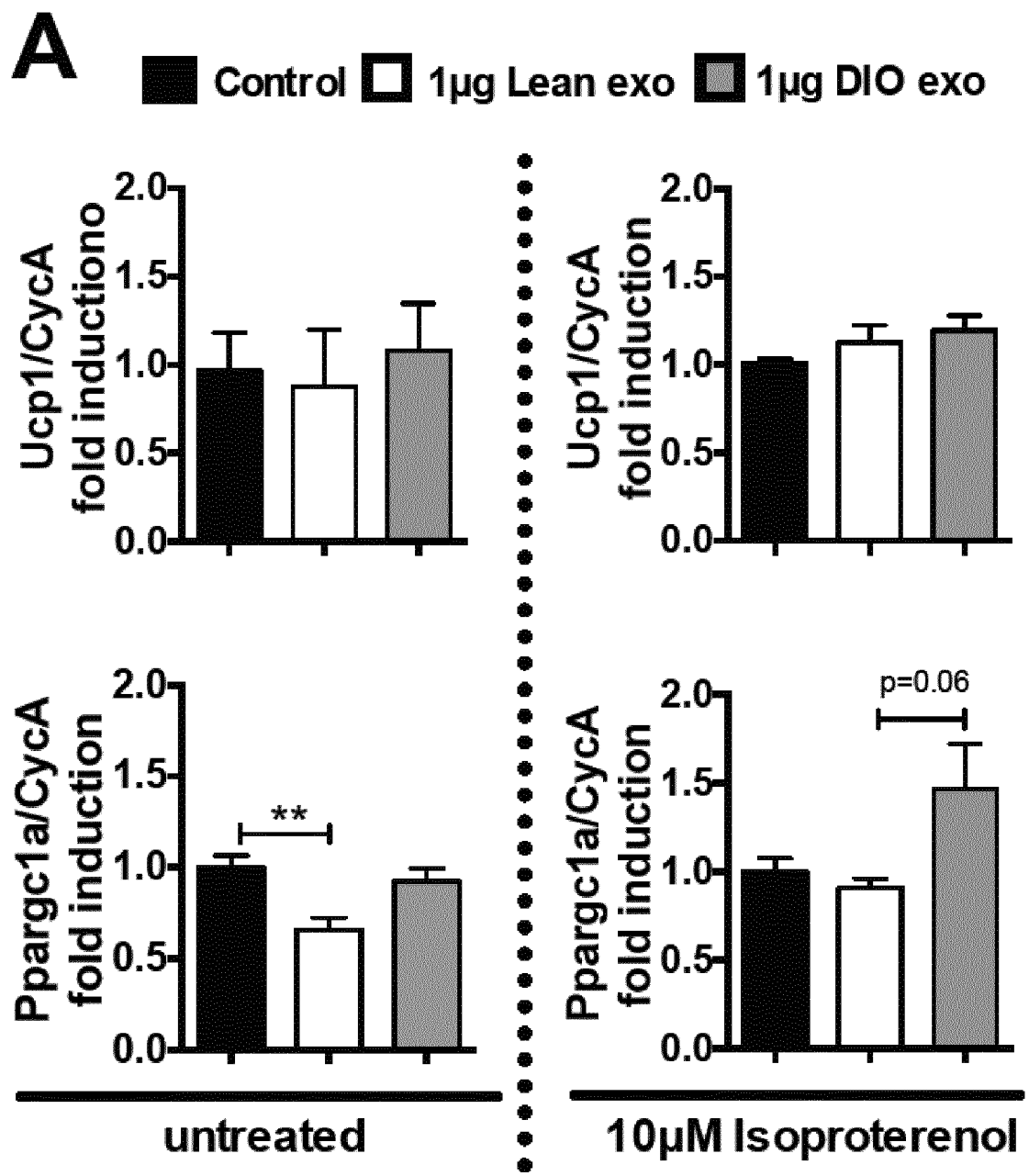
Figure 5:
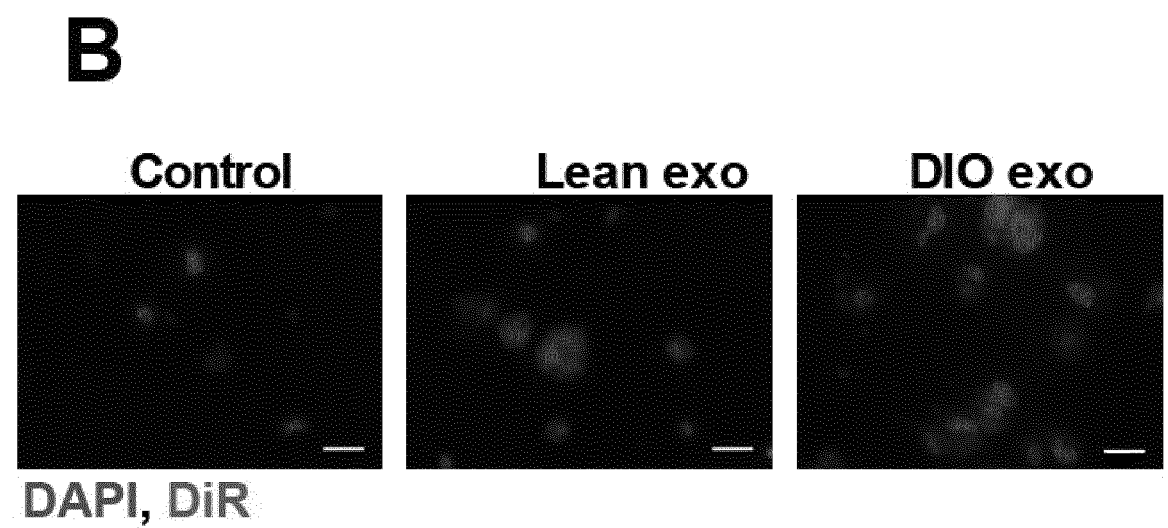
Figure 5:
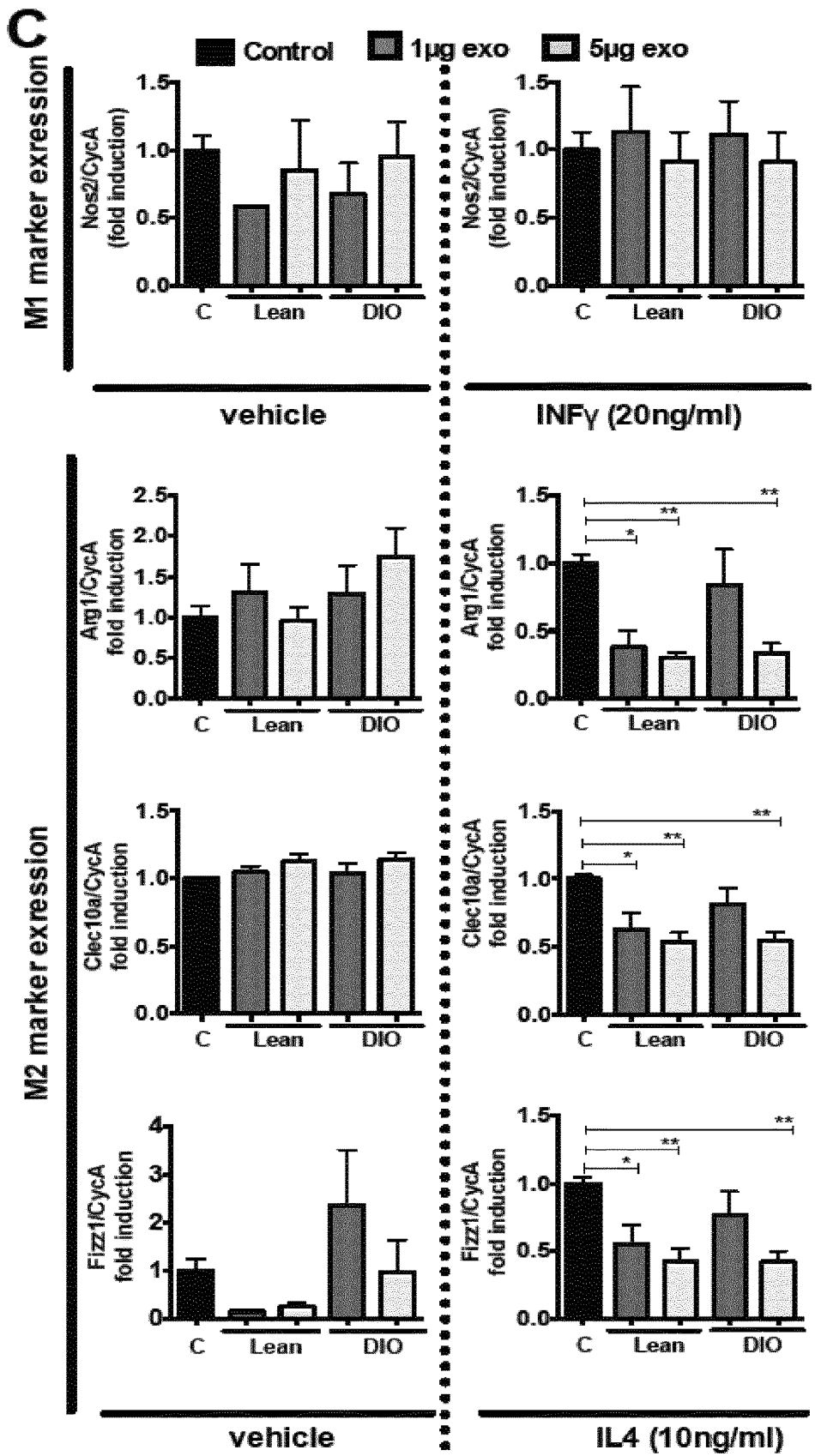
Figure 5:
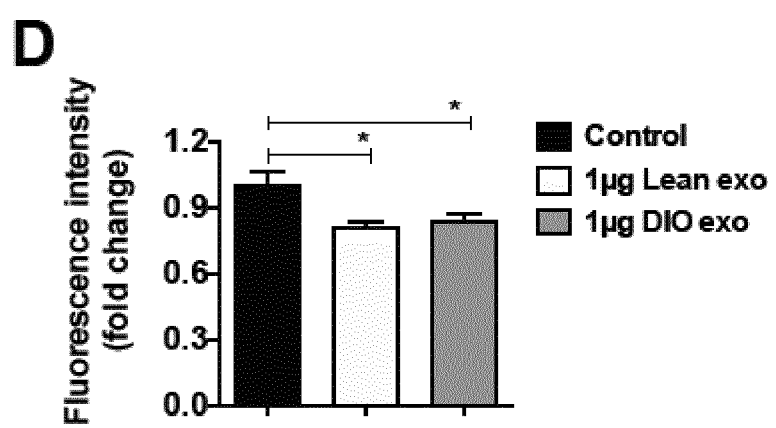
Figure 5:
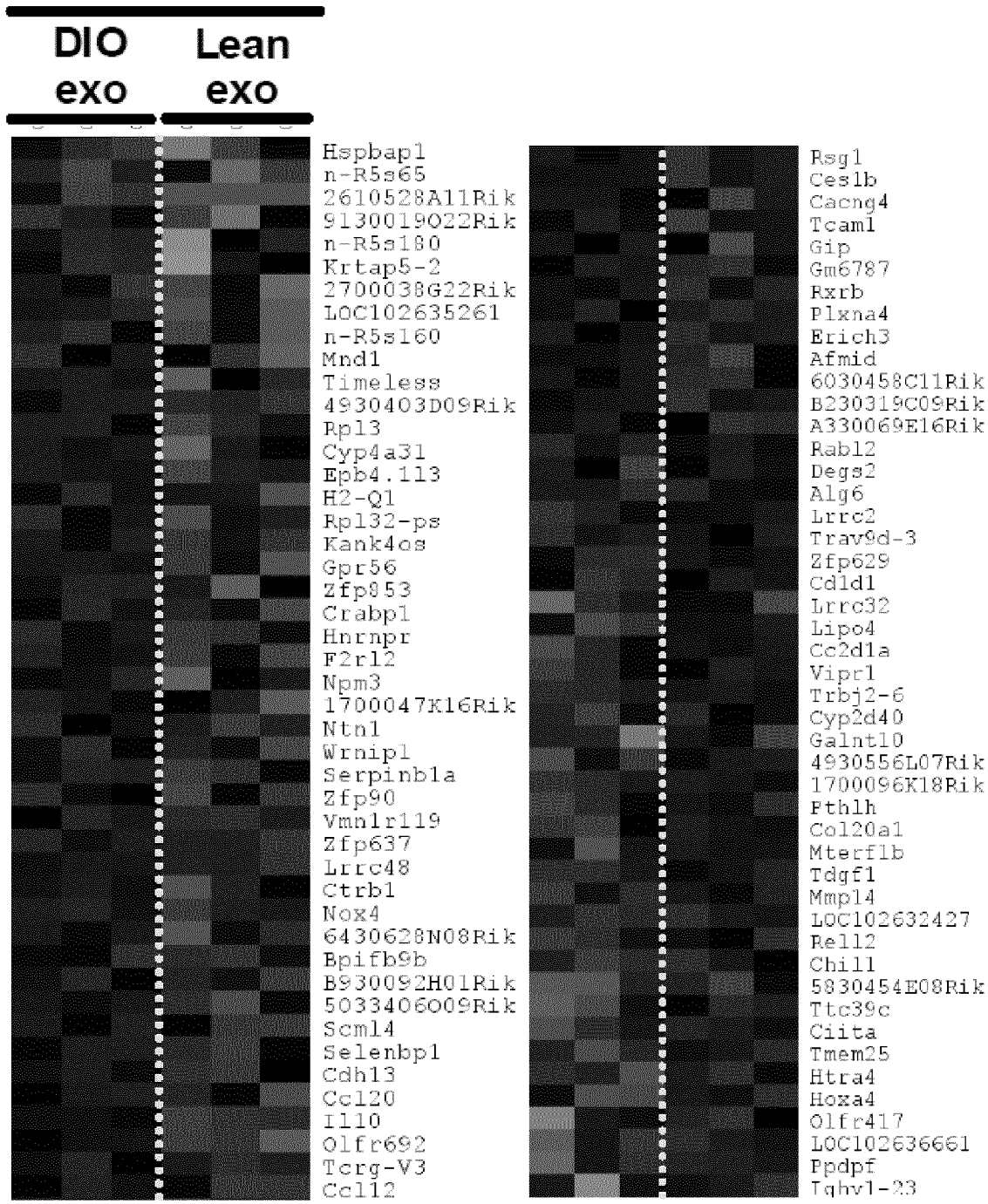
Figure 5:
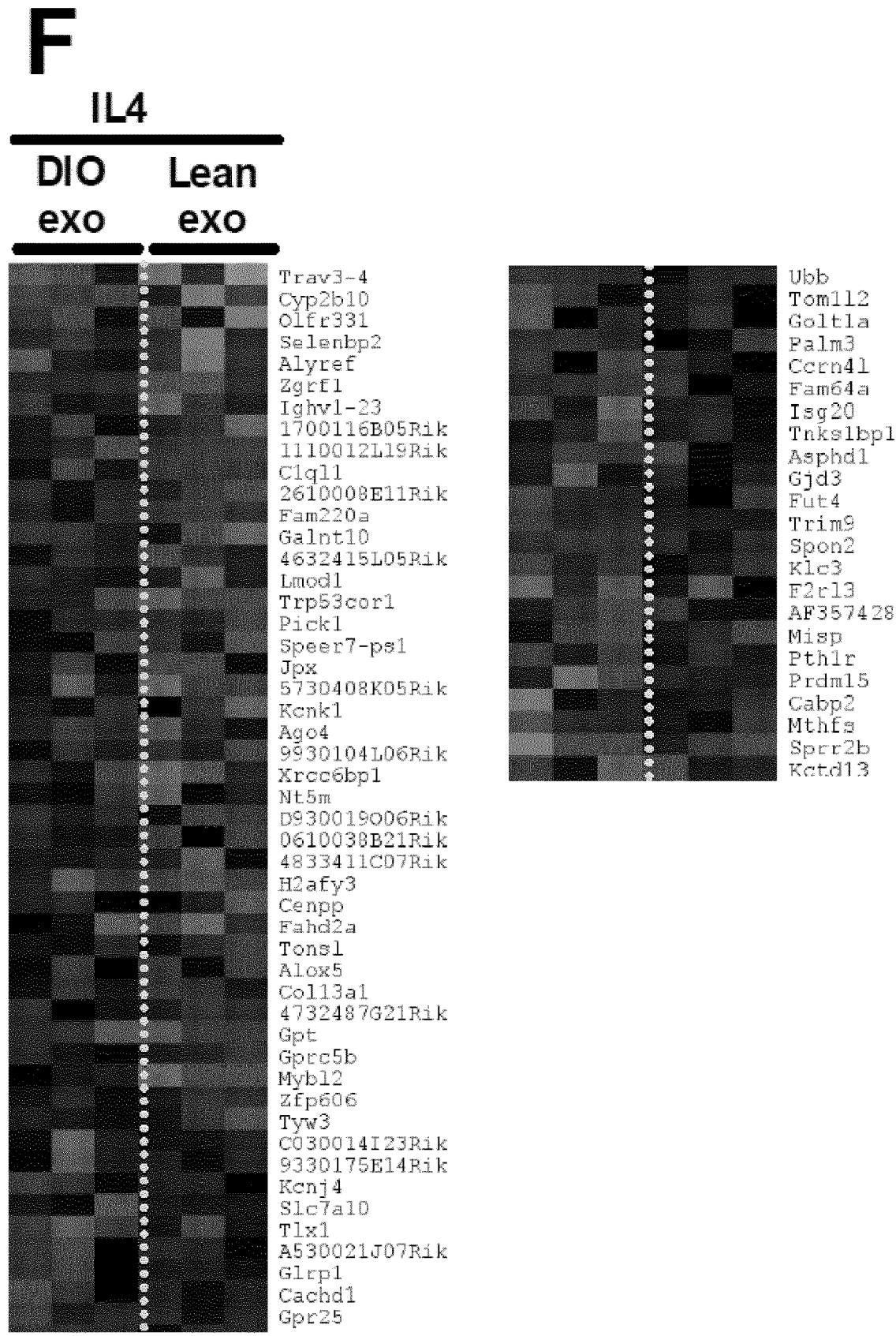

FIG. 5: Adipocyte derived exosomes exert paracrine effects on M2 macrophage polarization but not on iWAT browning.

(A) mRNA expression of UCP1 (upper panels) and PGC1α (lower panels) in primary inguinal adipocytes treated with control buffer or 1 μg of iWAT exosomes isolated from lean or obese mice. To induce browning in vitro, cells were treated with 10 μM isoproterenol after a preceding exosome treatment for 24 h (right panel). Gene expression was assayed in duplicates and displayed from two (INFγ stimulation) or three (IL4 stimulation) independent BMBM and exosomal preparations. All data were normalized to the respective buffer controls. (B) Representative images of DiR-labeled exosomes taken up into bone marrow derived macrophages (BMDMs) after 24 h of incubation with buffer (left panel), lean (middle panel) or DIO (right panel) eWAT exosomes. (C) M1/M2 marker gene expression of BMDMs treated with 1 μg or 5 μg exosomes isolated from eWAT of lean and obese mice or buffer control (C). BMDMs were treated with INFγ [20 ng/ml] to induce M1 commitment, or with IL-4 (10 ng/ml) to promote M2 polarization. (D) BMDMs display phagocytotic uptake of fluorescently labeled *E. coli* particles 1.5 h hours after co-exposure with eWAT exosomes of lean and obese mice. (E-F) Heatmaps showing gene expression profiles of vehicle (E) or IL-4 stimulated BMDMs (F), treated with 5 μg eWAT exosomes from lean and DIO mice (n=3 independent replicates. Most predicted and non-coding genes are not shown). All data are expressed as means±SEM. Statistical significance was determined by One-Way ANOVA and multiple comparison correction using Sidak (A) or Dunnet's (C, D) multiple comparison test. Gene-wise testing for differential expression was done employing the limma t-test and Benjamini-Hochberg multiple testing correction (FDR<10%) (E, F).

Figure 6:
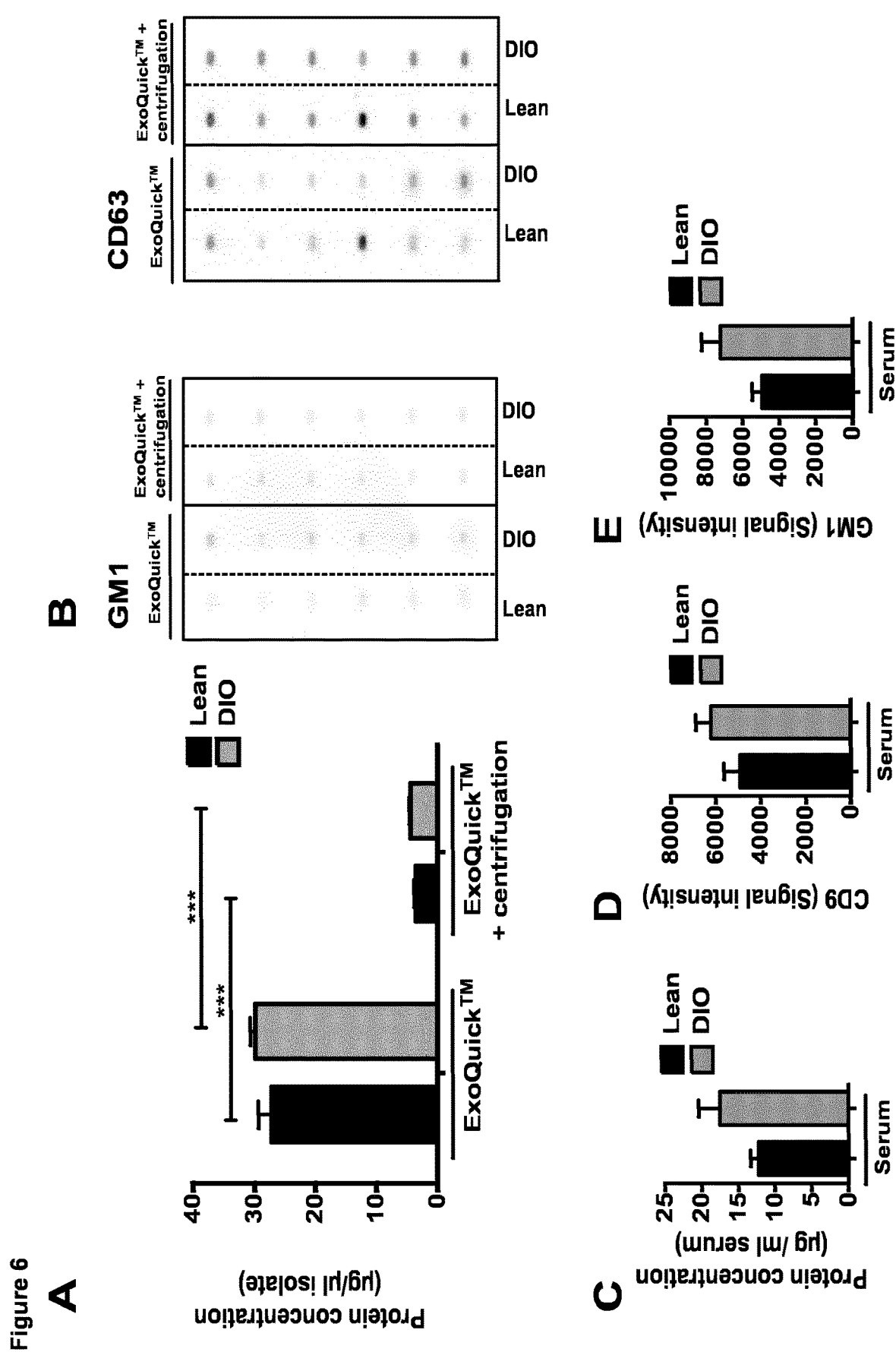

FIG. 6: (A) Protein concentrations of serum exosomes isolated from lean and diet-induced obese (DIO) mice via ExoQuick™ precipitation reagent or ExoQuick™ reagent with additional centrifugation of the crude exosomal isolates (n=16 for lean, and n=15 for DIO mice). (B) Dot blots of random samples from the same isolates with GM1 (left panel) and CD63 (right panel) immunostaining. Similar signal intensities of exosomal surface markers (GM1 and CD63) suggest a contamination of the serum isolates with non-exosomal serum proteins, which can be reduced by additional centrifugation of the ExoQuick™ isolates. (C) Exosomal protein concentrations after this improved Exo-Quick™ isolation were similar for serum from lean and DIO mice (n=12). CD9 (D) and GM1 (E) immunostaining corroborate similar serum exosome levels in lean and obese mice. Statistical significance was analyzed using a One-Way ANOVA followed by Sidak's multiple comparisons test (A), or two-tailed student's t-test (C-E). Significant differences are indicated as (***) P<0.001

Figure 7:
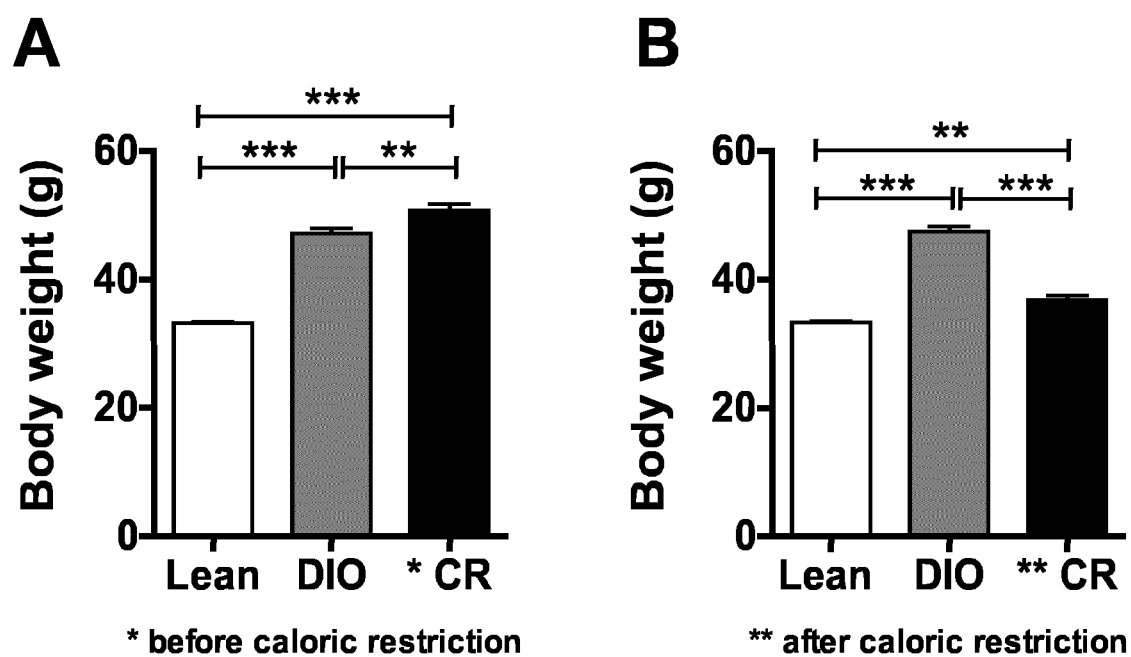

FIG. 7: ((A-B) Body weights of lean, DIO and CR mice before (A) and after (B) caloric restriction of the formerly obese group. Statistical significance (B and C) was determined by One-Way ANOVA and Bonferroni multiple comparison test. Significant differences between groups are displayed as (*) P<0.05 () P<0.01 and (*) P<0.001.

Figure 8:
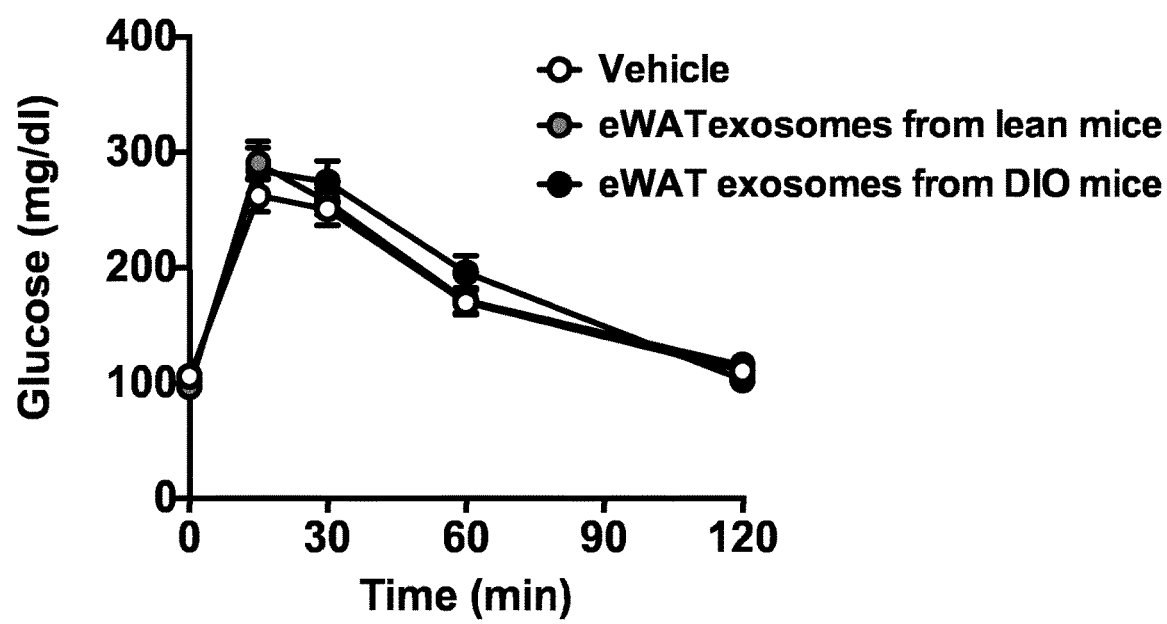

FIG. 8: Glucose excursion of naïve C57BL/6 mice pre-injected with vehicle (n=25) or 10 µg of eWAT exosomes from lean (n=16) or DIO (n=13) mice four hours prior to an intraperitoneal (ip.) bolus of 1.7 mg glucose per g body weight. Two-Way ANOVA revealed no significant differences between the three groups.

Figure 9:
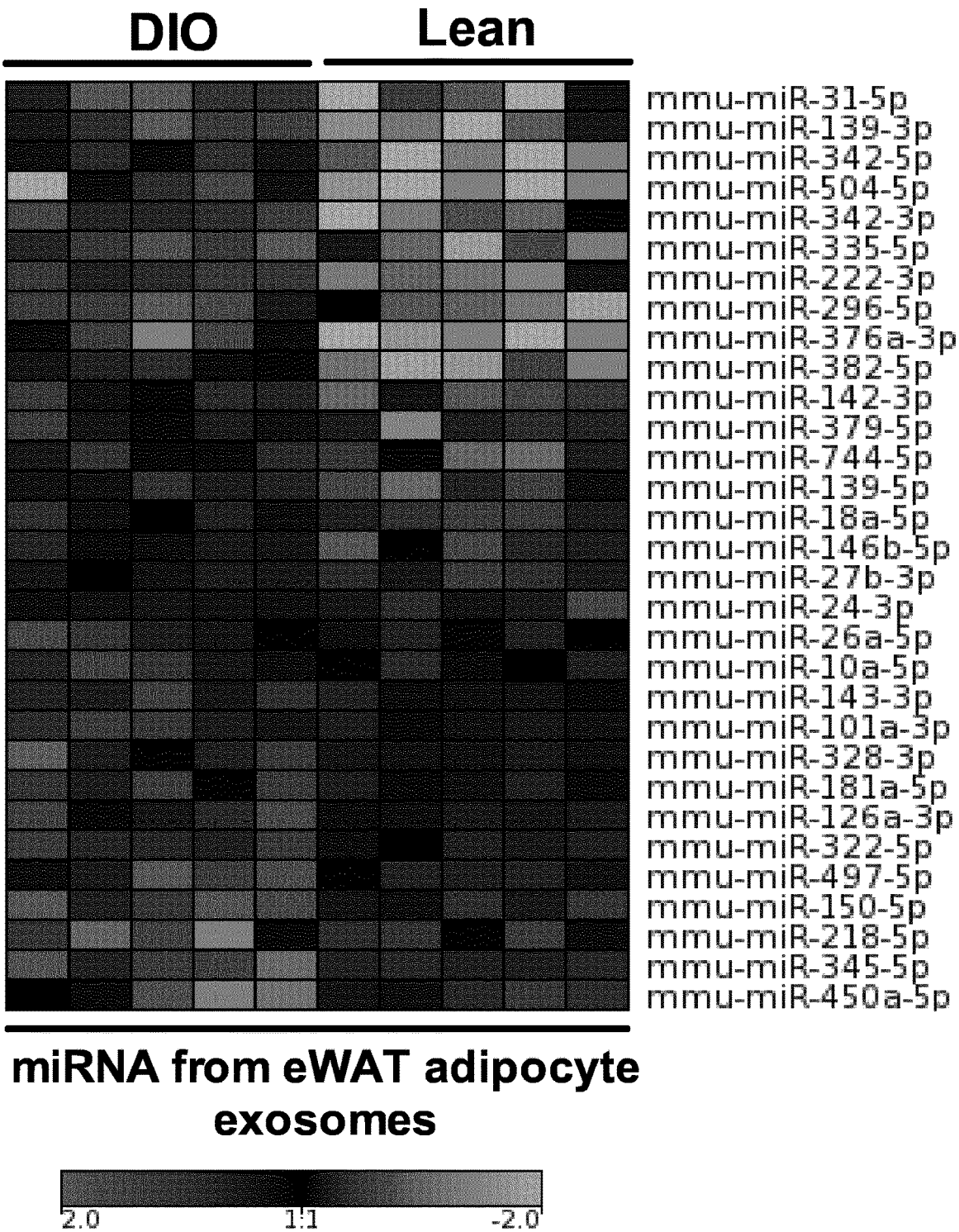

FIG. 9: (A) Heatmap of 31 significantly different miRNAs of eWAT adipocyte exosomes from lean (n=5) and DIO (n=5) mice. For statistical analysis the moderated limma t-test was applied in combination with the Benjamini-Hochberg correction for multiple testing. Probe sets with a False Discovery Rate (FDR)<10% and a fold change<1.5 were considered as significant. A detailed overview of all 31 significantly different miRNAs from the heatmap is depicted in Table 2. (B) Functional analysis of the same dataset of said significantly different miRNAs (here only 20 miRNAs are depicted) of eWAT adipocyte exosomes from lean (n=5) and DIO (n=5) mice using a more stringent evaluation. Probe sets with a False Discovery Rate (FDR)<5% were considered as significant.

Figure 10:
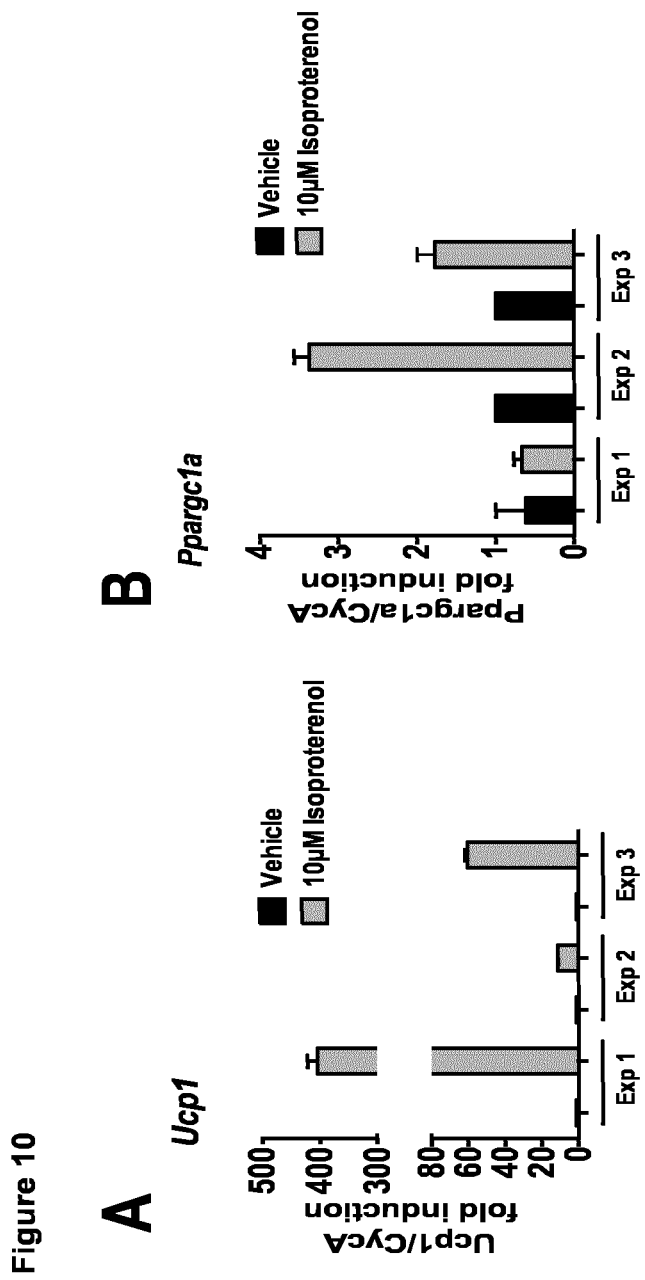

FIG. 10. (A-B) mRNA expression of Ucp1 (A) and Ppargc1a (B) in primary subcutaneous adipocytes after 6 h of isoproterenol stimulation.

Figure 11:
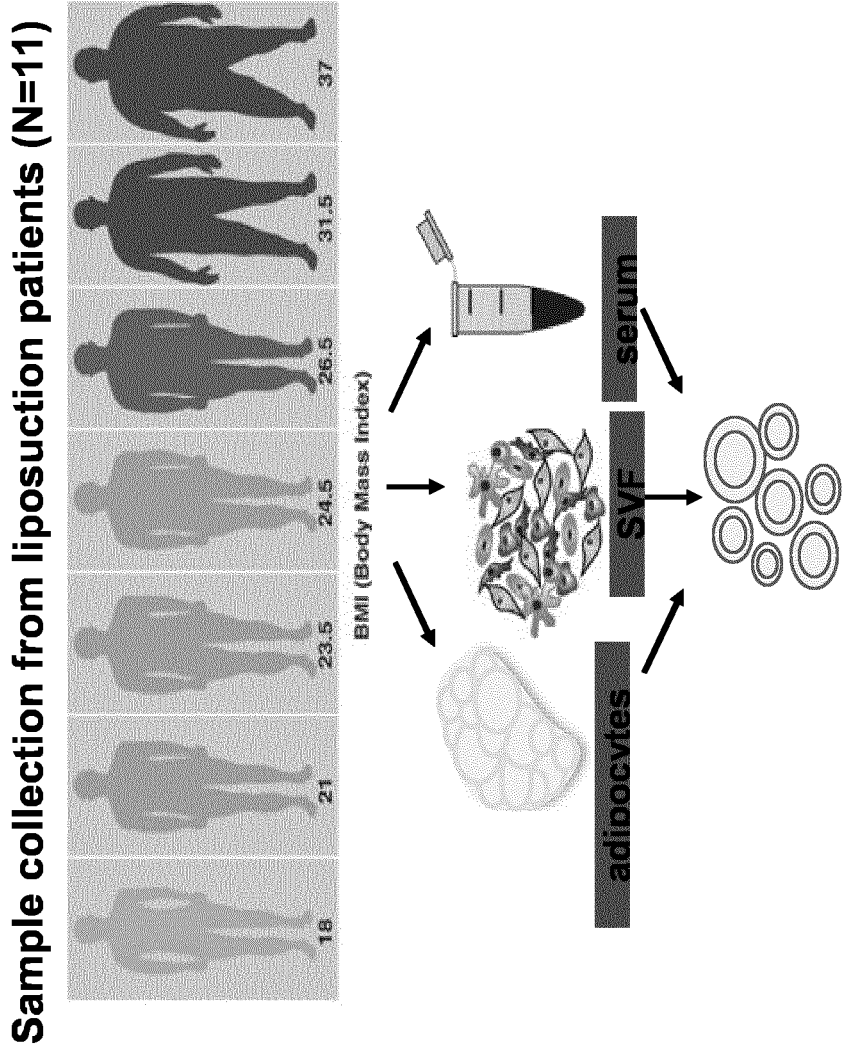

FIG. 11: Sample collection from liposuction patients.

Adipose tissue (AT) samples, adipocyte- and stromal vascular fraction of AT samples as well as serum samples are obtained from liposuction patients (n=11) with different BMIs ranging from 18 to 37.

Figure 12:
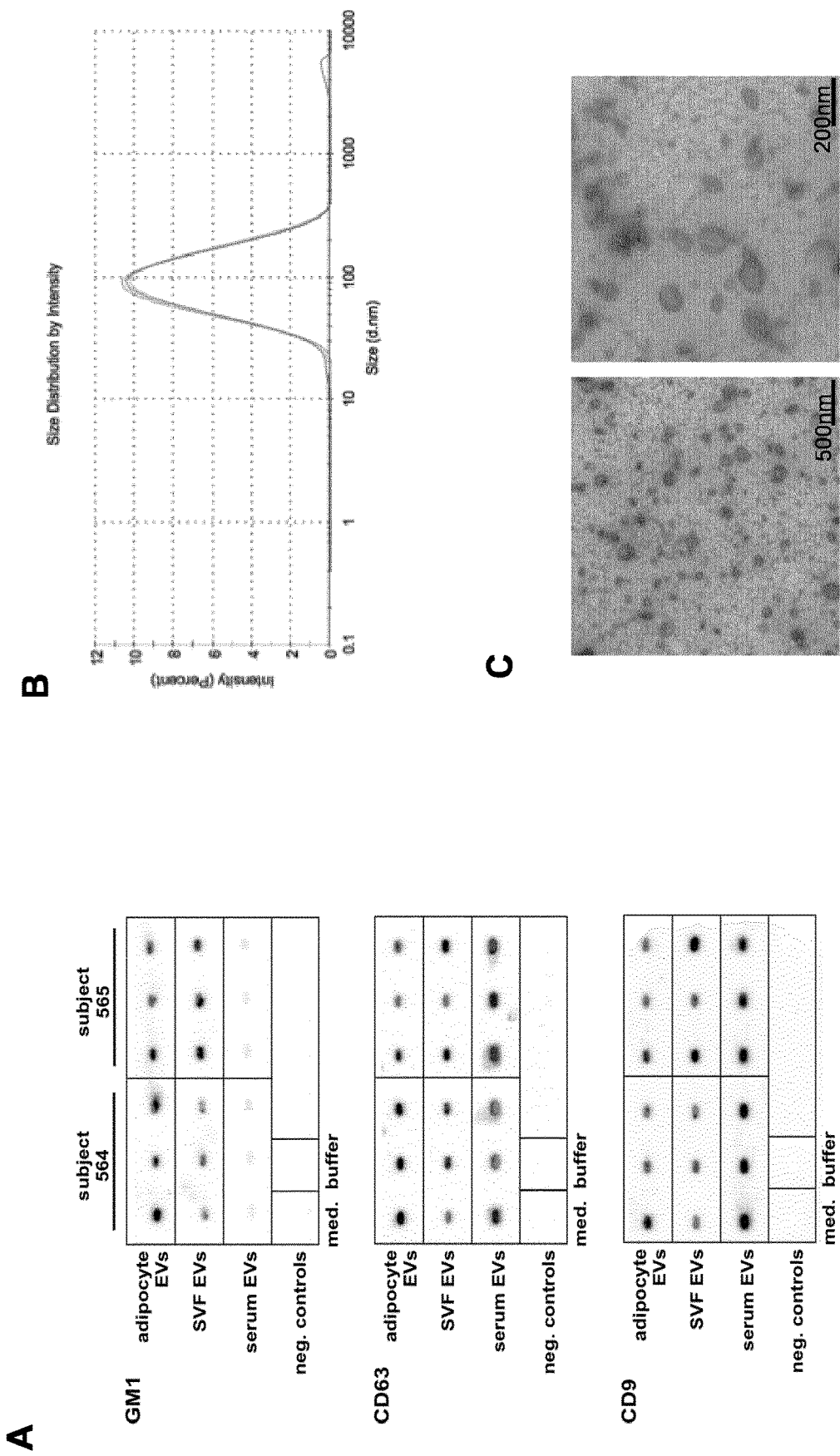

FIG. 12: Characterization of human adipocytes derived EVs.

In the following figure, EVs preferably comprise exosomes to the highest amount. (A) Dot blots of EVs isolated from explant cultures of human liposuction samples of two random patients (IDs: 564 and 565). EVs of the adipocyte fraction (first line) from stromal-vascular fraction EVs (SVF, second line) and EVs isolated from serum samples of the same patients (third line) were compared negative controls (cultivation medium and EV buffer). Blots were immunostained using antibodies against the EV surface markers GM1 (upper panel), CD63 (middle panel) and CD9 (lower panel). (B) Dynamic light scattering (DLS) revealed that explant adipocytes from human liposuction samples release a population of vesicles ranging in size from 30 to 300 nm with an average size of 101.5±53.0 nm. (C) Representative transmission electron microscopy images of EVs isolated from human adipocytes from a liposuction sample of a patient. Both images were taken at different magnifications from the same patient EV sample. EVs reveal a typical cup-shaped and double-membrane structure with a size of approximately 40-180 nm.

Figure 13:
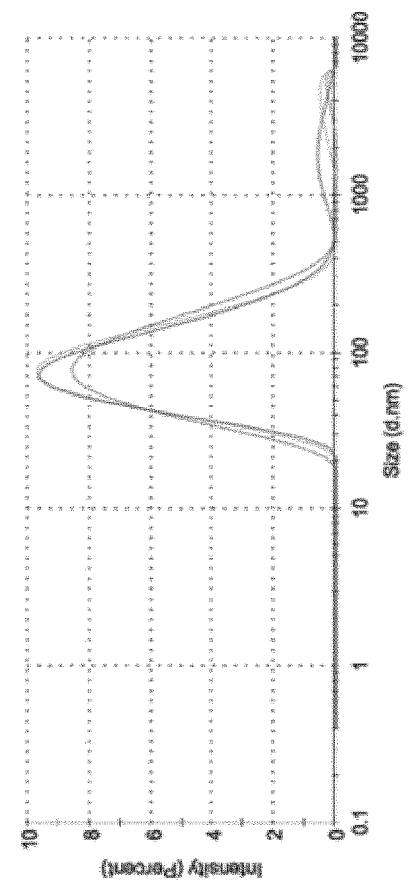
Figure 13:
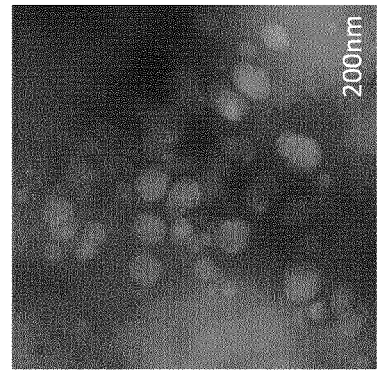
Figure 13:
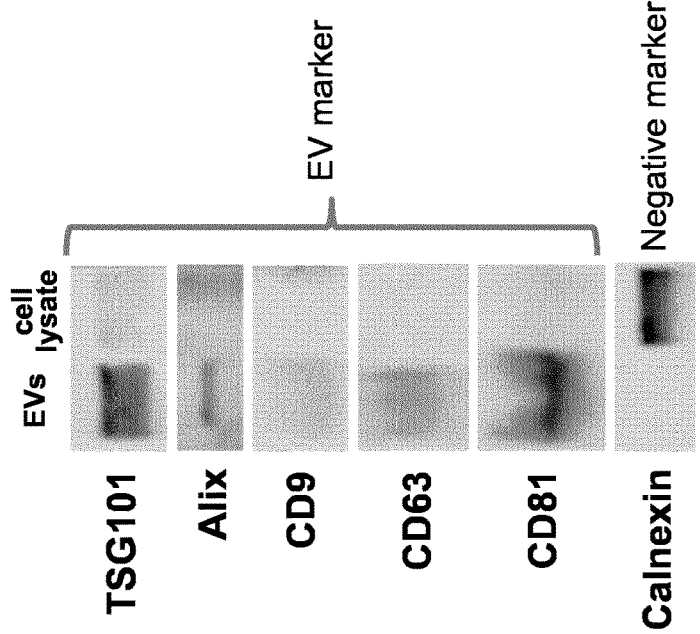

FIG. 13: Basic characterization of EVs isolated from cell culture media of differentiated human Simpson Golabi Behmel Syndrome (SGBS) cells for later mouse immunization.

In the following figure, EVs preferably comprise exosomes to the highest amount. (A) Western blots of EVs isolated from culture medium of differentiated SGBS cells and of SGBS cell lysate to demonstrate the typical marker enrichment in EVs compared to SGBS lysates. Blots were immunostained using antibodies against the EV surface markers TSG101, Alix, CD9, CD63, CD81 and the endoplasmatic reticulum-protein Calnexin as negative control. Antibodies were purchased from Thermo Fisher Scientific, USA (TSG101), BioLegend, USA (Alix and CD81) or Santa Cruz, USA (CD9 and CD63). (B) Dynamic light scattering (DLS) revealed that differentiated SGBS cells release a population of vesicles ranging in size from 30 to 300 nm with an average size of 101.1±67.04 nm. (C) Representative transmission electron microscopy image of EVs isolated from differentiated SGBS cells. EVs show a typical round and cup-shaped morphology with a size of approximately 40-150 nm.

Figure 14:
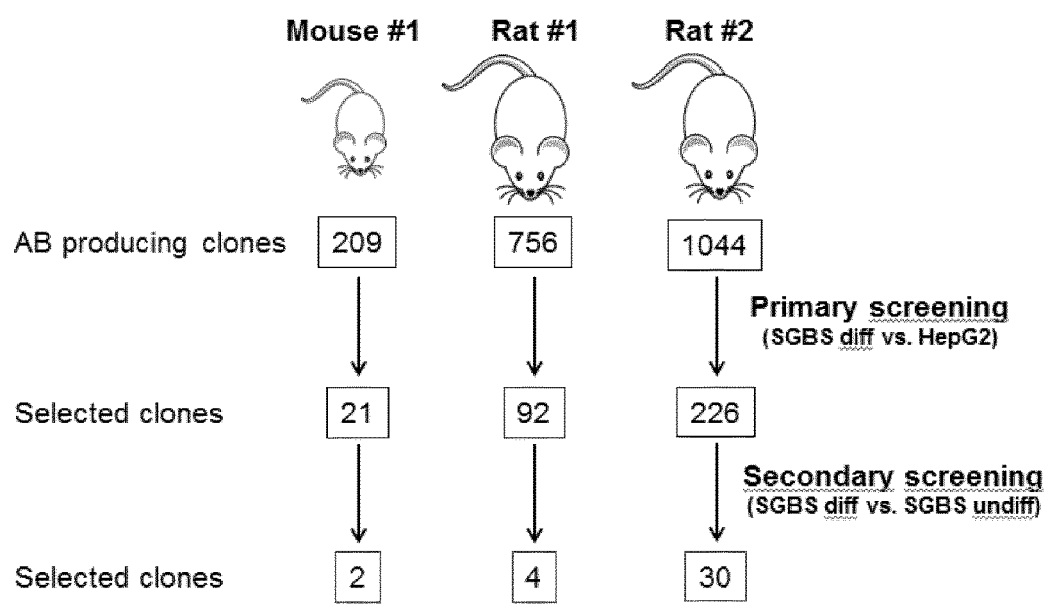

FIG. 14: Overview of the screening for adipocyte EV specific antibodies.

In the following figure, EVs preferably comprise exosomes to the highest amount. After the primary and the secondary screening for adipocyte EV specific antibodies, 5 antibody producing clones (14H5, 15G1, 18G1, 23A11 and 29H2) were selected, 2 from mouse #1 and 4 from rat #1.

Figure 15:
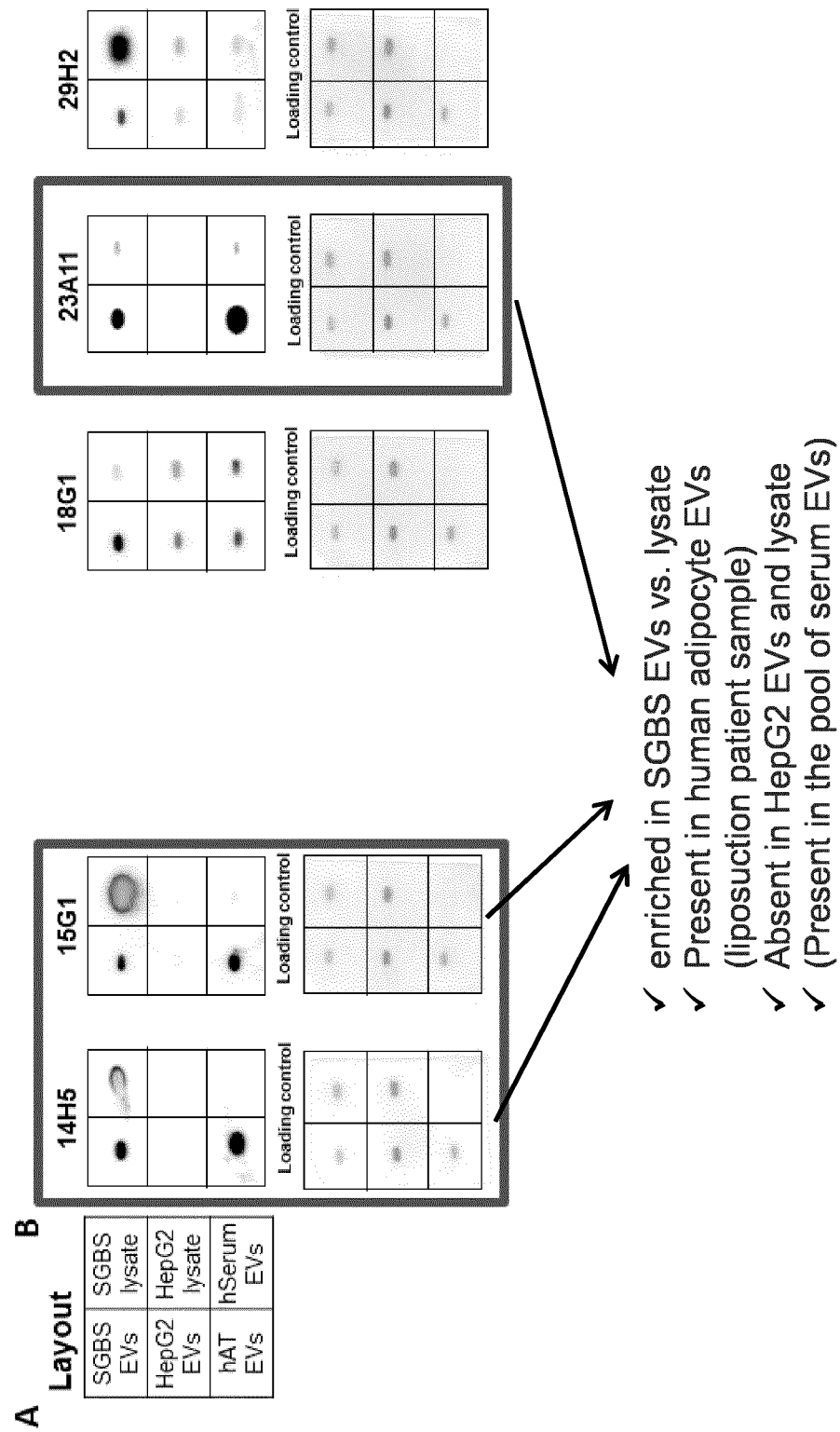

FIG. 15: Antibody specificity testing using adipoctye specific EVs.

Figure 16:
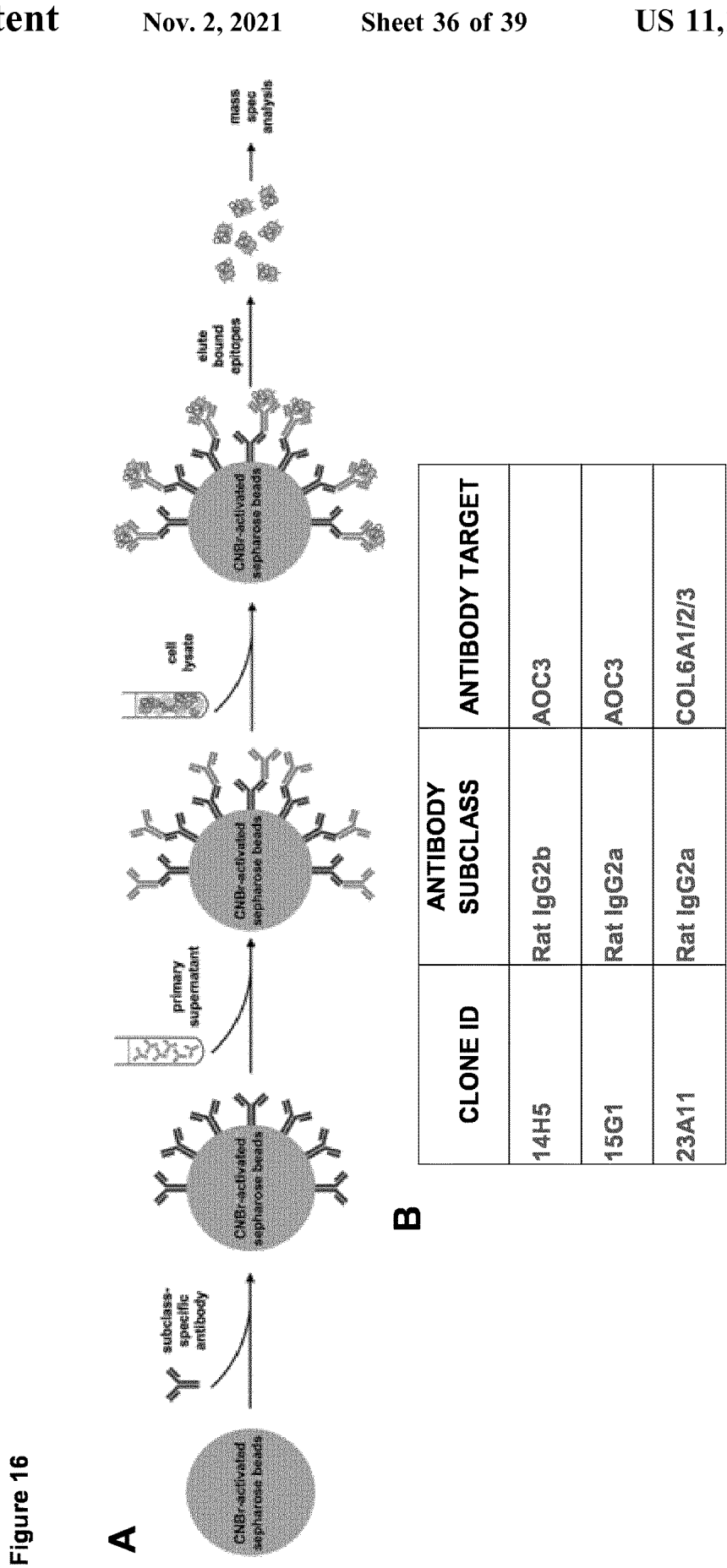

In the following figure, EVs preferably comprise exosomes to the highest amount. (A) Sample spotting layout using adipocty specific EVs (in the following EVs preferably comprise exosomes). (B) Spotted membranes, incubated with selected antibody clones (14H5, 15G1, 18G1, 23A11 and 29H2). Three antibodies (14H5, 15G1 and 23A11; marked by brown boxes) showed a highly specific binding to SGBS and hAT EVs and SGBS lysate as positive control. Weak signal was detected in human serum EV samples, which may represent the fraction of adipocyte secreted EVs. Antibodies (18G1 and 29H2; without box) failed to demonstrate organ specificity. The presence of loaded protein (loading controls) was proven by Ponceau staining FIG. 16: Target identification by mass spectrometry.

In the following figure, EVs preferably comprise exosomes to the highest amount. (A) Target identification performed by IP of SGBS cell EVs (in the following EVs preferably comprise exosomes) using antibody containing primary supernatants. (B) Monoclonal antibody producing hybridoma clone ID (14H5, 15G1, and 23A11) with corresponding antibody subclasses, and top hit antibody targets: AOC3 (amine oxidase, copper containing 3) and COL6A1/2/3 (Collagen Type VI alpha 1/2/3) after said purified antibodies from stabilized monoclonal antibody producing clones were reinvestigated via mass spectrometry.

Figure 17:
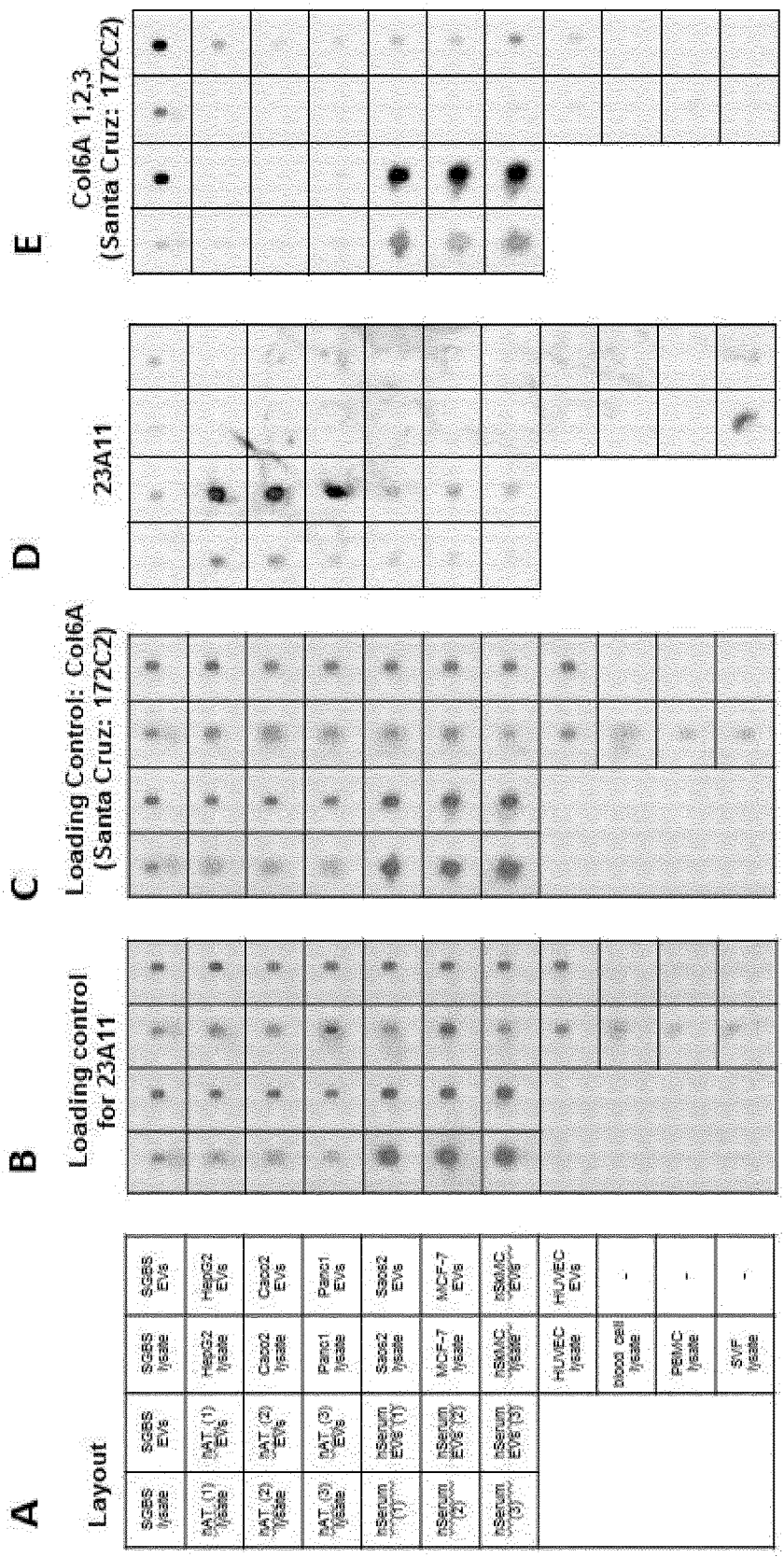

FIG. 17: Antibody characterization for antibody 23A11.

In the following figure, EVs preferably comprise exosomes to the highest amount. (A) Sample spotting layout of the loading scheme. (B) and (C) The presence of loaded protein prior to antibody staining (loading controls) was proven by Ponceau staining. (D) Spotted membranes, incubated with our selected antibody clone 23A11 demonstrating a weak positive signal in SGBS-EVs (used as antigen for mouse immunization), a weak positive signal in all hAT samples and a strong positive signal in hAT EV. No antibody binding was observed for EVs isolated from other human non-adipose tissue cell lines. A weak positive staining was observed for hSerum and hSerum EVs in combination with the absence of antibody binding to endothelial HUVEC EVs, blood cell lysates and PBMC lysates is indicative for the presence of circulating hAT EVs. (E) Spotted membranes, incubated with a commercially available antibody against the top hit antibody target identified via mass spectrometry: Collagen Type VI alpha 1/2/3 (Col 6A 1, 2, 3), demonstrating non-specific binding to non-adipose tissue derived EVs.

Figure 18:
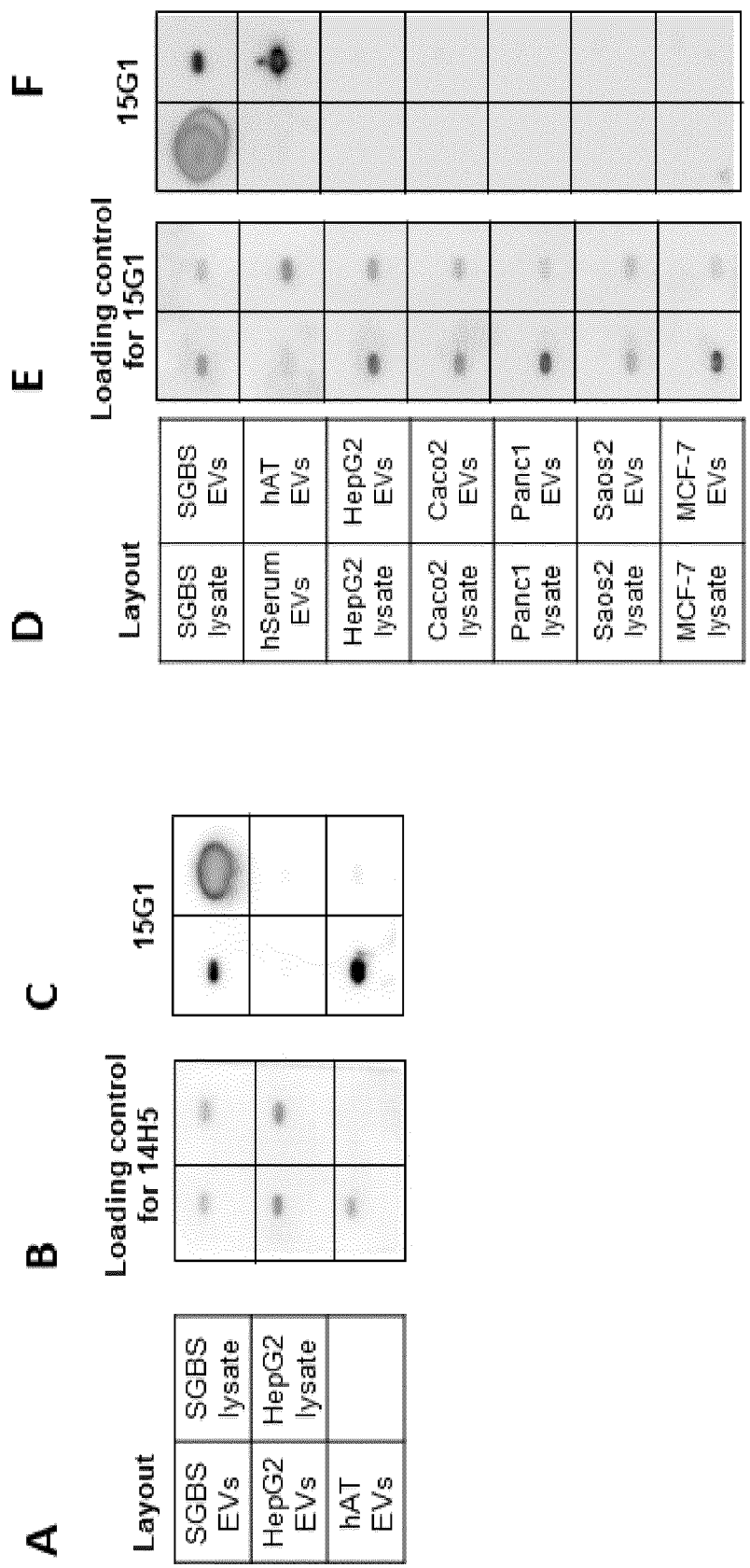

FIG. 18: Antibody characterization for antibody 15G1.

In the following figure, EVs preferably comprise exosomes to the highest amount. (A) and (D) Sample spotting layout of the loading schemes. (B) and (E) The presence of loaded protein prior to antibody staining (loading controls) was proven by Ponceau staining. (C) Spotted membranes incubated with our selected antibody clone 15G1 demonstrating a positive signal in SGBS-EVs (used as antigen for mouse immunization) and SGBS lysates and hAT EVs. No antibody binding was observed for HepG2 lysates or HepG2 EVs. (F) Spotted membranes, incubated with our selected antibody clone 15G1 demonstrating a positive signal in SGBS-EVs (used as antigen for mouse immunization) and SGBS lysates and hAT EVs, but no binding to lysates or EVs from other human non-adipose tissue cell lines.

Figure 19:
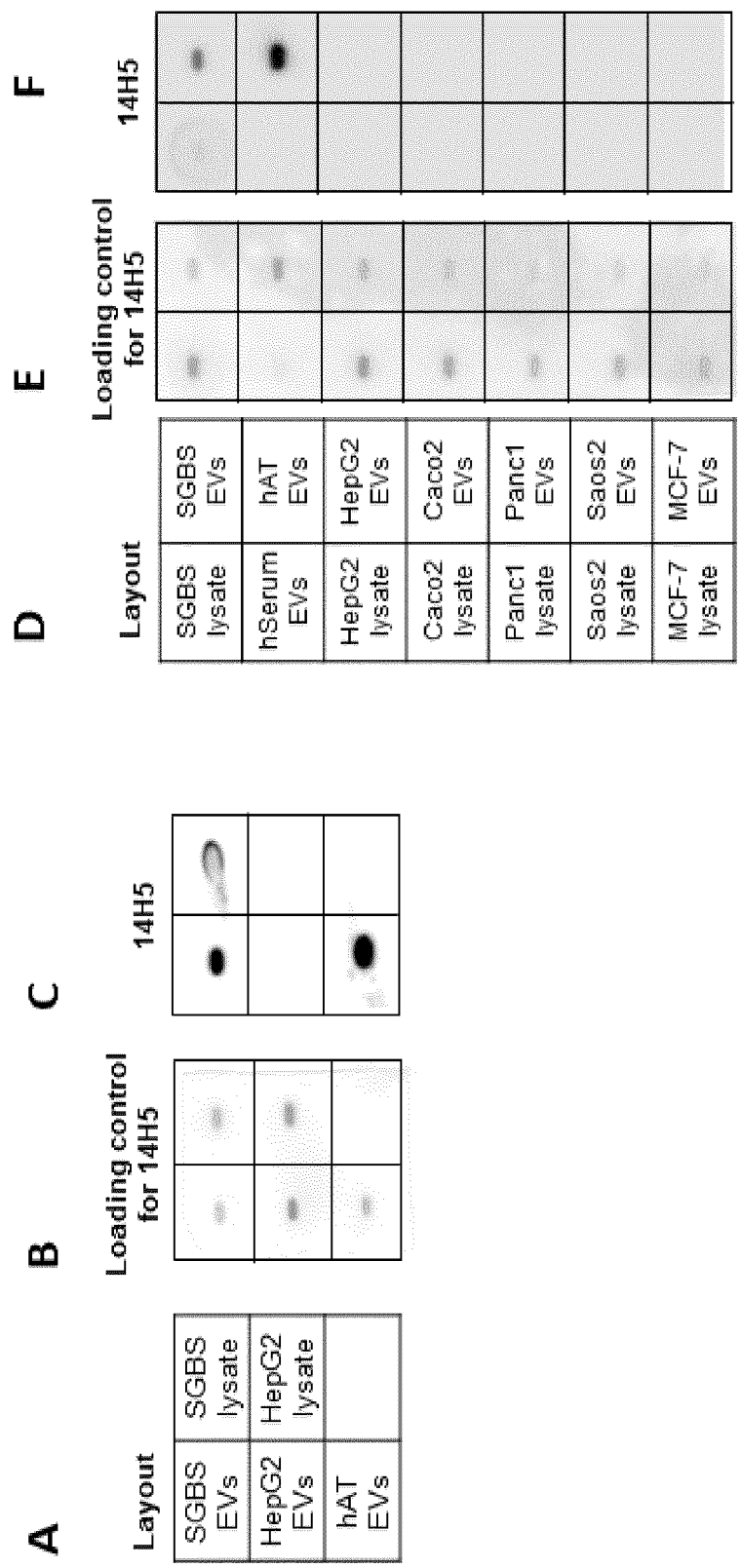

FIG. 19: Antibody characterization for antibody 14H5.

In the following figure, EVs preferably comprise exosomes to the highest amount. (A) and (D) Sample spotting layout of the loading schemes. (B) and (E) The presence of loaded protein prior to antibody staining (loading controls) was proven by Ponceau staining. (C) Spotted membranes incubated with our selected antibody clone 14H5 demonstrating a positive signal in SGBS-EVs (used as antigen for mouse immunization) and SGBS lysates and hAT EVs. No antibody binding was observed for HepG2 lysates or HepG2 EVs. (F) Spotted membranes, incubated with our selected antibody clone 14H5 demonstrating a positive signal in SGBS-EVs (used as antigen for mouse immunization) and SGBS lysates and hAT EVs, but no binding to lysates or EVs from other human non-adipose tissue cell lines.

DETAILED DESCRIPTION

To date, there is still a lack of reliable biomarkers that allow for early prediction or diagnosis of obesity and other metabolic diseases. The present invention provides evidence suggesting that tissue-specific exosomes could represent a solution to that problem. Specifically, an optimized ultracentrifugation protocol to isolate and purify exosomes from the adipocyte fraction of epididymal and subcutaneous fat depots (Example 1.2) was first established. Strikingly, proteome and miRNA signatures of the adipocyte exosomes were reminiscent of the tissue of origin and reflected its metabolic state (Examples 2.3 and 2.4); proving their potential as functional biomarkers—an idea that is corroborated by the finding that exosomal microRNA profiles in obese animals revealed activated inflammation and browning signalling (Example 2.6). In addition, it was shown that adipocyte exosomes are taken up specifically in metabolically active organs such as the pancreas, liver and muscle (Example 2.5). Overall, the present findings suggest that adipocyte exosomes convey directional information transfer between adipose tissue and selected target organs. Moreover, the data presented herein promote a potential role for exosomes as liquid biomarkers for the metabolic and pathophysiological state of preferably adipose tissue.

The present invention provides that tissue-specific exosomes, preferably derived from adipose tissue, more preferably from human adipose tissue, are isolatable by an antibody of the present invention, which is capable of specifically binding to a tissue-specific exosomal surface marker. Therefore, specifically isolating or extracting the tissue-specific exosomes from a sample of a subject to be diagnosed is improved due to the isolation-step using organ-specific antibodies, preferably adipose specific antibodies.

In view of the foregoing, the present invention thus provides tissue-specific exosomes for diagnosing, monitoring and/or predicting the risk for developing a metabolic disease in a subject, wherein said tissue-specific exosomes are isolatable by an antibody capable of specifically binding to a tissue-specific exosomal surface marker, wherein said antibody comprises a) the following $V_H$ and $V_L$ domain CDRs having the amino acid sequence shown in SEQ ID Nos. 1 to 3 and 4 to 6, b) the following $V_H$ and $V_L$ domain CDRs having the amino acid sequence shown in SEQ ID Nos. 7 to 9 and 10 to 12, c) the following $V_H$ and $V_L$ domain CDRs having the amino acid sequence shown in SEQ ID Nos. 13 to 15 and 16 to 18. In this context, the term "diagnosing" as used herein refers to methods by which the skilled person can estimate and/or determine the probability ("a likelihood, "a risk") of whether or not a subject develops a given disease or condition (e.g. metabolic disease) in the presence or whether or not a given disease outbreaks in the presence. In other words, "diagnosing" means that a subject is informed that he/she suffers from a given disease. As used herein, the term "predicting" refers to methods by which the skilled person can estimate and/or determine (or rather forecast) the probability ("a likelihood, "a risk") of whether or not a subject will develop (is going to develop) a given disease or condition (e.g. metabolic disease) in the near future. As used herein, the term "monitoring" refers to methods by which the skilled person can supervise and/or trace the progress of a disease, if the subject is diagnosed with a given disease (e.g. metabolic disease) or it refers to methods by which the skilled person can supervise and/or trace the progress of a risk of a subject, if a risk has been predicted that a subject will develop a given disease (e.g. metabolic disease) in the near future.

Exosomes

Term "exosome" or "exosomes" refers to small membrane-derived extracellular vesicles (EV). The term "extracellular vesicles" comprises of several types of vesicles that differ in their cellular origin, mode of biogenesis, molecular cargo and membrane composition, size and physical properties. Extracellular vesicles are released from many cell types ("producer cells" or "source cell" or "donor cell") including neurons, tumor and immune cells, among others. They can be found in different body fluids such as serum, breast milk, saliva, cerebrospinal fluid, semen, and urine.

Three main types of EVs have been defined: (i) exosomes, (ii) microvesicles (MVs) and (iii) apoptotic bodies. The term "extracellular vesicles (EVs)" is a generic term for all secreted vesicles (e.g. exosomes, MVs and apoptotic bodies). Exosomes are the smallest subgroup of EVs ranging between about 30-120 nm in diameter, i.e. have a diameter of at least 30 nm and 120 nm or less, e.g. 100 nm or less. Exosomes are thought to be derived from the endolysosomal pathway via the fusion of multivesicular bodies (MVB), i.e. large endosomal structures comprising intra-lumenal vesicles, with the plasma membrane and the release of said vesicles into the extracellular space. Unlike exosomes, "microvesicles", also known as ectosomes, shedding vesicles, microparticles, and plasma membrane-derived vesicles, are thought to originate from the plasma membrane by outward budding and fission, where they are released by direct outward budding of the plasma membrane. Their size ranges from 50 nm to 1,000 nm in diameter. The term "exosomes" may encompass both "exosomes" having a diameter of 30-120 nm and "microvesicles" having a diameter of between 50-1000 nm, with exosomes having a diameter of about 30-120 nm and preferably originating from MVB being preferred. Apoptotic bodies are released by fragmentation and blebbing of the plasma membrane. They have a broad size range of 50-2,000 nm and are thought to be a mere side effect of apoptosis. While apoptotic bodies are characterized by phosphatidylserine externalization, no protein markers have been identified that can discriminate between exosomes and MVs. Unlike apoptotic bodies, exosomes and MVs are considered as stable carriers of genetic material, proteins and lipids, which represent the physiological state of the secreting cell. They are released by healthy and diseased cells into bodily fluids and provide a rich source for diagnostic analyses. In the following, the term "EVs" preferably comprises exosomes to the highest amount.

Structurally, exosomes can be described as spherical bilayered proteolipids carrying a cargo of various biomolecules, including genetic material such as mRNA, microRNA (miRNA), and other non-coding RNAs or even small amounts of DNA, lipids and proteins including transcription factors, cytokines, growth factors and others.

The term "lipid" refers to hydrophobic or amphiphilic small molecules and includes fats (triglycerides), monoglycerides, diglycerides, waxes, phosphatides, cerebrosides, fatty acids, steroids, and related and derived compounds.

Lipid components of exosomes include membrane lipids such as sphingomyelin, phosphatidylcholine, phosphatidylethanolamine, phosphatidylserine, ganglioside GM3, and phosphatidylinositol, prostaglandins (E2, F2, J2, and D2), and lysobisphosphatidic acid. In general, exosomes exhibit an overall lipid profile that is enriched in sphingomyelin, cholesterol, GM3, and phosphatidylserine, which allow the tight packing of lipid bilayers, maintain the exosomal structure and increase overall rigidity and stability of the exosomal structure. Specific ratios of these lipids (and also possibly the presence of specific lipids) are thought to vary according to the originating cell—unique lipid profiles are therefore envisaged as potential tools for identifying, isolating, purifying and/or enriching exosomes. Moreover, some lipids or lipid compositions may be indicative for pathological changes occurring during onset or progression of metabolic diseases, and are therefore also potential biomarkers.

Furthermore, in addition to lipids and proteins, exosomes also contain nucleic acids including mRNA, miRNA and a large variety of other small noncoding RNA species, including RNA transcripts overlapping with protein coding regions, repeat sequences, structural RNAs, tRNA, rRNA, vault RNA, Y RNA, and small interfering RNAs (siRNA) as well as mitochondrial DNA, and short DNA sequences of retrotransposons. The term "nucleic acid" as used herein generally comprises polyribonucleotides (RNA) and polydeoxribonucleotides (DNA), each in single-stranded and/or double-stranded form, linear or circular, or mixtures thereof, including hybrid molecules. RNAs include, without limitation, messenger RNAs (mRNA), non-coding (nc-)RNAs (including anti-sense-RNAs, silencer RNAs, micro-RNAs (miRNAs), short hairpin RNAs (shRNAs), small interfering RNAs (siRNAs), repeat-associated small interfering RNA (rasiRNA), piwi-interacting RNAs (piRNA), Y RNA, Long non-coding RNAs (long ncRNAs, lncRNA)), transfer RNAs (tRNA), ribosomal RNAs (rRNA), small nuclear RNA (snRNA), small nucleolar ribonucleic acid (snoRNA), spliced leader RNAs (SL RNA). All of the aforementioned RNAs are in principle conceivable as exosomal constituents and may be utilized within the methods of the present invention.

The exosomal nucleic acid profile is thought to depend not only on the cell or tissue of origin, but also to be indicative of its functional or pathological state. Specifically, the present inventors could demonstrate that obesity was associated with the enrichment of numerous miRNAs with a role in pro- and anti-inflammatory signaling, adipose tissue browning or adipogenesis in adipocyte-derived exosomes. It is therefore envisaged that nucleic acids are particularly useful as biomarkers reflecting the state of the secreting tissue or cell.

Exosomes also comprise proteins and peptides. The terms "polypeptide" and "protein" are used interchangeably herein. The term "polypeptide" refers to a protein or peptide that typically contains or consists of at least 20, and preferably at least 30, such as at least 50 amino acids. The term "peptide" refers to an oligomer containing or consisting of at least 2 amino acids to about 19 amino acids. Accordingly, a polypeptide comprises an amino acid sequence, and, thus, the term "(poly-)peptide sequence" or "protein sequence" is interchangeably used with the term "amino acid sequence". The term "amino acid" or "amino acid residue" typically refers to an amino acid having its art recognized definition such as an amino acid selected from the group consisting of: alanine (Ala or A); arginine (Arg or R); asparagine (Asn or N); aspartic acid (Asp or D); cysteine (Cys or C); glutamine (Gln or Q); glutamic acid (Glu or E); glycine (Gly or G); histidine (His or H); isoleucine (Ile or I): leucine (Leu or L); lysine (Lys or K); methionine (Met or M); phenylalanine (Phe or F); pro line (Pro or P); serine (Ser or S); threonine (Thr or T); tryptophan (Trp or VW); tyrosine (Tyr or Y); and valine (Val or V), although modified, synthetic, or rare amino acids may be used as desired. Generally, amino acids can be grouped as having a nonpolar side chain (e.g., Ala, Ile, Leu, Met, Phe, Pro, Val); a negatively charged side chain (e.g., Asp, Glu); a positively charged sidechain (e.g., Arg, His, Lys); or an uncharged polar side chain (e.g., Asn, Cys, Gin, Gly, Ser, Thr, Trp, and Tyr).

The proteins most frequently identified in exosomes are membrane transporters and fusion proteins (e.g., GTPases such as Rab5, annexins, and flotillin), heat shock proteins (e.g., HSC70), tetraspanins (e.g., CD9, CD63, and CD81), MVB biogenesis proteins (e.g., alix and TSG101), lipid-related proteins and phospholipases, cytoskeleton proteins (actins, cofilin-1, ezrin/radixin/moesin, profilin-1, and tubulins), metabolic enzymes, and ribosomal proteins. Several proteins are recognized as basic exosomal markers, among which the tetraspanins, CD63 and CD81, are the most commonly used. Although the latter are commonly used as markers of exosomes, they are not exclusive to exosomes and may be found on other extracellular vesicles. This also applies for CD9, for which other extracellular vesicles are positive for. Furthermore, not all exosomes express CD63 and different sub-populations of exosomes originating from different tissues or cells may express different markers. Importantly, the aforementioned markers do not allow for specific isolation or enrichment of a given exosomal subpopulations, since CD9, CD63 and CD81 are considered as being basic exosomal markers, which are non-organ specific.

Interestingly, the present inventors found the exosomal composition and in particular proteome being determined largely by (1) the type and (2) state of the secreting tissue, implicating their potential as a "liquid biopsy". These characteristics can be utilized for (1) identification, isolation, purification and/or enrichment of these exosomes and (2) diagnosis, prognosis and monitoring of the disease state of the secreting tissue.

As explained previously, exosomes were found to be abundant in many bodily tissues and fluids, and have been successfully purified using differential ultracentrifugation (Raposo, G. et al. J. Exp. Med. 1996; 183(3):1161-1172). Other studies have also shown that exosomes may be isolated using ultracentrifugation in a continuous density gradient of sucrose (Escola J M et al., J Biol Chem. 1998 Aug. 7; 273(32):20121-7).

Cheruvanky et al. Am J Physiol Renal Physiol. 2007 May; 292(5):F1657-61 have successfully used ultrafiltration and microfiltration, respectively, for rapid isolation of urinary exosomes. Exosomes have also been isolated by immunoaffinity capture methods using lectins or antibodies against exosomal household markers such as CD63, CD81, EpCAM, or Rab5 (Barres C et al., Blood. 2010 Jan. 21; 115(3):696-705 and Chen, Lab Chip. 2010 Feb. 21; 10(4): 505-11).

The present inventors provided an optimized ultracentrifugation protocol for isolating exosomes from adipose tissue (see Example 1.2). However, techniques that allow for specific isolation of exosome subpopulations not only directly from the secreting tissue but also from bodily fluids (i.e. using non-invasive or only minimally invasive procedures) would be highly desirable in order to minimize the risk of complications. As discussed above, exosomal household markers such as CD63, CD81, EpCAM, or Rab5 are only of little avail in this respect, because they are not specific for the secreting tissue and can also be found on other extracellular vesicles.

Exosomal Surface Markers

Based on the finding that exosomes (e.g. derived from adipocytes) carry unique biomolecule signatures indicative of the secreting tissue, the present inventors concluded that exosomal surface markers specific for the tissue of origin must exist, and can be employed for isolation, purification and enrichment of a tissue-specific exosomal subpopulation.

In the appended examples, exosomes are shown to harbor markers that were associated with specific exosomal subpopulations (specifically: adipocyte-derived exosomes) originating from the same tissue. Thus, said exosomes employed in the methods of the invention sharing a common secreting tissue are said to be "tissue-specific". As explained previously, exosomes are formed on a cellular level, and can hence also be referred to as "cell-of-origin-specific" or "cell-specific". For the purposes of this application, the terms "tissue-specific", "cell-specific" and "cell-of-origin-specific" are used interchangeably. A plurality (i.e. at least two or more) of exosomes originating from the same tissue, and thus sharing at least one exosomal marker that allows for their respective attribution, are also referred to as a "(tissue-specific) exosomal subpopulation" herein.

Said marker may in general be any biomolecule or combination thereof unique to a certain exosomal subpopulation, and may in particular be selected from a lipid, a protein or a nucleic acid as described in the foregoing, preferably a protein, more preferably COL6A1/2/3 and/or AOC3, which are the preferred targets for said antibodies of the present invention being capable of specifically binding to tissue-specific EVs. For ease of handling, the methods of the present invention are envisaged to utilize exosomal surface markers for identification, isolation, purification and/or enrichment of tissue-specific exosomes for further diagnosis.

The term "exosomal surface marker" generally refers to any biomolecule or combination of biomolecules present on (and preferably restricted to) a defined exosomal subpopulation (i.e. a plurality of exosomes sharing a common tissue or cell of origin). The exosomal surface marker is thus indicative of the tissue or cell of origin, and may also be referred to as "tissue-specific" or "cell-of-origin specific". In this context, the term "exosomal surface marker" refers to an antigen, which is bound extracellular to the surface of an exosome or which is bound intracellular to the surface of an exosome. Preferably, said antigen (in particular a protein) is bound extracellular to the surface of an exosome."

The exosomal surface marker will preferably allow for isolation, purification and/or enrichment of said exosomal subpopulation, e.g. with the help of binding molecules as described herein. For the purposes of the present invention, the term "isolation" and "isolating" in all their grammatical forms relate to the act of separating or recovering exosomes from their environment, e.g. a serum or plasma sample or a tissue biopsy (optionally in a pre-treated form). The terms "purifying" and "purification" in all their grammatical forms relate to the act of (substantially) freeing the desired exosomes from (non-exosomal) contaminants. The terms "enriching" and "enrichment" in all their grammatical forms mean increasing the proportion of exosomes in their respective solvent(s). The exosomal surface marker preferably comprises an antigenic structure recognized by an antibody of the invention. Proteins are particularly envisaged as exosomal surface markers, but other biomolecules such as lipids are also conceivable. Further information about exosomal surface markers is given in the context of an antibody according to the invention.

It will readily be understood that the exosomal surface marker will preferably not be selected from the exosomal household markers described in the foregoing, as these markers are abundant throughout the body and present on many exosomal subpopulations and other extracellular vesicles, rendering them less suitable for specific isolation of an exosomal subpopulation of a defined origin. That is, the exosomal surface marker employed in the methods of the invention is preferably not selected from heat shock proteins (e.g., HSC70), tetraspanins (e.g., CD9, CD10, CD26, CD53, CD63, CD81, CD82), MVB biogenesis proteins (e.g., alix and TSG101), EpCAM, or Rab5. Generally, surface markers that cannot be attributed to a specific exosomal subpopulation (i.e. used to distinguish one exosomal subpopulation from another) are less preferred for the purposes of the present invention. Methods for isolating tissue-specific exosomes with the help of an exosomal surface marker and preferably an antibody of the invention are described below.

Exosomal Biomarkers

As explained previously, the present inventors discovered that adipocyte-derived exosomes bear a molecular cargo that mirrors not only environmental conditions but also pathological changes in the secreting tissue (see the appended Examples). Having discovered that particularly adipocyte-derived exosome biomolecule signatures depend on and thus mirror the functional state of the secreting cell or tissue (e.g., rested, stimulated, stressed, etc.), the present inventors concluded that tissue-specific exosomes hold considerable potential as biomarkers for diagnosing, prognosing and/or monitoring metabolic diseases.

Unless denoted otherwise, the term "exosomal biomarker" is used herein to refer to exosomal biomolecules indicative for a specific metabolic condition or disease. Said biomarkers can in general be selected from any of the aforementioned exosomal biomolecules that represent the exosomal constituents, i.e. proteins, peptides, nucleic acids or lipids, preferably a protein, more preferably COL6A1/2/3 and/or AOC3. Suitable exosomal biomarkers can be identified by isolating tissue-specific exosomes from the affected tissue of a subject suffering from a metabolic disease (e.g. using binding molecules such as an antibody of the present invention and exosomal surface markers as described herein) for proteome analysis as described in the appended examples. Comparison to exosomes belonging to the same exosomal subpopulation derived from healthy individuals reveals which biomarkers (here: proteins) are indicative for the respective metabolic disease.

Of course, choice of the exosomal subpopulations to be investigated (and, thus, secreting tissue) will depend on the specific metabolic disease and its effects. E.g., it has been shown that adipocyte exosome signatures reflect dietary interventions as well as changes in (membrane) lipid metabolism, inflammation and other pathways involved in diabetic complications and cancer (see the Examples). Adipocyte-derived exosomes are therefore envisaged to hold considerable potential as diagnostic markers of obesity and associated morbidities. Besides white or brown adipose tissue other tissues-of-origin that are envisaged within the context of the present invention may include liver tissue, pancreas tissue, bowel tissue, muscular tissue, stomach tissue, kidney tissue or hypothalamus tissue; i.e. exosomes employed in the methods of the present invention are preferably derived from white adipose tissue and may be isolated by an antibody of the present invention. However, it may be the case that an antibody of the present invention, being highly organ-specific for adipocyte-derived EVs might also slightly bind to EVs from other organs due to cross-reactivity, since it is technically impossible to isolate EVs from all human organs and to identify their bindings.

A list of potential exosomal markers that are considered potentially useful exosomal surface markers (for isolation of exosomes) or biomarkers (for diagnosis), or both, is provided in the following. These markers are particularly envisaged as surface markers of adipocyte-derived exosomes: AC246787.8, AHNAK, AHSG, ALB, ANXA2, AOC2, AOC3, APOB, ATP5A1, AZGP1, C3, CALML5, CAV1, CLUH, COL6A1, COL6A2, COL6A3, DCAF8L1, DDX3Y, DSC1, DSP, EEF1A1, ENO1, ERP44, EWSR1, F2, FAM47E-STBD1, FBLN2, FLG2, GSN, GYG1, HBA2, HELZ2, HNRNPF, HNRNPH1, HSP90AA1, HSP90B1, HSPA5, HSPA8, ITIH2, ITLN1, ITLN2, KRT1, KRT10, KRT14, KRT16, KRT17, KRT2, KRT31, KRT33B, KRT5, KRT6A, KRT6B, KRT6C, KRT86, KRT9, LAMP2, LDHA, LDHB, LGALS1, LGALS3, LGALS3BP, MIF, MTMR14, MVP, MYH10, MYH9, MYL3, MYL6, MYO1C, NYNRIN, OTC, PGP, PICALM, PKM, PLIN1, POSTN, RP11-812E19.9, RPS11, SERPINF1, SERPINH1, TBL1XR1, TLN1, TPM2, TUBA1A, TUBB, VIL1, VIM, VTN, YWHAZ, CD47, SLC5A6, DHCR24, HLA-F, CNTFR, PLIN1.

The exosomal markers COL6A1/2/3 and/or AOC3 are considered as being the preferred exosomal surface markers or biomarkers for said isolated tissue-specific exosomes of the present invention, which according to the methods of the invention are isolatable by an antibody of the present invention, which is capable of specifically binding to said aforementioned tissue-specific exosomal surface marker. The expression of said preferred targets as mentioned above are increased in adipose tissue in comparison to other organs.

Collagen VI is a major structural component of microfibrils. In general, collagens are a superfamily of proteins that play a role in maintaining the integrity of various tissues. Collagens are extracellular matrix proteins and have a triple-helical domain as their common structural element. The basic structural unit of collagen VI is a heterotrimer of the alpha1(VI) (here as COL6A1), alpha2(VI) (here as COL6A2), and alpha3(VI) chains (here as COL6A3). Additionally, each monomer (alpha1, alpha2 and alpha3) of collagen VI is highly expressed in adipocytes. An antibody of the present invention preferably binds to the heterotrimer of COL6A1/2/3. An antibody of the present invention may also bind to COL6A1 and/or COL6A2 and/or COL6A3.

AOC3 (amine oxidase, copper containing 3) is an enzyme that in humans is encoded by the AOC3 gene on chromosome 17. This protein is a member of the semicarbazide-sensitive amine oxidase (SSAO) family. Copper amine oxidases catalyze the oxidative conversion of amines to aldehydes in the presence of copper and quinone cofactor. Alterations in levels of the encoded protein may be associated with many diseases, including diabetes mellitus. It is highly expressed on adipocytes (fat cells).

In general, the means and methods of the present invention are thought to be useful for diagnosis, prediction or monitoring of a variety of metabolic diseases. The term "metabolic disease" is used herein in its broadest sense to refer to a disease, disorder or condition that is caused by an abnormal metabolism. The term comprises congenital metabolic diseases that are due to an inherited enzyme abnormality, and acquired metabolic diseases caused by dysfunction or failure of an endocrine or otherwise metabolic important organ.

It is thus envisaged that the means and methods of the present invention are applicable for diagnosis, prognosis and/or monitoring of obesity, hyperglycaemia, insulin resistance, prediabetes, type 1 or type 2 diabetes, pancreatic hypertrophy, adipose tissue inflammation, adipose tissue browning, fatty liver disease (FLD), glycogen storage disease (GSD), galactosemia, lactose intolerance, fructose intolerance, sucrose intolerance, phenylketonuria (PKU), glutaric aciduria type 1, organic acidemia, lysosomal storage diseases, including lipid storage disorders, mucopolysaccharidoses, mucolipidoses, Systemic primary carnitine deficiency, (SPCD), haemochromatosis, glycoproteinosis and associated co-morbidities, preferably obesity, insulin resistance, prediabetes, and type 1 or type 2 diabetes.

E.g., adipocyte-derived exosomes are thought to be particularly useful for identifying or predicting metabolic diseases related to or caused by abnormal triacylglycerol storage driven by excess energy intake and insufficient energy expenditure, insulin resistance, and obesity, and accompanied or followed by considerable reduction in the number and function of pancreatic 3-cells. Said diseases particularly include obesity, insulin resistance, metabolic syndrome, prediabetes, and diabetes.

"Obesity" is defined as abnormal or excessive fat accumulation that presents a risk to health. A common measure of obesity is the body mass index (BMI), a person's weight (in kilograms) divided by the square of his or her height (in metres). A person with a BMI of 30 or more is considered obese (WHO: Waist circumference and waist-hip ratio: report of a WHO expert consultation, Geneva, 8-11 Dec.

2008). Another measurement of obesity is the waist-hip ratio or waist-to-hip ratio (WHR), i.e. the ratio of the circumference of the waist to that of the hips. According to the WHO, abdominal obesity is defined as a waist-hip ratio above 0.90 for males and above 0.85 for females (WHO: supra).

"Metabolic syndrome" (also known as metabolic syndrome X, cardiometabolic syndrome, syndrome X, insulin resistance syndrome, Reaven's syndrome, CHAOS) is a cluster of (at least three of the following) risk factors that is associated with cardiovascular diseases and diabetes. Risk factors include: abdominal (central), elevated blood pressure, elevated fasting plasma glucose, high serum triglycerides, and low high-density lipoprotein (HDL) levels. "Prediabetes" is characterized by elevated blood glucose levels not high enough to be classified as type 2 diabetes. Without intervention, prediabetes is likely to become type 2 diabetes in 10 years or less. "Insulin resistance" as a condition characterized by the desensitization and consequent failure of target cells to respond to insulin, leading to hyperglycemia.

The term "diabetes" generally includes type 1 and type 2 diabetes. Type 1 diabetes is also known as Insulin Dependent Diabetes Mellitus (IDDM), and juvenile diabetes. The terms are used interchangeably herein. This form accounts for 5-10% of diabetes and is thought to be due to cellular-mediated autoimmune destruction of the pancreatic β-cells, resulting in little or no insulin secretion. It is envisaged that tissue-specific exosomes (e.g. released from pancreatic 3-cells) can be isolated from bodily fluids employing the binding molecules provided herein and be used as early biomarkers for predicting or detecting disease onset, preferably before an irreversible destruction of β-cells occurs. Type 2 diabetes is also referred to as adult-onset diabetes and accounts for ~90-95% of all diabetes. Insulin resistance in target tissues and a relative deficiency of insulin secretion from pancreatic β-cells are the major features of type 2 diabetes (T2D). Pancreatic β cells in the pancreas subsequently increase their production of insulin, leading to hyperinsulinemia and later β-cell damage. Tissue-specific exosomes are envisaged to be useful biomarkers for predicting or early indicating loss-of-function in pancreatic β cells, and/or the loss of insulin sensitivity in target tissues.

It is also envisaged that the methods and uses of the present invention can be employed for diagnosing, monitoring and in particular predicting related co-morbidities of metabolic diseases, including particularly non-alcoholic fatty liver disease (NAFLD), (cardio-) vascular disease (including arteriosclerosis, myocardial infarction, stroke, congestive heart failure, coronary artery disease, microvascular disease including retinopathy, nephropathy, and neuropathy and peripheral vascular disease), hypertension, dyslipidemia, sleep apnea, arthritis, hyperuricemia, gall bladder disease, and/or cancer.

All of the aforementioned conditions, diseases and morbidities are thought to be reflected by the specific biomolecule signature of the exosomes released from affected tissues, which can thus be employed to obtain valuable information about disease state and/or progression in a non-invasive or minimally invasive manner.

Isolation of Exosomes

Tissue-specific exosomes as described herein can be obtained or isolated from a sample of the subject, which is to be diagnosed with a metabolic disease, or whose metabolic disease is to be monitored or predicted. Generally, exosomes can be directly assayed from the biological samples, such that the level of exosomes is determined or the one or more biomarkers of the exosomes are determined without prior isolation, purification, or enrichment of the exosomes. Alternatively, exosomes may be isolated or enriched from a sample prior to analysis.

In the appended Examples, a novel optimized protocol for isolating exosomes from adipose tissue is provided which utilizes ultracentrifugation. Said method (and related protocols for obtaining exosomes from tissue samples) is in principle applicable for the methods of the present invention. I.e., exosomes can be isolated from a sample or biopsy of the affected tissue. Typically, however, analysis will require pre-treatment of the tissue sample or biopsy, e.g. using centrifugation and/or filtering steps and treatment with specific buffers, enzymes or the like. Subsequently, exosomes can be either isolated from the (optionally pre-treated) sample (e.g. by utilizing an antibody of the present invention capable of binding to exosomal surface markers as described herein) prior to further analysis or be analyzed directly from the (optionally pre-treated) sample (e.g. by determining the presence or absence of one or more exosomal biomarkers as described herein).

However, as non- or minimally invasive procedures are often preferred for diagnosis (in order to reduce the risk of complications and increase patient compliance), the present invention also provides for means and methods for isolating exosomes from bodily fluids, exploiting the fact that exosomes carry unique surface markers that allow for specific "capturing" of a desired exosomal subpopulation from the sample fluid preferably using an antibody of the present invention.

The sample obtained from the subject to be diagnosed is selected from a blood sample, a plasma sample, a serum sample, lymph, saliva, bile, feces, breast milk, urine sample, cerebrospinal fluid sample, amniotic fluid, or an organ or tissue biopsy.

For many diseases such as cancer, non-alcoholic fatty liver disease (NASH), muscle atrophy, or amyloidosis invasive tissue biopsies followed by histopathological or molecular analysis are considered as diagnostic gold standard. Regardless of whether such procedures are performed as highly invasive surgeries or as less invasive needle punctures, tissue biopsies carry the risk of infection and cannot be applied repeatedly. Accordingly, disease progression and therapeutic responses cannot be monitored in detail. Moreover, core and needle biopsies often do not result in sufficient amounts of tissue for in depths diagnostic analyses and can even miss zonal pathophysiological tissue alterations. Because blood samples can be easily and repeatedly obtained, the concept of "liquid biopsies" has held promise as a less invasive complement to traditional tissue biopsies. Upon secretion into bodily fluids, EVs can be isolated via ultracentrifugation from said liquid biopsies.

The sample obtained from the subject to be diagnosed is thus preferably envisaged to be a bodily fluid for liquid biopsies, such as peripheral blood, serum, plasma, ascites, urine, cerebrospinal fluid (CSF), sputum, saliva, bone marrow, synovial fluid, aqueous humor, amniotic fluid, broncheoalveolar lavage fluid, cyst fluid, pleural and peritoneal fluid, pericardial fluid, lymph, chyme, chyle, bile, interstitial fluid, menses, mucosal secretion, pancreatic juice, lavage fluids from sinus cavities, bronchopulmonary aspirates or other lavage fluids, the blastocoel, umbilical cord blood, breast milk, or feces, preferably a blood sample, more preferably a serum sample from blood.

Since, "liquid biopsies" promise as a less invasive complement to traditional tissue biopsies as mentioned above and EVs are released by healthy and diseased cells into bodily fluids, they may also represent the physiological state of the secreting cell as it is shown for tissue samples. To test and verify this, the proteome of EVs being IP-isolated from the blood stream, preferably from blood serum, may have very similar protein profiles when compared to EVs being directly isolated from adipose tissue (AT) samples of the same patients. Thus, an antibody of the present invention may bind to tissue-specific EVs, preferably to adipose derived EVs obtained from tissue biopsy as well as from liquid biopsy, in particular from serum sample, which are considered as being the preferred samples.

The terms "subject", "patient" and "individual" are used interchangeably herein to refer to a mammal, in particular a human, non-human primate, dog, cat, guinea pig, rabbit, rat or mouse.

As described above in the context of tissue samples and liquid biopsies, exosomes can be either isolated from the (optionally pre-treated) sample (e.g. by utilizing exosomal surface markers which are bound by an antibody of the present invention as described herein) prior to further analysis or be analyzed directly from the (optionally pre-treated) sample (e.g. by determining the presence or absence of one or more exosomal biomarkers as described herein). "Analysis" may, in general, include quantification of the amount exosomes in a sample and/or assessing the presence or absence of one or more exosomal biomarkers indicative for a metabolic disease.

In order to isolate exosomes from the sample, it is envisaged to bring the sample into contact with an antibody of the present invention capable of specifically binding to said exosomes, and in particular to an exosomal surface marker as described elsewhere herein. After contacting a sample containing or suspected of containing said exosomes with at least one antibody of the present invention that specifically binds to an exosomal surface marker, a signal can be generated that is indicative of the binding of said antibody of the present invention to its specific target (i.e. the exosomal surface marker). The signal is then typically related to the presence or amount of the exosomal surface marker in the sample. Various assay devices and methods utilizing labeled binding molecules in various sandwich, competitive, or non-competitive assay formats to generate a signal are known in the art. Suitable assay formats also include chromatographic, mass spectrographic, and protein "blotting" methods. Additionally, certain methods and devices, such as biosensors and optical immunoassays, may be employed to determine the presence or amount of analytes without the need for a labeled molecule. The aforementioned assays often require labeling and/or immobilization of the "capturing" antibody of the present invention used for exosome isolation on a solid support, as described elsewhere herein.

Exosome Specific Antibody

The development of an antibody-based strategy including an antibody of the present invention enables the sorting and extracting of tissue-specific EVs from a sample of a subject to be diagnosed.

As mentioned above, an antibody of the present invention is capable of specifically binding to a tissue-specific exosome, in particular to a tissue-specific exosomal surface marker on said tissue-specific exosome, wherein (i) said antibody comprises a) the following $V_H$ and $V_L$ domain CDRs having the amino acid sequence shown in SEQ ID Nos. 1 to 3 and 4 to 6, b) the following $V_H$ and $V_L$ domain CDRs having the amino acid sequence shown in SEQ ID Nos. 7 to 9 and 10 to 12, c) the following $V_H$ and $V_L$ domain CDRs having the amino acid sequence shown in SEQ ID Nos. 13 to 15 and 16 to 18, or wherein (ii) said antibody competes for the same epitope as that recognized by the antibody of (i) and wherein the antibody can block the binding of the antibody of (i) by at least 20% compared with the affinity obtained in a control test performed in the absence of the competing antibody.

The application of an antibody of the present invention allows for isolation, purification and/or enrichment of a tissue-specific exosomal subpopulation.

The present inventors successfully generated and characterized a panel of antibodies, which refer to an antibody of the present invention. In particular three antibodies were generated that specifically bind to human adipose tissue (AT) derived EVs, and that could preferably be suitable to generate liquid AT biopsies. These three antibodies belong to the antibody producing clones 23A11, 15G1 and 14H5. The antibody 23A11, 15G1 and 14H5 refer to monoclonal antibodies, which are stably established and obtained from rat. Their respective antigens have been successfully characterized via mass spectrometry.

Further, the present invention provides an antibody referring to antibody 23A11 (antibody subclass rat IgG2a) having the amino acid sequence shown in SEQ ID NO. 19 and 20. Here, SEQ ID NO. 19 refers to the $V_H$ domain, whereas SEQ ID NO. 20 refers to the $V_L$ domain of said antibody of the present invention. Further, an antibody of the present invention consists of two $V_H$ domains, which refer to SEQ ID NO. 19 and two $V_L$ domains, which refer to SEQ ID NO. 20. The present invention may also comprise an antibody comprising polypeptide chains, wherein each of the polypeptide chain may have at least 50% sequence identity to SEQ ID No. 19 and/or 20. An antibody of the present invention may comprise polypeptide chains, wherein each of the polypeptide chain may have at least 50%, 55%, 60%, 65%, 70%, 75%, 80%, 85%, 90%, 95%, 96%, 97%, 98%, or at least 99% sequence identity to SEQ ID No. 19 and/or 20. The present invention may also comprise an antibody, wherein the $V_H$ domain CDR1 capable of binding to COL6A1/2/3 may have 1, 2, or 3 mutations as compared to SEQ ID No. 1. Further, the present invention may comprise an antibody, wherein the $V_H$ domain CDR2 capable of binding to COL6A1/2/3 may have 1, 2, 3, or 4 mutations as compared to SEQ ID No. 2. Additionally, the invention may contemplate an antibody, wherein the $V_H$ domain CDR3 capable of binding to COL6A1/2/3 may have 1, 2, 3, 4, 5, or 6 mutations as compared to SEQ ID No. 3. Further, the present invention may envisage an antibody, wherein the $V_H$ domain framework region 1 may have 1, 2, 3, 4, 5, 6, 7, 8, 9, 10, 11 or 12 mutations compared to framework region 1 of SEQ ID No. 25. Further, the present invention may envisage an antibody, wherein the $V_H$ domain framework region 2 may have 1, 2, 3, 4, 5, 6, 7, 8, or 9 mutations compared to framework region 2 of SEQ ID No. 26. Additionally, the present invention may envisage an antibody, wherein the $V_H$ domain framework region 3 may have 1, 2, 3, 4, 5, 6, 7, 8, 9, 10, 11, 12, 13, 14, 15, 16, 17, 18, 19, or 20 mutations compared to framework region 3 of SEQ ID No. 27. The present invention may envisage an antibody, wherein the $V_H$ domain framework region 4 may have 1, 2, 3, 4, or 5 mutations compared to framework region 4 of SEQ ID No. 28. The present invention may also envisage an antibody, wherein the $V_L$ domain CDR1 capable of binding to COL6A1/2/3 may have 1, 2, 3, 4, 5, 6, 7, or 8 mutations as compared to SEQ ID No. 4. The present invention may include an antibody having 1, 2, or 3 mutations in the $V_L$ domain CDR2 capable of binding to COL6A1/2/3 as compared to SEQ ID No. 5. The invention may also encompass an antibody having 1, 2, 3, or 4 mutations in the $V_L$ domain CDR3 capable of binding to COL6A1/2/3 as compared to SEQ ID No. 6. Further, the present invention may envisage an antibody, wherein the V$_L$ domain framework region 1 may have 1, 2, 3, 4, 5, 6, 7, 8, 9, 10, or 11 mutations compared to framework region 1 of SEQ ID No. 29. Further, the present invention may envisage an antibody, wherein the V$_L$ domain framework region 2 may have 1, 2, 3, 4, 5, 6, or 7 mutations compared to framework region 2 of SEQ ID No. 30. Additionally, the present invention may envisage an antibody, wherein the V$_L$ domain framework region 3 may have 1, 2, 3, 4, 5, 6, 7, 8, 9, 10, 11, 12, 13, 14, 15, or 16 mutations compared to framework region 3 of SEQ ID No. 31. The present invention may envisage an antibody, wherein the V$_L$ domain framework region 4 may have 1, 2, 3, 4, or 5 mutations compared to framework region 4 of SEQ ID No. 32.

Further, the present invention provides an antibody referring to antibody 15G1 (antibody subclass rat IgG2a) having the amino acid sequence shown in SEQ ID NO. 21 and 22. Here, SEQ ID NO. 21 refers to the V$_H$ domain, whereas SEQ ID NO. 22 refers to the V$_L$ domain of said antibody of the present invention. Further, an antibody of the present invention consists of two V$_H$ domains, which refer to SEQ ID NO. 21 and two V$_L$ domains, which refer to SEQ ID NO. 22. The present invention may also comprise an antibody comprising polypeptide chains, wherein each of the polypeptide chains may have at least 50% sequence identity to SEQ ID No. 21 and/or 22. An antibody of the present invention may comprise polypeptide chains, wherein each of the polypeptide chain may have at least 50%, 55%, 60%, 65%, 70%, 75%, 80%, 85%, 90%, 95%, 96%, 97%, 98%, or at least 99% sequence identity to SEQ ID No. 21 and/or 22. The present invention may also comprise an antibody, wherein the V$_H$ domain CDR1 capable of binding to AOC3 may have 1, 2, or 3 mutations as compared to SEQ ID No. 7. Further, the present invention may comprise an antibody, wherein the V$_H$ domain CDR2 capable of binding to AOC3 may have 1, 2, 3, or 4 mutations as compared to SEQ ID No. 8. Additionally, the invention may contemplate an antibody, wherein the V$_H$ domain CDR3 capable of binding to AOC3 may have 1, 2, 3, or 4 mutations as compared to SEQ ID No. 9 Further, the present invention may envisage an antibody, wherein the V$_H$ domain framework region 1 may have 1, 2, 3, 4, 5, 6, 7, 8, 9, 10, 11 or 12 mutations compared to framework region 1 of SEQ ID No. 33. Further, the present invention may envisage an antibody, wherein the V$_H$ domain framework region 2 may have 1, 2, 3, 4, 5, 6, 7, 8, or 9 mutations compared to framework region 2 of SEQ ID No. 34. Additionally, the present invention may envisage an antibody, wherein the V$_H$ domain framework region 3 may have 1, 2, 3, 4, 5, 6, 7, 8, 9, 10, 11, 12, 13, 14, 15, 16, 17, 18, 19, or 20 mutations compared to framework region 3 of SEQ ID No. 35. The present invention may envisage an antibody, wherein the V$_H$ domain framework region 4 may have 1, 2, 3, 4, or 5 mutations compared to framework region 4 of SEQ ID No. 36. The present invention may also envisage an antibody, wherein the V$_L$ domain CDR1 capable of binding to AOC3 may have 1, 2, 3, 4, or 5 mutations as compared to SEQ ID No. 10. The present invention may include an antibody having 1, 2, or 3 mutations in the V$_L$ domain CDR2 capable of binding to AOC3 as compared to SEQ ID No.11. The present invention may also encompass an antibody having 1, 2, 3, or 4 mutations in the V$_L$ domain CDR3 capable of binding to AOC3 as compared to SEQ ID No. 12. Further, the present invention may envisage an antibody, wherein the V$_H$ domain framework region 1 may have 1, 2, 3, 4, 5, 6, 7, 8, 9, 10, or 11 mutations compared to framework region 1 of SEQ ID No. 37. Further, the present invention may envisage an antibody, wherein the V$_L$ domain framework region 2 may have 1, 2, 3, 4, 5, 6, or 7 mutations compared to framework region 2 of SEQ ID No. 38. Additionally, the present invention may envisage an antibody, wherein the V$_L$ domain framework region 3 may have 1, 2, 3, 4, 5, 6, 7, 8, 9, 10, 11, 12, 13, 14, 15, or 16 mutations compared to framework region 3 of SEQ ID No. 39. The present invention may envisage an antibody, wherein the V$_L$ domain framework region 4 may have 1, 2, 3, 4, or 5 mutations compared to framework region 4 of SEQ ID No. 40.

The present invention usually envisages an antibody referring to antibody 14H5 (antibody subclass rat IgG2b) having the amino acid sequence shown in SEQ ID NO. 23 and 24. Here, SEQ ID NO. 23 refers to the V$_H$ domain, whereas SEQ ID NO. 24 refers to the V$_L$ domain of said antibody of the present invention. Further, an antibody of the present invention consists of two V$_H$ domains, which refer to SEQ ID NO. 23 and two V$_L$ domains, which refer to SEQ ID NO. 24. The present invention may also comprise an antibody comprising polypeptide chains, wherein each of the polypeptide chain may have at least 50% sequence identity to SEQ ID No. 23 and/or 24. An antibody of the present invention may comprise polypeptide chains, wherein each of the polypeptide chain may have at least 50%, 55%, 60%, 65%, 70%, 75%, 80%, 85%, 90%, 95%, 96%, 97%, 98%, or at least 99% sequence identity to SEQ ID No. 23 and/or 24. The present invention may also comprise an antibody, wherein the V$_H$ domain CDR1 capable of binding to AOC3 may have 1, 2, or 3 mutations as compared to SEQ ID No. 13. Further, the present invention may comprise an antibody, wherein the V$_H$ domain CDR2 capable of binding to AOC3 may have 1, 2, or 3 mutations as compared to SEQ ID No. 14. Additionally, the invention may contemplate an antibody, wherein the V$_H$ domain CDR3 capable of binding to AOC3 may have 1, 2, 3, or 4 mutations as compared to SEQ ID No. 15. Further, the present invention may envisage an antibody, wherein the V$_H$ domain framework region 1 may have 1, 2, 3, 4, 5, 6, 7, 8, 9, 10, 11 or 12 mutations compared to framework region 1 of SEQ ID No. 41. Further, the present invention may envisage an antibody, wherein the V$_H$ domain framework region 2 may have 1, 2, 3, 4, 5, 6, 7, 8, or 9 mutations compared to framework region 2 of SEQ ID No. 42. Additionally, the present invention may envisage an antibody, wherein the V$_H$ domain framework region 3 may have 1, 2, 3, 4, 5, 6, 7, 8, 9, 10, 11, 12, 13, 14, 15, 16, 17, 18, 19, or 20 mutations compared to framework region 3 of SEQ ID No. 43. The present invention may envisage an antibody, wherein the V$_H$ domain framework region 4 may have 1, 2, 3, 4, or 5 mutations compared to framework region 4 of SEQ ID No. 44. The present invention may also envisage an antibody, wherein the V$_L$ domain CDR1 capable of binding to AOC3 may have 1, 2, 3, 4, or 5 mutations as compared to SEQ ID No. 16. The present invention may include an antibody having 1, 2, or 3 mutations in the V$_L$ domain CDR2 capable of binding to AOC3 as compared to SEQ ID No. 17. The present invention may also encompass an antibody having 1, 2, 3, or 4 mutations in the V$_L$ domain CDR3 capable of binding to AOC3 as compared to SEQ ID No. 18. Further, the present invention may envisage an antibody, wherein the V$_L$ domain framework region 1 may have 1, 2, 3, 4, 5, 6, 7, 8, 9, 10, or 11 mutations compared to framework region 1 of SEQ ID No. 45. Further, the present invention may envisage an antibody, wherein the V$_L$ domain framework region 2 may have 1, 2, 3, 4, 5, 6, or 7 mutations compared to framework region 2 of SEQ ID No. 46. Additionally, the present invention may envisage an antibody, wherein the $V_L$ domain framework region 3 may have 1, 2, 3, 4, 5, 6, 7, 8, 9, 10, 11, 12, 13, 14, 15, or 16 mutations compared to framework region 3 of SEQ ID No. 47. The present invention may envisage an antibody, wherein the $V_L$ domain framework region 4 may have 1, 2, 3, 4, 5, or 6 mutations compared to framework region 4 of SEQ ID No. 48.

The CDRs of the $V_H$ and $V_L$ domains of the antibody 23A11 of the present invention may be capable of binding to the heterotrimer COL6A1/2/3. Thus, an antibody of the present invention may comprise $V_H$ and $V_L$ domains preferably binding to heterotrimer COL6A1/2/3. An antibody of the present invention referring to antibody 23A11 may comprise the following $V_H$ and $V_L$ domain CDRs having the amino acid sequence shown in SEQ ID Nos. 1-6, which preferably confer binding to heterotrimer COL6A1/2/3. SEQ ID Nos. 1-3 may refer to the $V_H$ domain CDRs, whereas SEQ ID Nos. 4-6 may refer to the $V_L$ domain CDRs:

SEQ ID No. 1:
Gly Phe Thr Phe Thr Asp Phe (CDR1 in the $V_H$ domain of the COL6A1/2/3 binding site), SEQ ID No. 2:
Arg Asn Lys Ala Asn Gly Tyr Thr (CDR2 in the $V_H$ domain of the COL6A1/2/3 binding site), SEQ ID No. 3:
Gly Gly Phe Asp Val Tyr Ser Gly Leu Leu Pro Asp Tyr (CDR3 in the $V_H$ domain of the COL6A1/2/3 binding site).

SEQ ID No. 4:
Lys Ser Ser Gln Asn Leu Leu Tyr Arg Gly Asn Gln Lys Asn Tyr Leu Ala (CDR1 in the $V_L$ domain of the COL6A1/2/3 binding site), SEQ ID No. 5:
Trp Thr Ser Thr Arg Gln Pro (CDR2 in the $V_L$ domain of the COL6A1/2/3 binding site), SEQ ID No. 6:
Gln Gln Tyr Tyr Gly Thr Pro Phe Thr (CDR3 in the $V_L$ domain of the COL6A1/2/3 binding site).

The CDRs of the $V_H$ and $V_L$ domains of the antibody 15G1 and 14H5 of the present invention may be capable of binding to AOC3. Thus, an antibody of the present invention may comprise CDRs of the $V_H$ and $V_L$ domains preferably binding to AOC3. An antibody of the present invention referring to antibody 15G1 may comprise the following $V_H$ and $V_L$ domain CDRs having the amino acid sequence shown in SEQ ID Nos. 7-12, which preferably confer binding to AOC3. SEQ ID Nos. 7-9 may refer to the $V_H$ domain CDRs, whereas SEQ ID Nos. 10-12 may refer to the $V_L$ domain CDRs:

SEQ ID No. 7:
Gly Phe Asn Phe Asn Asp Tyr (CDR1 in the $V_H$ domain of the AOC3 binding site), SEQ ID No. 8:
Arg Asn Lys His Tyr Asn Tyr Ala (CDR2 in the $V_H$ domain of the AOC3 binding site), SEQ ID No. 9:
Ser Ser Tyr Leu Arg Tyr Phe Asp Phe (CDR3 in the $V_H$ domain of the AOC3 binding site).

SEQ ID No. 10:
Gln Ala Ser Gln Asp Ile Gly Asn Trp Leu Ala (CDR1 in the $V_L$ domain of the AOC3 binding site), SEQ ID No. 11:
Asp Ala Thr Thr Leu Ala Asp (CDR2 in the $V_L$ domain of the AOC3 binding site), SEQ ID No. 12:
Gln Gln Ala Ser Ser Ala Pro Trp Thr (CDR3 in the $V_L$ domain of the AOC3 binding site).

An antibody of the present invention referring to antibody 14H5 may comprise the following $V_H$ and $V_L$ domain CDRs having the amino acid sequence shown in SEQ ID Nos. 13-18, which preferably confer binding to AOC3. SEQ ID Nos. 13-15 may refer to the $V_H$ domain CDRs, whereas SEQ ID Nos. 16-18 may refer to the $V_L$ domain CDRs:

SEQ ID No. 13:
Gly Phe Thr Phe Thr Gly Tyr (CDR1 in the $V_H$ domain of the AOC3 binding site), SEQ ID No. 14:
Asn Thr Gly Ser Gly Gly (CDR2 in the $V_H$ domain of the AOC3 binding site), SEQ ID No. 15:
Thr Tyr Trp Arg Arg Tyr Phe Asp Tyr (CDR3 in the $V_H$ domain of the AOC3 binding site).

SEQ ID No. 16:
Gln Ala Ser Gln Asp Ile Gly Asn Trp Leu Ala (CDR1 in the $V_L$ domain of the AOC3 binding site), SEQ ID No. 17:
Gly Ala Thr Ser Leu Ala Asp (CDR2 in the $V_L$ domain of the AOC3 binding site), SEQ ID No. 18:
Gln Gln Ala Ser Ser Ala Pro Leu Thr (CDR3 in the $V_L$ domain of the AOC3 binding site).

The term "$V_H$ and $V_L$ domain" may refer to the variable domain of the heavy chain and the variable domain of the light chain of the $F_{ab}$ region of an antibody of the present invention. Each $V_H$ domain and each $V_L$ domain of an antibody of the present invention comprises three CDR regions, four framework regions and one signal peptide region. In this context, the term "$F_{ab}$ region" refers to the fragment, antigen-binding region consisting one complete light chain and the variable and $C_H1$ domain of one heavy chain. However, the $F_{ab}$ region can also be divided into the variable fragment ($F_v$) composed of the $V_H$ and $V_L$ domains, and a constant fragment ($F_b$) composed of the constant domain of the light chain ($C_L$) and the $C_H1$ domain. In this context, the term "signal peptide region" refers to the first 19 amino acids of the variable domain of the heavy chain of an antibody of the present invention and/or the first 20 amino acids of the variable domain of the light chain of an antibody of the present invention. In particular, an antibody of the present invention may comprise the following signal peptide region of the $V_H$ domain (SEQ ID No. 19) having the amino acid sequence comprising Met Lys Leu Trp Leu Asn Trp Ile Phe Leu Leu Thr Leu Leu Asn Gly Ile Gln Cys and/or comprise the following signal peptide region of the $V_L$ domain (SEQ ID No. 20) having the amino acid sequence comprising Met Glu Ser Gln Thr Gln Val Leu Met Ser Leu Leu Leu Trp Ile Ser Gly Thr Cys Gly. Further, an antibody of the present invention may comprise the following signal peptide region of the $V_H$ domain (SEQ ID No. 21) having the amino acid sequence comprising Met Lys Leu Trp Leu Ser Trp Ile Phe Leu Val Val Leu Phe Lys Gly Val Arg Cys and/or comprise the following signal peptide region of the $V_L$ domain (SEQ ID No. 22) having the amino acid sequence comprising Met Asn Val Pro Thr Gin Leu Leu Gly Leu Leu Ile Leu Trp Leu Thr Gly Gly Lys Cys. Further, an antibody of the present invention may comprise the following signal peptide region of the $V_H$ domain (SEQ ID No. 23) having the amino acid sequence comprising Met Glu Trp Asn Trp Val Phe Leu Phe Leu Leu Ser Val Thr Ala Glu Val His Ser and/or comprise the following signal peptide region of the $V_L$ domain (SEQ ID No. 24) having the amino acid sequence comprising Met Asn Val Pro Thr Gin Leu Leu Gly Leu Leu Ile Leu Trp Leu Thr Gly Gly Lys Cys.

The term "mutation" refers to substitution, insertion and/or deletion. Mutations may occur in the $V_H$ and $V_L$ domain CDRs and/or in the corresponding frame work region of the $V_H$ and $V_L$ domains of an antibody of the present invention. The term "mutation" may be used interchangeably with the term "modification".

The term "framework region (FR)" refers to the amino acid region before and after a CDR and inbetween CDRs either in the $V_H$ and $V_L$ domain of an antibody of the present invention.

The term "CDRs" refers to complementarity-determining regions, which refer to variable loops of β-strands, three each on the variable domains of the light ($V_L$) and heavy ($V_H$) chains in immunoglobulins (antibodies) generated by B-cells respectively or in single chain $F_v$ regions coupled to an immunoglobulin being responsible for binding to the antigen. Unless otherwise indicated CDRs sequences of the disclosure follow the definition by Maass 2007 (Journal of Immunological Methods 324 (2007) 13-25. Other standards for defining CDRs exist as well, such as the definition according to Kabat CDRs, as described in Sequences of Proteins of immunological Interest, US Department of Health and Human Services (1991), eds. Kabat et al. Another standard for characterizing the antigen binding site is to refer to the hypervariable loops as described by Chothia (see, e.g., Chothia, et al. (1992); J. Mol. Biol. 227:799-817; and Tomlinson et al. (1995) EMBO J. 14:4628-4638). Still another standard is the AbM definition used by Oxford Molecular's AbM antibody modelling software. See, generally, e.g., Protein Sequence and Structure Analysis of Antibody Variable Domains. In: Antibody Engineering Lab Manual (Ed.: Duebel, S. and Kontermann, R., Springer-Verlag, Heidelberg). It is understood that embodiments described with respect to the CDR definition of Maass, can alternatively be implemented using similar described relationships such as with respect to Kabat CDRs, Chothia hypervariable loops or to the AbM-defined loops. In the present invention the CDRs sequences follow the definition of Chothia.

Whether an antibody to be tested recognizes the same epitope as that recognized by a certain antibody, which comprises a) the following $V_H$ and $V_L$ domain CDRs having the amino acid sequence shown in SEQ ID Nos. 1 to 3 and 4 to 6, b) the following $V_H$ and $V_L$ domain CDRs having the amino acid sequence shown in SEQ ID Nos. 7 to 9 and 10 to 12, c) the following $V_H$ and $V_L$ domain CDRs having the amino acid sequence shown in SEQ ID Nos. 13 to 15 and 16 to 18, can be confirmed based on their competition for the same epitope. The competition between the antibodies is detected by cross-blocking assay or the like. For example, competitive ELISA assay is a preferable cross-blocking assay. Specifically, in the cross-blocking assay, a certain target protein (f. e. COL6A1 and/or COL6A2 and/or COL6A3 or AOC3) coated on the wells of a microtiter plate are pre-incubated in the presence or absence of a competing antibody, and an antibody of the present invention, which comprises a) the following $V_H$ and $V_L$ domain CDRs having the amino acid sequence shown in SEQ ID Nos. 1 to 3 and 4 to 6, b) the following $V_H$ and $V_L$ domain CDRs having the amino acid sequence shown in SEQ ID Nos. 7 to 9 and 10 to 12, c) the following $V_H$ and $V_L$ domain CDRs having the amino acid sequence shown in SEQ ID Nos. 13 to 15 and 16 to 18 is then added to the wells. The amount of an antibody of the present invention, which comprises a) the following $V_H$ and $V_L$ domain CDRs having the amino acid sequence shown in SEQ ID Nos. 1 to 3 and 4 to 6, b) the following $V_H$ and $V_L$ domain CDRs having the amino acid sequence shown in SEQ ID Nos. 7 to 9 and 10 to 12, c) the following $V_H$ and $V_L$ domain CDRs having the amino acid sequence shown in SEQ ID Nos. 13 to 15 and 16 to 18 bound to the target protein as mentioned above in the well indirectly correlates with the binding ability of the competing antibody (antibody to be tested) that competes therewith for the binding to the same epitope. Specifically, the larger affinity the antibody to be tested has for the same epitope, the smaller amount of an antibody of the present invention is bound to the target protein-coated well while the larger amount of the antibody to be tested is bound to the target protein-coated well.

The amount of the antibody bound to the well can be measured easily by labeling the antibody in advance. For example, a biotin-labeled antibody can be measured by use of an avidin-peroxidase conjugate and an appropriate substrate. The cross-blocking assay using enzyme (e.g., peroxidase) labeling is particularly referred to as competitive ELISA assay. The antibody can be labeled with other detectable or measurable labeling substances. Specifically, radiolabeling or fluorescent labeling or the like is known in the art.]

Furthermore, when the antibody to be tested has constant regions derived from a species different from that of an antibody of the present invention, the amount of each antibody bound to the well may be measured using a labeled antibody that recognizes the constant regions of this antibody. Alternatively, even antibodies derived from the same species, when differing in class, can be measured for their respective amounts bound to the well using antibodies that discriminate each class.

This competing antibody is determined to be an antibody that binds to substantially the same epitope as that bound by an antibody of the present invention, which comprises a) the following $V_H$ and $V_L$ domain CDRs having the amino acid sequence shown in SEQ ID Nos. 1 to 3 and 4 to 6, b) the following $V_H$ and $V_L$ domain CDRs having the amino acid sequence shown in SEQ ID Nos. 7 to 9 and 10 to 12, c) the following $V_H$ and $V_L$ domain CDRs having the amino acid sequence shown in SEQ ID Nos. 13 to 15 and 16 to 18 or competes therewith for the binding to the same epitope, provided that the competing antibody can block the binding of an antibody of the present invention by at least 20%, preferably at least 30%, more preferably at least 50%, compared with the affinity obtained in the control test performed in the absence of the candidate competing antibody.

The term "affinity" refers to the strength with which an antibody molecule binds an epitope. It measures the strength of any given bond between an epitope and an antibody's antigen binding site (also called paratope). High affinity antibodies bind quickly to the antigen, permit greater sensitivity in assays and maintain this bond more readily under difficult conditions. Low affinity antibodies, by contrast, bind weakly to the antigen and often do not detect the antigen in vivo or in assays. The affinity of monoclonal antibodies can be measured accurately because they are homogeneous and selective for a single epitope.

The term "epitope" used herein refers to a fragment of a polypeptide or protein or a non-protein molecule having antigenic or immunogenic activity in an animal, preferably in a mammal, and most preferably in a human. An epitope having immunogenic activity is a fragment of a polypeptide or protein that elicits an antibody response in an animal. An epitope having antigenic activity is a fragment of a polypeptide or protein to which an antibody immunospecifically binds as determined by any method well-known to one of skill in the art, for example by immunoassays. Antigenic epitopes need not necessarily be immunogenic.

As it is well known in the art, an antibody is an immunoglobulin molecule capable of specific binding to a target epitope through at least one epitope recognition site, located in the variable region of the immunoglobulin molecule. The terms "antibody", "antibody molecule" and "immunoglobulin" are used interchangeably and in their broadest sense herein and may include native antibodies, monoclonal antibodies, polyclonal antibodies, multi-specific antibodies (e.g., bispecific antibodies), (naturally occurring or synthetic) antibody derivatives, fragments or variants, fusion proteins comprising an antigen-binding fragment of the required specificity and any other modified configuration of the antibody that comprises an antigen-binding site or fragment (epitope recognition site) of the required specificity. Antibodies according to the invention are envisaged to be capable of specifically binding to the tissue-specific exosomes as described herein.

A "native antibody" is a tetrameric glycoprotein. In a naturally-occurring native antibody, each tetramer is composed of two identical pairs of polypeptide chains, each pair having one "light" (about 25 kDa) and one "heavy" chain (about 50-70 kDa). The amino-terminal portion of each chain includes a "(hyper)variable" region of about 100 to 110 or more amino acids primarily responsible for antigen recognition. The hypervariable region comprises amino acid residues from a "complementarity determining region" or CDRs. "Framework" or FR residues are those variable domain residues other than the hypervariable region residues.

Both the light and heavy chains are divided into regions of structural and functional homology referred to as the "constant region" and the "variable region." The terms "constant" and "variable" are used functionally. In this regard, it will be appreciated that the variable domains ($V_L$ and $V_H$) of both the light and heavy chains determine antigen recognition and specificity. Conversely, the constant domains of the light chain ($C_L$) and the heavy chain ($C_{H1}$, $C_{H2}$, or $C_{H3}$) confer important biological properties such as secretion, transplacental mobility, Fc receptor binding, complement binding, and the like. By convention the numbering of the constant region domains increases as they become more distal from the antigen binding site or amino-terminus of the antibody. The N-terminal portion is a variable region and at the C-terminal portion is a constant region; the $C_{H3}$ and $C_L$ domains actually comprise the carboxy-terminus of the heavy and light chain, respectively.

As indicated above, the variable region allows the antibody to selectively recognize and specifically bind epitopes on antigens. That is, the $V_L$ region (domain) and $V_H$ region (domain), or subset of the complementarity determining regions (CDRs) within these variable domains, of an antibody combine to form the variable region that defines a three dimensional antigen binding site. This quaternary antibody structure forms the antigen binding site present at the end of each arm of the Y. More specifically, the antigen binding site is defined by three CDRs on each of the $V_H$ and $V_L$ chains. In native antibodies, the six "complementarity determining regions" or "CDRs" present in each antigen binding domain are short, non-contiguous sequences of amino acids that are specifically positioned to form the antigen binding domain as the antibody assumes its three dimensional configuration in an aqueous environment. The CDRs of the variable light chain are also designated CDRL1, CDRL2 and CDRL3 herein. The CDRs of the variable heavy chain are also designated CDRH1, CDRH2, and CDRH3 herein.

The carboxy-terminal portion of each light and heavy chain defines a constant region primarily responsible for effector function. Immunoglobulins can be assigned to different classes depending on the amino acid sequence of the constant domain of their heavy chains. Heavy chains are classified as mu (μ), delta (Δ), gamma (γ), alpha (α), and epsilon (ε), and define the antibody's isotype as IgM, IgD, IgG, IgA, and IgE, respectively. Several of these may be further divided into subclasses or isotypes, e.g. IgG1, IgG2, IgG3, IgG4, IgA1 and IgA2. Light chains are classified as either kappa or lambda (κ, λ). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages.

Particularly envisaged in accordance with the present invention are monoclonal antibodies. An antibody of the present invention may also comprise antigen-binding fragments thereof. The term "monoclonal antibody" as used herein refers to an antibody obtained from a population of substantially homogeneous antibodies, i.e., the individual antibodies comprising the population are identical except for possible naturally occurring mutations that may be present in minor amounts. In contrast to conventional (polyclonal) antibody preparations that typically include different antibodies directed against different epitopes, monoclonal antibodies contain substantially similar epitope binding sites and are therefore typically directed against the same epitope on an antigen.

The present inventors immunized mice or rats with tissue-specific exosomes that had previously been isolated from human tissue or cultivated human cells that closely resemble the tissue or origin as described elsewhere herein and subsequently generated said monoclonal antibodies of the present invention (antibodies 23A11, 15G1 and 14H5) employing the hybridoma technique that is known in the art. Monoclonal antibodies of the present invention are therefore be derived from a non-human animal (such as a mouse or a rat, in particular from a rat). The term "monoclonal antibody" however also includes recombinant, chimeric, humanized, human, or Human Engineered™ monoclonal antibodies. An antibody of the present invention may also comprise a chimeric, a humanized or a human antibody.

The phrase "chimeric antibody," as used herein, refers to an antibody containing sequence derived from two different antibodies, which typically originate from different species. Specifically, the term refers to an antibody in which a portion of the heavy and/or light chain is identical with or homologous to corresponding sequences in antibodies derived from a particular species or belonging to a particular antibody class or subclass, while the remainder of the chain (s) is identical with or homologous to corresponding sequences in antibodies derived from another species or belonging to another antibody class or subclass, as well as fragments of such antibodies. Typically, chimeric antibodies may for instance comprise human and murine antibody fragments, generally human constant and mouse variable regions.

A "humanized antibody" is generally defined as one that is (I) derived from a non-human source (e.g., a transgenic mouse which bears a heterologous immune system), which antibody is based on a human germline sequence; or (II) CDR-grafted, wherein the CDRs of the variable domain are from a non-human origin, while one or more framework regions and/or part of the CDR sequence of the variable domain are of human origin and typically the constant domain (if any) is of human origin. The term "humanized antibody" thus includes antibodies in which the variable domain in either the heavy or light chain or both of a human antibody is altered by at least partial replacement of one or more CDRs from a non-human antibody of known specificity and, if necessary, by partial framework region replacement and sequence changing. In other words, an antibody in which one or more "donor" CDRs from a non-human antibody (such as a such as mouse, rat, rabbit or non-human primate antibody) of known specificity is grafted into a human heavy or light chain framework region is referred to herein as a "humanized antibody." It may not be necessary to replace all of the CDRs with the complete CDRs from the donor variable domain to transfer the antigen binding capacity of one variable domain to another. Rather, it may only be necessary to transfer those residues that are necessary to maintain the activity of the target binding site. In general, the humanized antibody will thus comprise substantially all of at least one, and typically two, variable domains, in which all or part of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin.

A "human" antibody is hereby defined as one that is not "chimeric" or "humanized" and not from (either in whole or in part) a non-human species. A human antibody or functional antibody fragment can be derived from a human or can be a synthetic human antibody. A "synthetic human antibody" is defined herein as an antibody having a sequence derived, in whole or in part, in silico from synthetic sequences that are based on the analysis of known human antibody sequences. In silico design of a human antibody sequence or fragment thereof can be achieved, for example, by analyzing a database of human antibody or antibody fragment sequences and devising a polypeptide sequence utilizing the data obtained therefrom. Another example of a human antibody or functional antibody fragment is one that is encoded by a nucleic acid isolated from a library of antibody sequences of human origin (i.e., such library being based on antibodies taken from a human natural source).

Various production methods for generating monoclonal antibodies are known in the art and are described, e.g., in Sambrook: Molecular Cloning, Cold Spring Harbor Laboratory Press, 4$^{th}$ ed., 2012). Suitable techniques include the hybridoma method, recombinant DNA methods that involve isolation and sequencing of DNA encoding the monoclonal antibodies, and its subsequent introduction and expression in suitable host cells, and the isolation of antibodies from antibody phage libraries. The present invention preferably comprises the hybridoma method to generate an antibody of the present invention, which preferably is capable of specifically binding to an exosomal surface marker of said tissue-specific exosomes.

As set out previously herein, the term "antibody" may encompass full-length antibodies as well as antigen-binding fragments, variants and derivatives thereof.

The term "antigen-binding fragment" refers to a polypeptide derived from a "parent" antibody and retaining its basic structure and function. An antibody fragment is hence preferably capable of binding to its specific antigen, i.e. a tissue-specific exosome as described herein, and in particular an exosomal surface marker. Thus, an antibody fragment is envisaged to comprise the minimum structural requirements of an antibody which allow for antigen binding. This minimum requirement may e.g. be defined by the presence of at least the three light chain CDRs (i.e. CDR1, CDR2 and CDR3 of the $V_L$ region) and/or the three heavy chain CDRs (i.e. CDR1, CDR2 and CDR3 of the $V_H$ region). Put it differently, the term "antibody fragment" refers to a "functional" or "antigen-binding" polypeptide that retains the antigen-binding region (i.e. the CDRs and optionally (part of) the FR) of a "parent" antibody. Antibody fragments may be derived from, e.g., monoclonal, recombinant, chimeric, humanized and human "parent" antibodies.

Pursuant with the foregoing, the term "antigen-binding fragments" particularly refers to fragments of full-length antibodies, such as (s)dAb, Fv, Fd, Fab, Fab', F(ab')$_2$ or "r IgG" ("half antibody"). Antibody fragments may also be modified fragments of antibodies such as scFv, di-scFv or bi(s)-scFv, scFv-Fc, scFv-zipper, scFab, Fab$_2$, Fab$_3$, diabodies, single chain diabodies, tandem diabodies (Tandab's), tandem di-scFv, tandem tri-scFv, "minibodies" exemplified by a structure which is as follows: $(V_H-V_L-CH_3)_2$, (scFv-CH$_3$)$_2$ or (scFv-CH$_3$-scFv)$_2$, multibodies such as triabodies or tetrabodies, and single domain antibodies such as nanobodies or single variable domain antibodies comprising merely one variable domain, which might be $V_H$H, $V_H$ or $V_L$, that specifically bind an antigen or epitope independently of other V regions or domains.

Furthermore, the definition of the term "antigen-binding fragments" includes constructs comprising said fragments, i.e. monovalent, bivalent and polyvalent/multivalent constructs and, thus, monospecific constructs, specifically binding to only one antigenic structure, as well as bispecific and polyspecific/multispecific constructs, which specifically bind more than one antigenic structure, e.g. two, three or more, through distinct binding domains. Moreover, the definition of the term "antibody fragments" includes molecules consisting of only one polypeptide chain as well as molecules consisting of more than one polypeptide chain, which chains can be either identical (homodimers, homotrimers or homo oligomers) or different (heterodimer, heterotrimer or heterooligomer).

The term "antigen-binding fragment" can be used interchangeably with the term "antibody fragment".

Antibody fragments may be produced by recombinant DNA techniques or by enzymatic or chemical cleavage of intact antibodies. Methods for producing such fragments are well-known in the art.

The term "variant" refers to antibodies comprising the amino acid sequence of a "parent" antibody, but containing at least one amino acid modification (i.e. a substitution, deletion, or insertion) as compared to the "parent" amino acid sequence, provided that the variant is still capable of (specifically) binding to tissue-specific exosomes, in particular an exosomal surface marker as described herein. Variants of antibodies are typically prepared by introducing appropriate nucleotide changes into the nucleic acids encoding the antibody, or by peptide synthesis. Generally, the aforementioned amino acid modifications may be introduced into, or present in, the variable region or the constant region As set out previously, amino acid modifications include, for example, deletions from, and/or insertions into, and/or substitutions of, residues within the amino acid sequences of the antibodies. Any combination of deletion, insertion, and substitution can be introduced into the "parent" amino acid sequence in order to arrive at the antibody variant, provided that it possesses the desired characteristics as set out elsewhere herein. The amino acid modifications also may alter post-translational processes of the binding molecules, such as changing the number or position of glycosylation sites.

E.g., 1, 2, 3, 4, 5, or 6 amino acids may be inserted or deleted in each of the CDRs (of course, dependent on their length), while 1, 2, 3, 4, 5, 6, 7, 8, 9, 10, 11, 12, 13, 14, 15, 16, 17, 18, 19, 20, or 25 amino acids may be inserted or deleted in each of the FRs. Amino acid sequence insertions envisaged herein include amino- and/or carboxyl-terminal fusions ranging in length from 1, 2, 3, 4, 5, 6, 7, 8, 9 or 10 residues to polypeptides containing a hundred or more residues, as well as intra-sequence insertions of single or multiple amino acid residues. An insertional variant of a binding molecule, in particular an antibody or antibody fragment, may include a fusion product of an antibody or antibody fragment and an enzyme or another functional polypeptide (e.g., which increases the serum half-life of the antibody or antibody fragment).

Amino acid substitutions can be introduced into the CDRs of the heavy and/or light chain, in particular the hypervariable regions, or the FR regions in the heavy and/or light chain. Particularly envisaged herein are conservative amino acid substitutions that may be made, for instance, on the basis of similarity in polarity, charge, solubility, hydrophobicity, hydrophilicity, and/or the amphipathic nature of the residues involved.

E.g., 1, 2, 3, 4, 5, 6, 7, 8, 9, or 10 amino acids may be substituted in a CDR, while 1, 2, 3, 4, 5, 6, 7, 8, 9, 10, 11, 12, 13, 14, 15, 16, 17, 18, 19, 20, or 25 amino acids may be substituted in the framework regions (FRs), depending on the length of the CDR or FR.

Generally, if amino acids are substituted in one or more or all of the CDRs of the heavy and/or light chain, it is preferred that the then-obtained "variant" sequence is at least 60%, more preferably, at least 70% or 80%, still more preferably at least 90% and most preferably at least 95%, 96%, 97%, 98% or 99% identical to the "parent" CDR sequence. The length of the CDR thus influences the number of possible amino acid substitutions so that the variant sequence is still encompassed by the invention. For example, a CDR having 5 amino acids is preferably 80% identical to its substituted sequence in order to have at least one amino acid substituted. Accordingly, the CDRs of the antibody may have different degrees of identity to their substituted sequences, e.g., CDRL1 may have 80%, while CDRL3 may have 90%.

As explained previously, conservative substitutions are often preferred. However, any substitution is envisaged as long as the antibody or antigen-binding fragment thereof retains its capability to (specifically) bind to a tissue-specific exosome or particularly an exosomal surface marker as described herein and/or its CDRs have an identity to "parent" sequence of at least 60%, more preferably, at least 70% or 80%, still more preferably at least 90% and most preferably at least 95%, 96%, 97%, 98% or 99%.

As used herein, the term "sequence identity" indicates the extent to which two (nucleotide or amino acid) sequences have identical residues at the same positions in an alignment, and is often expressed as a percentage. Preferably, identity is determined over the entire length of the sequences being compared. Thus, two copies of exactly the same sequence have 100% identity, but sequences that are less highly conserved, and have deletions, additions, or replacements, may have a lower degree of identity. Those skilled in the art will recognize that several algorithms are available for determining sequence identity using standard parameters, for example Blast (Altschul, et al. (1997) Nucleic Acids Res. 25:3389-3402), Blast2 (Altschul, et al. (1990) J. Mol. Biol. 215:403-410), Smith-Waterman (Smith, et al. (1981) J. Mol. Biol. 147:195-197) and ClustalW.

The term "sequence homology" indicates the similarity of two (nucleotide or amino acid) sequences attributed to descent from a common ancestor. Homologous biological components (genes, proteins, structures) are called homologs and include orthologs.

Preferred antibody variants have a sequence identity or homology in the CDR regions of at least 60%, more preferably, at least 70% or 80%, still more preferably at least 90% and most preferably at least 95%, 96%, 97%, 98%, 99% or almost 100% and are capable of (specifically) binding to tissue-specific exosomes and in particular exosomal surface markers. Moreover, the nucleic acid sequence homology or similarity between the nucleotide sequences encoding individual variant CDRs and the nucleotide sequences depicted herein are at least 60%, and more typically with preferably increasing homologies or identities of at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99%, and almost 100%.

Besides in the CDRs and FRs, amino acid modifications may also be introduced into the Fc part of a binding molecule, particularly an antibody. Such modifications can be used in order to modulate interactions with the complement protein C1q and/or Fc receptors on other immune cells. Thus, mutations for modification of effector functions may be introduced into the Fc domains using routine methods known in the art. Exemplary modifications include Asn297→Ala297 and Asn297→Gln297 resulting in aglycosylation of IgG1, or Lys322→Ala322 and optionally Leu234→Ala234 and Leu235→Ala234 which have been reported to reduce or abolish antibody-derived cell-mediated cytotoxicity (ADCC) and/or complement-derived cytotoxicity (CDC).

The term "derivative" refers to molecules that have been covalently modified to introduce an additional functionality. Covalent modifications of the binding molecules are often introduced post-translationally, and can be introduced into the binding molecule by reacting specific amino acid residues of the molecule with an organic derivatizing or cross-linking agent that is capable of reacting with selected side chains or the N- or C-terminal residues. Cross-linking reagents contain at least two reactive groups, and are divided generally into homofunctional cross-linkers (containing identical reactive groups) and heterofunctional cross-linkers (containing non-identical reactive groups). Homobifunctional cross-linkers that couple through amines, sulfhydryls or react non-specifically are available from many commercial sources. Maleimides, alkyl and aryl halides, alpha-haloacyls and pyridyl disulfides are thiol reactive groups. Maleimides, alkyl and aryl halides, and alpha-haloacyls react with sulfhydryls to form thiol ether bonds, while pyridyl disulfides react with sulfhydryls to produce mixed disulfides. The pyridyl disulfide product is cleavable. Imidoesters are also very useful for protein-protein cross-links. A variety of heterobifunctional cross-linkers, each combining different attributes for successful conjugation, are commercially available. Derivatization of binding molecules can be used to attach therapeutic or diagnostic agents, labels, groups extending the serum half-life of the molecule, or insertion of non-natural amino acids. Derivatives may also be obtained by acylation or acetylation of the N-terminal end or amidation or esterification of the C-terminal end or, alternatively, of both, or by alkylation (e. g., methylation, propylation, butylation), arylation, or etherification.

Examples for means to extend serum half-life of an antibody of the present inevntionincludes the attachment of peptides or protein domains binding to other proteins in the human body (such as serum albumin, the immunoglobulin Fc region or the neonatal Fc receptor (FcRn). Further conceivable modifications to extend the serum half-life comprise the extension of an amino group with polypeptide chains of varying length (e.g., XTEN technology or PASylation®), the conjugation of non-proteinaceous polymers, including, but not limited to, various polyols such as polyethylene glycol (PEGylation), polypropylene glycol, polyoxyalkylenes, or copolymers of polyethylene glycol and polypropylene glycol, or of carbohydrates, such as hydroxyethyl starch (e.g., HESylation®) or polysialic acid (e.g., PolyXen® technology). In addition, as is known in the art, amino acid substitutions may be made in various positions within the binding molecule in order to facilitate the addition of said polymers.

Another type of covalent modification of an antibody of the present invention comprises altering their glycosylation pattern. As is known in the art, glycosylation patterns can depend on both the amino acid sequence of said molecule (e.g., the presence or absence of particular glycosylation amino acid residues, discussed below), or the host cell or organism in which the protein is produced. Glycosylation of polypeptides is typically either N-linked or O-linked. N-linked refers to the attachment of the carbohydrate moiety to the side chain of an asparagine residue. Addition of N-linked glycosylation sites to the antibody is conveniently accomplished by altering the amino acid sequence such that it contains one or more tri-peptide sequences selected from asparagine-X-serine and asparagine-X-threonine (where X is any amino acid except proline). O-linked glycosylation sites may be introduced by the addition of, or substitution by, one or more serine or threonine residues to the starting sequence.

Another means of glycosylation of an antibody of the present invention is by chemical or enzymatic coupling of glycosides to the protein. These procedures are advantageous in that they do not require production of the protein in a host cell that has glycosylation capabilities for N- and O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine.

Similarly, deglycosylation (i.e., removal of carbohydrate moieties present on the binding molecule) may be accomplished chemically, e.g. by exposure of the binding molecule to trifluoromethanesulfonic acid, or enzymatically by employing endo- and exo-glycosidases.

Further potential covalent modifications of an antibody of the present invention comprise the addition of one or more labels. The labelling group may be coupled to an antibody of the present invention via spacers of various lengths to reduce potential steric hindrance. Various methods for labelling proteins are known in the art and can be used in performing the present invention. The term "label" or "labelling group" refers to any detectable label. In general, labels fall into a variety of classes, depending on the assay in which they are to be detected—the following examples include, but are not limited to: isotopic labels, which may be radioactive or heavy isotopes, such as radioisotopes or radionuclides (e.g., $^{3}H$, $^{14}C$, $^{15}N$, $^{35}S$, $^{89}Zr$, $^{90}Y$, $^{99}Tc$, $^{111}In$, $^{125}I$, $^{131}I$); magnetic labels (e.g., magnetic particles); redox active moieties; optical dyes (including, but not limited to, chromophores, phosphors and fluorophores) such as fluorescent groups (e.g., FITC, rhodamine, lanthanide phosphors), chemiluminescent groups, and fluorophores which can be either "small molecule" fluorophores or proteinaceous fluorophores; enzymatic groups (e.g. horseradish peroxidase, β-galactosidase, luciferase, alkaline phosphatase; biotinylated groups; or predetermined polypeptide epitopes recognized by a secondary reporter (e.g., leucine zipper pair sequences, binding sites for secondary antibodies, metal binding domains, epitope tags, etc.)

An antibody of the present invention may also comprise additional domains, which are aid in purification and isolation of the molecule (affinity tags). Non-limiting examples of such additional domains comprise peptide motives known as Myc-tag, HAT-tag, HA-tag, TAP-tag, GST-tag, chitin binding domain (CBD-tag), maltose binding protein (MBP-tag), Flag-tag, Strep-tag and variants thereof (e.g. StrepII-tag) and His-tag.

The aforementioned fragments, variants and derivatives may be further adapted in order to improve, e.g., their antigen binding properties. For instance, $F(ab')_2$ or Fab may be engineered to minimize or completely remove the intermolecular disulphide interactions that occur between the $C_{H1}$ and $C_L$ domains. Fv polypeptides may further comprise a polypeptide linker between the $V_H$ and $V_L$ domains that enables the Fv to form the desired structure for antigen binding. The Fab fragment also contains the constant domain of the light chain and the first constant domain (CH1) of the heavy chain. Fab fragments differ from Fab' fragments by the addition of a few residues at the carboxy terminus of the heavy chain CH1 domain including one or more cysteines from the antibody hinge region. Fab'-SH is the designation herein for Fab' in which the cysteine residue (s) of the constant domains bear a free thiol group. $F(ab')_2$ antibody fragments originally were produced as pairs of Fab' fragments which have hinge cysteine residues between them.

An antibody of the present invention may be provided in "isolated" or "substantially pure" form. The same applies to polynucleotides encoding the same. "Isolated" or "substantially pure" when used herein means that a binding molecule or polynucleotide encoding the same is identified, separated and/or recovered from a component of its environment, such that the "isolated" molecule is free or substantially free of other contaminant components from its environment that might interfere with its therapeutic or diagnostic use. Contaminant components may include enzymes, hormones, and other proteinaceous or non-proteinaceous solutes. "Isolated" antibody of the invention may thus be prepared by at least one purification step removing or substantially removing these contaminant components.

For the purposes of the present invention, an antibody of the present invention may be linked directly or indirectly to a solid phase, surface or substrate. Solid phases that may be used to immobilize specific binding members include those developed and/or used as solid phases in solid phase binding assays.

Said solid surface or substrate can be any physically separable solid to which a an antibody of the present invention may be directly or indirectly attached including, but not limited to, surfaces provided by (micro)arrays and wells, particles such as beads, columns, optical fibers, wipes, glass and modified or functionalized glass, quartz, mica, diazotized membranes (paper or nylon), polyformaldehyde, cellulose, cellulose acetate, paper, ceramics, metals, metalloids, semiconductive materials, quantum dots, coated beads or particles, other chromatographic materials, magnetic particles; plastics (including acrylics, polystyrene, copolymers of styrene or other materials, polypropylene, polyethylene, polybutylene, polyurethanes, TEFLON™, etc.), polysaccharides, nylon or nitrocellulose, resins, silica or silica-based materials including silicon and modified silicon, carbon, metals, inorganic glasses, plastics, ceramics, conducting polymers (including polymers such as polypyrole and polyindole); micro or nanostructured surfaces such as nucleic acid tiling arrays, nanotube, nanowire, or nanoparticulate decorated surfaces; or porous surfaces or gels such as methacrylates, acrylamides, sugar polymers, cellulose, silicates, or other fibrous or stranded polymers. In addition, as is known the art, the substrate may be coated using passive or chemically-derivatized coatings with any number of materials, including polymers, such as dextrans, acrylamides, gelatins or agarose.

For example, exosomes can be isolated by contacting a sample with an antibody of the present invention bound to a solid substrate such as a well, or an array. Said antibody of the present invention can also be bound to particles such as beads or microspheres, which may optionally be magnetic or fluorescently labeled in order to facilitate isolation and/or detection.

The present invention comprises a standardized immunoprecipitation assay with an antibody of the present invention being specific for said tissue-specific EVs for capturing sufficient amounts of said tissue-specific derived EVs from a patient sample (Example 1.21). Preferably capturing sufficient amounts of AT derived EV samples. The isolation of tissue-specific EVs by using an organ-specific antibody of the present invention which is capable of specifically binding to a specific exosomal surface marker exceeds the isolation techniques with antibodies against standard (non-organ specific) EV markers such as CD9, CD63, CD81 or Alix.

An antibody of the present invention may also be used for multiplexing in order to allow for isolation of exosomes. Therefore, each type of exosome may be isolated using a different antibody of the present invention capable of specifically binding to said tissue-specific exosome. An antibody of the present invention may for instance be bound to different particles, which may be labeled. It is also conceivable to use an array comprising an antibody of the present invention for multiplex analysis, wherein an antibody of the present invention are differentially labeled or can be ascertained based on the location of an antibody of the present invention on the array.

An antibody of the present invention is preferably advantageously capable of binding to tissue-specific exosomes, in particular to a tissue-specific exosomal surface marker. The terms "binding to" and "recognizing" in all grammatical forms are used interchangeably herein. Preferably, said antibody of the present invention specifically binds to tissue-specific exosomes, in particular to a tissue-specific exosomal surface marker. The term "specifically binds" generally indicates that an antibody as described herein, binds via its antigen binding domain more readily to its intended target molecule (and/or epitope) than to a random, unrelated non-target molecule (and/or epitope). Particularly, the term "specifically binds" indicates that the affinity of the binding molecule will be at least about 5 fold, preferably 10 fold, more preferably 25-fold, even more preferably 50-fold, and most preferably 100-fold or more, greater for its target tissue-specific exosome or exosomal surface maker than its affinity for a non-target exosome or exosomal surface marker.

Thus, an antibody of the present invention may be considered to specifically bind to its target epitope if it binds said epitope with a dissociation constant ($K_D$) that is less than its $K_D$ for a non-target epitope. An antibody of the present invention may thus also be described in terms of their binding affinity to a tissue-specific exosome. The term "affinity" or "binding affinity" refers to the strength of the binding of an individual epitope with an antigen-binding domain (and in particular the CDRs of the binding molecule). The affinity of the binding of a given antibody to its specific target is often determined by measurement of the equilibrium association constant (ka) and equilibrium dissociation constant (kd) and calculating the quotient of kd to ka ($K_D$=kd/ka). Binding affinities may be readily determined using conventional techniques, such as by equilibrium dialysis; by using the BIAcore 2000 instrument; by radioimmunoassay using radio labeled target antigen; or by another method known to the skilled artisan. Preferred binding affinities of the inventive binding molecules include those with a dissociation constant or $K_D$ less than $5\times10^{-6}$ M, $10^{-6}$ M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, or $10^{-15}$M.

Kit

Also provided herein is a kit for performing the method described above, comprising means for detecting the presence of a tissue-specific exosomal surface marker by an antibody of the present invention which is capable of specifically binding to said tissue-specific exosomal surface marker. Said means are preferably provided in one or more containers or vials which may be associated with a notice in the form prescribed by a governmental agency regulating the manufacture, use or sale of pharmaceuticals or biological products, reflecting approval by the agency of the manufacture, use or sale of the product for human administration or diagnostics.

The kit may further comprise means for isolating tissue-specific exosomes, wherein said tissue-specific exosomes are isolatable by an antibody capable of specifically binding to a tissue-specific exosomal surface marker, wherein said antibody comprise a) the following $V_H$ and $V_L$ domain CDRs having the amino acid sequence shown in SEQ ID Nos. 1 to 3 and 4 to 6, b) the following $V_H$ and $V_L$ domain CDRs having the amino acid sequence shown in SEQ ID Nos. 7 to 9 and 10 to 12, c) the following $V_H$ and $V_L$ domain CDRs having the amino acid sequence shown in SEQ ID Nos. 13 to 15 and 16 to 18, and means for detecting the presence of at least one exosomal biomarker indicative for a metabolic disease as described herein.

In Vitro Methods

The present invention thus also provides an in vitro method of diagnosing or monitoring a metabolic disease in a subject or predicting the risk of a subject of developing a metabolic disease, comprising (i) isolating tissue-specific exosomes from a sample of the subject, wherein said tissue-specific exosomes are isolatable by an antibody capable of specifically binding to a tissue-specific exosomal surface marker, wherein said antibody comprises a) the following $V_H$ and $V_L$ domain CDRs having the amino acid sequence shown in SEQ ID Nos. 1 to 3 and 4 to 6, b) the following $V_H$ and $V_L$ domain CDRs having the amino acid sequence shown in SEQ ID Nos. 7 to 9 and 10 to 12, c) the following $V_H$ and $V_L$ domain CDRs having the amino acid sequence shown in SEQ ID Nos. 13 to 15 and 16 to 18, and (ii) determining the presence of at least one exosomal biomarker that is indicative for a metabolic disease or for the risk of developing a metabolic disease. The method may comprise in step (i) contacting the sample with an antibody of the present invention capable of specifically binding to a tissue-specific exosomal biomarker. For step (i), the present invention comprises a standardized immunoprecipitation (IP) assay with an antibody of the present invention being organ-specific for said tissue-specific EVs for capturing sufficient amounts of said tissue-specific derived EVs from a patient sample, which is selected from a blood sample, a plasma sample, a serum sample, lymph, saliva, bile, feces, breast milk, urine sample, cerebrospinal fluid sample, amniotic fluid, or an organ or tissue biopsy. The combination of a standardized IP and the use of said newly generated antibodies of the present invention is an improved strategy over the prior art for extracting tissue-specific EVs from a sample obtained from a subject to be diagnosed. For step (ii) after bound EVs will be extracted from the beads used in IP in step (i), mass spectrometry to investigate the proteome of EVs for at least one exosomoal biomarker may be run.

The invention also relates to a method for isolating tissue-specific exosomes from a sample, said method comprising a step of contacting said sample with an antibody capable of specifically binding to a tissue-specific exosomal surface marker, wherein said antibody comprises a) the following $V_H$ and $V_L$ domain CDRs having the amino acid sequence shown in SEQ ID Nos. 1 to 3 and 4 to 6, b) the following $V_H$ and $V_L$ domain CDRs having the amino acid sequence shown in SEQ ID Nos. 7 to 9 and 10 to 12, c) the following $V_H$ and $V_L$ domain CDRs having the amino acid sequence shown in SEQ ID Nos. 13 to 15 and 16 to 18. Particularly, an antibody of the present invention is optionally immobilized on a solid support as described previously for said IP assay mentioned above.

Additionally, the present invention may include a method of detecting an exosomal biomarker being indicative for a metabolic disease, comprising administering an effective amount of an antibody of the present invention to a subject in need thereof, wherein said antibody comprises a) the following $V_H$ and $V_L$ domain CDRs having the amino acid sequence shown in SEQ ID Nos. 1 to 3 and 4 to 6, b) the following $V_H$ and $V_L$ domain CDRs having the amino acid sequence shown in SEQ ID Nos. 7 to 9 and 10 to 12, c) the following $V_H$ and $V_L$ domain CDRs having the amino acid sequence shown in SEQ ID Nos. 13 to 15 and 16 to 18 and wherein said antibody is capable of specifically binding to said exosomal biomarker.

The subject may be any subject as defined herein, preferably a human subject. The subject is preferably in need of the administration of an antibody of the present invention.

Further, the present invention may envisage the use of an antibody of the present invention capable of specifically binding to a tissue-specific exosomal surface marker, wherein said antibody comprises a) the following $V_H$ and $V_L$ domain CDRs having the amino acid sequence shown in SEQ ID Nos. 1 to 3 and 4 to 6, b) the following $V_H$ and $V_L$ domain CDRs having the amino acid sequence shown in SEQ ID Nos. 7 to 9 and 10 to 12, c) the following $V_H$ and $V_L$ domain CDRs having the amino acid sequence shown in SEQ ID Nos. 13 to 15 and 16 to 18, for the manufacture of a medicament for therapeutic application in obesity, insulin resistance, prediabetes or type 1 or type 2 diabetes.

It must be noted that as used herein, the singular forms "a", "an", and "the", include plural references unless the context clearly indicates otherwise. Thus, for example, reference to "a reagent" includes one or more of such different reagents and reference to "the method" includes reference to equivalent steps and methods known to those of ordinary skill in the art that could be modified or substituted for the methods described herein.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

The term "and/or" wherever used herein includes the meaning of "and", "or" and "all or any other combination of the elements connected by said term".

The term "about" or "approximately" as used herein means within 20%, preferably within 10%, and more preferably within 5% of a given value or range. It includes, however, also the concrete number, e.g., about 20 includes 20.

The term "less than" or "greater than" includes the concrete number. For example, less than 20 means less than or equal to. Similarly, more than or greater than means more than or equal to, or greater than or equal to, respectively.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having".

When used herein "consisting of" excludes any element, step, or ingredient not specified in the claim element. When used herein, "consisting essentially of" does not exclude materials or steps that do not materially affect the basic and novel characteristics of the claim.

In each instance herein any of the terms "comprising", "consisting essentially of" and "consisting of" may be replaced with either of the other two terms.

It should be understood that this invention is not limited to the particular methodology, protocols, material, reagents, and substances, etc., described herein and as such can vary. The terminology used herein is for the purpose of describing particular embodiments only, and is not intended to limit the scope of the present invention, which is defined solely by the claims.

All publications and patents cited throughout the text of this specification (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention. To the extent the material incorporated by reference contradicts or is inconsistent with this specification, the specification will supersede any such material.

A better understanding of the present invention and of its advantages will be obtained from the following example, offered for illustrative purposes only. The example is not intended to limit the scope of the present invention in any way.

EXAMPLES

Example 1: Material and Methods

Example 1.1: Mouse Experiments

Male C57BL/6J mice (Janvier, Le Genest St Isle, France; 6 weeks of age) were housed three per cage at the Helmholtz Centre in Munich under specified pathogen free conditions. After one week of acclimatization, mice were ad libitum fed with high-fat diet (HFD), 58% calories from fat; 5.56 kcal/g, (D12331, Research Diets, New Brunswick, N.J.) or chow (#1310, Altromin, Lage, Germany) for 16-24 weeks. Mice from the calorie restriction (CR) group were switched from 6-months-HFD to ca. 1 g/day of standard chow diet for 9 days. Mice were sacrificed by $CO_2$ followed by heart puncture and blood collection. White fat pads were excised and used for exosome isolations or were snap frozen on dry ice for later sample processing. The Animal Use and Care Committee of the state of Bavaria, Germany, approved all procedures.

Example 1.2: Exosome Isolation from Murine Adipose Tissue, Serum and Panc02 Cell Culture Supernatants For exosome isolation from murine adipose tissue, gonadal or inguinal fat pads were excised and immediately transferred to DMEM (4.5 g/L glucose, GlutaMAX, Thermo Fisher Scientific, Waltham, Mass.). Finely minced fat pads were digested using 0.075% Collagenase IV (Thermo Fisher Scientific), for 50 min and adipocyte fractions were passed through a 100 μM mesh and separated from the SVF by centrifugation at 100 g for 10 min. The adipocyte layer was then carefully removed and incubated in exosome medium (DMEM 4.5 g/L glucose, with 0.2% BSA) for 2 h at 37° C. in a humidified atmosphere. After the incubation time, cell culture media were collected and secreted exosomes were isolated by differential centrifugation. Media were initially centrifuged for 10 min at 1000 g to remove debris and broken cells, followed by a 30 min step at 10,000 g to remove remaining fragments. Hereafter, exosomes were spun down at 100,000 g for 70 min, washed in 1×PBS and centrifuged again at 100,000 g for 70 min. All centrifugation steps were carried out at 4° C. Exosome enriched fractions were re-suspended in exosome buffer (0.25 M Sucrose, 10 mM Tris-HCl, 1 mM EDTA, 140 mM NaCl, pH 7.4, supplemented with EDTA free complete mini protease inhibitor tablets (Roche, Basel, Switzerland) and used for subsequent experiments or stored at -80° C.

Exosomes from fresh mouse serum were collected with ExoQuick® (System Bioscience, Inc., Mountain View, Calif.). Pellets were dissolved in 1×PBS and centrifuged for 70 min at 100,000 g to remove excess reagent and potential impurities. All centrifugation steps were carried out at 4° C. Exosome protein concentrations were determined by BCA assay. Purity and presence of classical exosome markers was tested using specific antibodies against CD63 (Bioss, Inc. Woburn, Mass.), CD81 (Bioss), CD9 (Millipore, Billerica, Mass.) and HRP-conjugated cholera-toxin B subunit for ganglioside M1 detection (Thermo-Fisher Scientific). Prior to antibody incubation, exosomes were dot-blotted at RT onto nitrocellulose membranes (Whatman) using a MiniFold SpotBlot system (Whatman, GE Healthcare, Little Chalfont, UK). Dot densities were determined using ImageJ software (Rasband, W. S., ImageJ, U. S. National Institutes of Health, Bethesda, Md., USA).

To obtain exosome-enriched fractions from cell culture supernatants from the pancreatic cancer cell line Panc02[37], cells were grown in normal growth medium (DMEM, 4.5 g/Glucose with L-Glutamin (Thermo Fisher Scientific), supplemented with Penicillin/Streptomycin, and fetal bovine serum). After reaching 60-70% confluence, cells were shifted to FCS deprived growth medium and maintained for 48 h. Medium supernatants were harvested and exosomes were isolated using differential centrifugation. Briefly, the following centrifugation steps were applied: 10 min at 300 g, 30 min at 10,000 g and 70 min at 100,000 g. Finally the exosome-enriched pellet was washed in 1×PBS and spun down again at 100,000 g for 130 min. Pellets were treated as mentioned above.

Example 1.3: Transmission Electron Microscopy

Transmission electron microscopy was used to verify the presence and appearance of exosomes in our isolated fractions. Exosome suspensions (5 μl) were deposited on formvar-carbon coated EM grids (200 mesh Copper, Piano GmbH, Wetzlar, Germany) for 1 minute. The grids were transferred to a 5 μl drop of 0.5% uranyl acetate in 70% ethanol solution (Merck KgaA, Darmstadt, Germany) for 10 seconds twice and then air dried for 10 minutes. The samples were examined by transmission electron microscopy (Zeiss Libra 120 Plus, Carl Zeiss NTS GmbH, Oberkochen, Germany). Pictures were acquired using a Slow Scan CCD-camera and iTEM software (Olympus Soft Imaging Solutions, Munster, Germany).

Example 1.4: Sample Preparation for Mass Spectrometric Analysis

Frozen eWAT samples were homogenized in 10 mM Tris-HCl buffer (pH 7.4), supplemented with supplemented with EDTA free complete mini protease inhibitor tablets (Roche, Basel, Switzerland), by using a dounce homogenizer. Lysates were centrifuged first at 1000 g for 10 min to remove debris and nuclei, followed by a 20 min centrifugation step at 10,000 g. All centrifugation steps were carried out at 4° C. Final protein concentrations were determined using Coomassie reagent (Bio-Rad, Hercules, Calif.) according to the manufacturer's protocol. For proteomic studies freshly isolated eWAT, iWAT and serum derived exosomes were stored at -80° C. Subsequently, 10 μg per sample (isolated exosomes or whole cell lysates) were subjected to tryptic digestion using a modified filter aided sample preparation (FASP) procedure[38, 39]. Immediately prior to mass spectrometric analysis, all samples were thawed on ice and centrifuged for 5 min at 4° C. LC-MS/MS analysis of 0.5 μg per sample was performed as previously described[40, 41] using an LTQ-OrbitrapXL (Thermo Fisher Scientific) coupled to an Ultimate 3000 nano-HPLC (Dionex, Sunnyvale, Calif.). Further details are given elsewhere herein. The acquired spectra were loaded to the Progenesis LC-MS software (version 2.5, Nonlinear) for label free quantification and analyzed as previously described[40, 41]. Profile data of the MS and MS/MS scans were transformed to peak lists with respective peak m/z values, intensities, abundances (areas under the peaks) and m/z width. After reference selection, the retention times of the other samples were aligned by automatic alignment to a maximum overlay of all features (at least 92.4% for eWAT exosomes, 85.8% for serum exosomes, 90.1% for iWAT exosomes, 93.2% for eWAT whole proteome). MS/MS spectra of features with charges of +2 to +7 were exported as mascot generic file and used for peptide identification with Mascot (version 2.3) in the Ensembl mouse protein database (release 72, 23210570 residues, 51372 sequences). Search parameters used were: 10 ppm peptide mass tolerance and 0.6 Da fragment mass tolerance, one missed cleavage allowed, carbamidomethylation was set as fixed modification, methionine oxidation and asparagine or glutamine deamidation were allowed as variable modifications. Searches were filtered with a mascot percolator score cut-off of 15 and an appropriate significance threshold p, in order to reach a false discovery rate of <1%. Peptide identifications were re-imported into the Progenesis LC-MS software. Summed normalized abundances of the proteins were exported and used for calculation of fold-changes and significance between groups.

Example 1.5: miRNA Profiling of eWAT Exosomes

Isolated exosomes were lysed in Qiazol® lysis reagent (Qiagen, Hilden, Germany) and pre-purified by phenol (Qiazol)/chloroform extraction. Nucleic acids in the aqueous phase were precipitated with 100% ethanol and total RNA was extracted using the Qiagen miRNeasy® Mini Kit (Qiagen) according to standard protocols. RNA was eluted by adding 50 µL of RNase-free water. cDNA syntheses and real-time qPCRs were performed using the miRCURY LNA™ Universal RT microRNA PCR system (Exiqon, Vedbaek, Denmark) according to the manufacturer's instructions. The cDNA products were subsequently diluted and transferred to the ready-to-use microRNA PCR Mouse & Rat PCR panel I and quantified using SYBR green based real time PCR and LNA enhanced miRNA specific primers. Negative controls excluding template from the reverse transcription reaction were handled and profiled like experimental samples. The amplification was performed in a LightCycler® 480 Real-Time PCR System (Roche) in 384 well plates. The amplification curves were analyzed using the Roche LC software, both for determination of the quantification cycle (Cq) and for melting curve analysis. Using NormFinder (MOMA, Department of Molecular Medicine, Aarhus University Hospital, Denmark) the best normalizer was found to be the average of assays detected in all samples. All data was normalized to the average of assays detected in all samples (average-assay Cq).

Example 1.6: Bone Marrow-Derived Macrophage Isolation and Exosome Treatment

Bone marrow cell suspensions were isolated by flushing femurs and tibias of 8- to 10-week-old C57BL/6J mice with RPMI1640 (Thermo Fisher Scientific) containing 2% FCS. To eliminate erythrocyte contaminations cells were incubated with Ery-Lysis-Buffer (154 mM $NH_4Cl$, 10 mM $KHCO_3$, 0.1 mM EDTA) and washed with PBS. Additionally, a density gradient centrifugation with Ficoll-Paque (GE-Healthcare) was performed to isolate bone marrow mononuclear cells, representing the middle fraction after centrifugation. For macrophage selection, cell suspensions were washed once and seeded onto non-tissue culture treated petri dishes (Greiner Bio-One, Frickenhausen, Germany) in BMDM differentiation medium (DMEM high glucose with 2 mM L-glutamine supplemented with 20% FCS, 30% L929 supernatant, 100 U/ml penicillin, 100 µg/ml streptomycin and 50 µg/ml normocin). BMDMs were differentiated for 5 days with a change of medium every two days. BMDMs were seeded in 6 well plates with $1.5 \times 10^6$ cells per well in serum-free medium. Six hours after seeding, cells were treated with 1 µg/ml or 5 µg/ml of exosomes isolated from lean and obese eWAT samples in absence or presence of IFNγ (20 ng/ml) and IL-4 (10 ng/ml) to induce M1 and M2 polarization. M1/M2 marker gene expression was measured using qPCR, 24 hours after treatment.

Example 1.7: Isolation and Culture of Primary Inguinal Pre-Adipocytes

For pre-adipocyte preparations inguinal fat pads of 6- to 8-week-old male C57BL/6J mice were excised, washed in DMEM/F12 GlutaMAX, minced and digested using 0.15% Collagenase IV and 2% BSA. Samples were incubated for 50 min at 37° C. under gentle shaking. Digested tissue was passed through a 100 µm mesh and floating adipocytes were separated by centrifugation at 400 g for 10 min. Adipocytes and supernatant were removed and the stromal vascular fraction (SVF) re-suspended and incubated in erythrocyte lysis buffer (154 mM NH4Cl, 10 mM KHCO3, 0.1 mM EDTA). The SVF was pelleted by another centrifugation step at 400 g for 10 min, taken up in culture medium (DMEM/F12 GlutaMAX, 10% FCS and Penicillin/Strepomycin), passed through a 40 µm mesh and seeded. Differentiation was induced by adding induction medium (culture medium supplemented with 1 µM dexamethasone, 0.5 mM IBMX, 5 µg/µl insulin) when cells reached 90% confluence. Two days post induction, medium was changed to differentiation medium (culture medium supplemented with 5 µg/ml insulin). At day 5 of differentiation cells were shifted to exosome medium (DMEM/F12 GlutaMAX, Penicillin/Streptomycin, 0.5% fatty acid free BSA). After 24 h of treatment with vehicle (exosome buffer), lean or obese iWAT adipocyte exosomes, cells were either washed with PBS and lysed for RNA isolation or further exposed to 10 µM isoproterenol for 6 h, to induce adipocyte browning.

Example 1.8: Phagocytosis Assay

To assess the functional impact of adipocyte exosomes on macrophages we performed a phagocytosis assay with pHrodo™ BioParticles® Conjugates (Thermo Scientific) according to the manufacturer's protocol. Briefly, $1 \times 10^5$ cells were seeded in a 96 well plate in serum free-medium and treated for 24 h with exosomes from lean vs. obese adipocytes. Following treatment, pHrodo particles were added and fluorescence was measured after 1.5 h of incubation. For normalization cells were fixed in 4% PFA and stained with DAPI.

Example 1.9: Fluorescent DiR Staining of Exosomes and In Vivo Tracking

For exosome uptake assays, fractions were stained using the near-infrared fluorescent cyanine dye 1,1'-dioctadecyl-3,3,3',3'-tetramethylindotricarbocyanine iodide (DiR, Biotium., Hayward, Calif.). Briefly, exosome fractions were incubated at 37° C. with DiR and washed in 1×PBS at 100,000 g for 130 min at 4° C. Exosome buffer treated with the same staining protocol served as a negative control. Stained exosomes and negative controls were re-suspended in exosome buffer and immediately used for cell uptake assays. After an incubation time of 24 h, medium was removed and cells were washed and fixed for 15 min in 4% PFA in PBS. Cells were counterstained with DAPI, mounted with Slow-fade GOLD mounting medium (Thermo-Fisher Scientific, USA) and analyzed using a ZEISS Axio Imager M2 microscope equipped with Cy7 filters. For in vivo tracking studies, 10 µg of DiR stained exosomes were diluted in 1×PBS and injected intraperitoneally into 12-week-old male C57BL/6J mice. DiR stained buffer was used as a negative control. To obtain exosome uptake kinetics, mice were sacrificed 4 or 24 h after exosome injection via $CO_2$ asphyxiation, shaved and frozen at −20° C. After embedding in O. C. T (TissueTeck), the torso was cryosliced along the axial planes at 100 µm intervals, and color and fluorescence images were recorded from each slice using a modified Leica cryotome (CM 1950, Leica Microsystems, Wetzlar, Germany), fitted with a motorized spectral illumination and multi-spectral CCD-based detection in epi-illumination mode[42]. Fluorescence images were captured at the peak emission wavelength of DiR. Each image stack was normalized against the average maximum fluorescence intensity of the image sequence, corresponding to the controls.

VIIA7 (Applied Biosystems). Target gene expression was normalized to suitable housekeeping genes (HPRT, Cyclophilin, 36b4) and relative expression levels were calculated according to Pfaffl[43]. Primer sequences are listed in Table 1.

TABLE 1

Primer information for real-time PCR analyses.

| Short name | Description | Forward Primer | Reverse Primer |
|---|---|---|---|
| 36b4/Rplp0 | Ribosomal protein, large P0 | AGATTCGGGATATGCTGTTGGC (SEQ ID No. 49) | TCGGGTCCTAGACCAGTGTTC (SEQ ID No. 50) |
| Arg | Arginase | CTCCAAGCCAAAGTCCTTAGAG (SEQ ID No. 51) | AGGAGCTGTCATTAGGGACATC (SEQ ID No. 52) |
| Cd63 | CD63 antigen | AGAGACCAGGTGAAGTCAGAG (SEQ ID No. 53) | AGTCTGTGTAGTTAGAAGCTCCA (SEQ ID No. 54) |
| Clec10a | C-type lectin domain family 10 member A | CTCTGGAGAGCACAGTGGAG (SEQ ID No. 55) | ACTTCCGAGCCGTTGTTCT (SEQ ID No. 56) |
| Cyc A | Cyclophilin A | ATGGTCAACCCCACCGTGT (SEQ ID No. 57) | TTTCTGCTGTCTTTGGAACTTTGTC (SEQ ID No. 58) |
| Fizz1/Retnla | Found in inflammatory zone -1/resistin like alpha | CCCTCCACTGTAACGAAGACT (SEQ ID No. 59) | CAGTGGTCCAGTCAACGAGT (SEQ ID No. 60) |
| Nos2 | Nitric oxide synthase 2 | CCCCGCTACTACTCCATCAG (SEQ ID No. 61) | CCACTGACACTTCGCACAAA (SEQ ID No. 62) |
| Ppargc1a | Peroxisome proliferator-activated receptor gamma, coactivator 1 alpha | AGCCGTGACCACTGACAACGAG (SEQ ID No. 63) | GCTGCATGGTTCTGAGTGCTAAG (SEQ ID No. 64) |
| Ucp1 | Uncoupling protein 1 | GGCCTCTACGACTCAGTCCA (SEQ ID No. 65) | TAAGCCGGCTGAGATCTTGT (SEQ ID No. 66) |

Example 1.10: Gene Expression Analysis

RNA from cells was extracted using RNeasy kits, RNA from adipose tissue was extracted using RNeasy Lipid kits according to manufacturer's instructions (Qiagen). Total RNA (1 µg) was reversely transcribed using a QuantiTect kit (Qiagen). Quantitative real-time PCR was performed using SYBR® MasterMix (Thermo-Fisher Scientific, USA) on the Example 1.11: Transcriptome Analysis The Agilent 2100 Bioanalyzer was used to assess RNA quality and only high quality RNA (RIN>7) was used for microarray analysis. Total RNA (30 ng) was amplified using the Ovation Pico WTA System V2 in combination with the Encore Biotin Module (Nugen). Amplified cDNA was hybridized on Affymetrix Mouse Gene ST 2.0 arrays. Staining and scanning (GeneChip Scanner 3000 7G) were done according to the Affymetrix expression protocol including minor modifications as suggested in the Encore Biotin protocol. Expression console (v.1.4.1.46, Affymetrix) was used for quality control and to obtain annotated normalized Robust Multi-array Average (RMA) gene-level data using standard settings with median polish and sketch-quantile normalisation.

Example 1.12: Filter Aided Sample Preparation (FASP) for Mass Spectrometric Analysis Samples were diluted to 100 µl with 50 mM ammonium bicarbonate (ABC) followed by cysteine reduction with 10 µl of 100 mM dithiothreitol for 30 minutes at 60° C. After cooling the samples to room temperature, the samples were diluted 2-fold with 8 M urea in 0.1 M Tris/HCl pH 8.5 and cysteines were alkylated with 10 µl of 300 mM iodoacetamide for 30 min at room temperature in the dark. Samples were centrifuged on a 30 kDa cut-off filter device (Pall GmbH Laboratory, Dreieich, Germnay) and washed three times with 8 M urea in 0.1 M Tris/HCl pH 8.5 and twice with 50 mM ABC. Flow-through solutions were discarded. Denatured proteins on the filter were digested in 70 μl of 50 mM ABC for 2 h at room temperature using 1 μg Lys-C (Wako, Neuss, Germany) and for additional 16 h at 37° C. using 2 μg trypsin (Promega, Madison, Wis.). Peptides were collected by centrifugation at 14,000 g for 2 minutes and filters were again eluted with 20 μl 50 mM ABC/2% acetonitrile (ACN). Combined eluates were acidified with 0.5% trifluoroacetic acid (TFA) and stored at −20° C.

Example 1.13: Mass Spectrometric Analysis

Approximately 0.5 μg of every sample were automatically injected and loaded onto the trap column (300 μm i.d.×5 mm, packed with Acclaim PepMap100 C18, 5 μm/100 Å; LC Packings) at a flow rate of 30 μl/min in 5% ACN/0.1% formic acid (FA). After 5 minutes, the peptides were eluted from the trap column and separated on the analytical column (PepMap, 15 cm, 75 μm i.d., 3 μm/100 Å pore size, LC Packings) by a 135 min gradient from 7% to 32% ACN in 0.1% FA at a flow rate of 300 nl/min followed by a short gradient from 32% to 93% ACN in 0.1% FA in 5 min. Between each sample, the gradient was set back to 7% ACN in 0.1% FA and left to equilibrate for 20 minutes. From the MS pre-scan, the 10 most abundant peptide ions were selected for fragmentation in the linear ion trap if they exceeded an intensity of at least 200 counts and if they were at least doubly charged, with a dynamic exclusion of 60 seconds. During fragment analysis a high-resolution (60,000 full-width half maximum) MS spectrum was acquired in the Orbitrap with a mass range from 300 to 1500 Da.

Example 1.14: Glucose Tolerance Tests (GTT) after Exosome Injection

Male C57BL6/J animals (12-14 weeks of age and an average bodyweight of 27 grams; were fasted for 7 hours before receiving an intraperitoneal (ip) glucose bolus of 1.7 mg per g body weight. Blood glucose was measured at 0, 15, 30, 60, and 120 min after glucose administration using Freestyle Lite test strips and Freestyle Freedom Lite glucometers (Abbott, Lake Bluff, Ill.). Four hours prior to the glucose injection, 10 μg of freshly prepared eWAT exosomes from lean and obese mice or vehicle (100 μl of PBS diluted exosome buffer) were injected ip (n=25 for vehicle controls, n=16 for lean eWAT exosome injection, n=13 for DIO eWAT exosome injection).

Example 1.15: Statistical Analyses

Data are reported as mean values±standard error of the mean (SEM) of at least three independent experiments. Statistical differences were calculated as indicated in the respective figure captions. P values less than 0.05 were regarded as statistically significant. Statistical analyses of cellular experiments were performed with Prism 6.0 (GraphPad Software, Inc, La Jolla, USA). Statistical analyses of transcriptome data were performed by utilizing the statistical programming environment R (R Development Core Team[44]) implemented in CARMAweb (CARMAweb version 1.5.18—uses R version 2.11.0 together with Bioconductor version 2.6; 45 Heatmaps were generated with CARMAweb. Pathway analyses were generated through the use of QIAGEN's Ingenuity Pathway Analysis (IPA®, QIAGEN Redwood City, www.qiagen.com/ingenuity). P-values are indicated in the graphics as follows: $p<0.05$ (*), $p<0.01$ () $p<0.001$ (*).

Example 1.16: EV Isolation from Human Adipose Tissue and their Characterization

In the following example, EVs preferably comprise exosomes to the highest amount: The findings were also translated into humans, where adipocytes, stromal vascular fraction (SVF) and serum from adipose tissue (AT) are obtained from liposuction patients (n=11) with different BMIs ranging from 18 to 37 (FIG. 11). Samples are then washed in DMEM/F12 and stored in medium over night at 4° C. Before digestion, samples are brought to room temperature and washed with PBS. Samples are digested using 0.075% Collagenase IV (Thermo Fisher Scientific, USA) with 1% BSA for 20 min and subsequently passed through a 100 μM mesh. Adipocytes are separated from the stromal-vascular fraction (SVF) by centrifugation at 100 g for 10 min. The adipocyte layer was then carefully isolated and further incubated in medium (DMEM 4.5 g/l glucose, with 0.2% BSA) for 2 h at 37° C. in a humidified atmosphere. After the incubation time, cell culture media were collected and secreted exosomes were isolated by differential centrifugation. Media were initially centrifuged for 10 min at 1000 g to remove debris and broken cells, followed by a 30 min step at 10,000 g to remove remaining fragments. Hereafter, exosomes were spun down at 100,000 g for 70 min, washed in 1×PBS and centrifuged again at 100,000 g for 70 min. All centrifugation steps were carried out at 4° C. Exosome enriched fractions were re-suspended in exosome buffer (0.25 M Sucrose, 10 mM Tris-HCl, 1 mM EDTA, 140 mM NaCl, pH 7.4, supplemented with EDTA free complete mini protease inhibitor tablets (Roche, Basel, Switzerland). Exo-Spin™ cleanup of isolated EVs was performed according to manufacturers' instructions.

Further, dot blot analysis was performed. Hereto, EVs were further isolated from serum samples of two random patients (IDs: 564 and 565). Purity and presence of classical exosome markers was tested using specific antibodies against GM1 (HRP-conjugated cholera-toxin B subunit for gangliosid M1 detection from Thermo-Fisher Scientific, USA) as well as CD63 and CD9 (Bioss, Inc., USA). Prior to antibody incubation, adipocyte EVs, SVF EVs and serum EVs were dot-blotted at RT onto nitrocellulose membranes (Whatman) using a MiniFold SpotBlot system (Whatman, GE Healthcare, Little Chalfont, UK). Dot densities were determined using ImageJ software (Rasband, W. S., ImageJ, U. S. National Institutes of Health, Bethesda, Md., USA) (FIG. 12A).

Additionally, dynamic light scattering (DLS) as known in the art as well as transmission electron microscopy to verify the presence and appearance of exosomes in our isolated fractions as described in Example 1.3 was performed (FIGS. 12 B and C).

Example 1.17: EV Isolation for Antigen Generation Using SGBS-EVs and their Characterization In the following figure, EVs preferably comprise exosomes to the highest amount: First, EVs need to be isolated from differentiated human Simpson Golabi Behmel (SGBS) cell line, closely resembling human adipose tissue. Hereto, SGBS cells are grown in SGBS growth medium to confluence. Differentiation is initiated by incubating the cells in differentiation medium I for 4 days. At day 4 the medium is replaced by serum free differentiation medium II and the cells are incubated until day 12. After the incubation time, cell culture media were collected and secreted exosomes were isolated by differential centrifugation. Media were initially centrifuged for 10 min at 1000 g to remove debris and broken cells, followed by a 30 min step at 10,000 g to remove remaining fragments. Hereafter, exosomes were spun down at 100,000 g for 70 min, washed in 1×PBS and centrifuged again at 100,000 g for 70 min to enrich EVs. All centrifugation steps were carried out at 4° C. Exosome enriched fractions were re-suspended in exosome buffer (0.25 M Sucrose, 10 mM Tris-HCl, 1 mM EDTA, 140 mM NaCl, pH 7.4, supplemented with EDTA free complete mini protease inhibitor tablets (Roche, Basel, Switzerland).

Western Blot analysis was also performed using isolated EVs from SGBS cells. Blots were immunostained using antibodies against the EV surface markers TSG101, Alix, CD9, CD63, CD81 and the endoplasmatic reticulum-protein Calnexin as negative control. Antibodies were purchased from Thermo Fisher Scientific, USA (TSG101), BioLegend, USA (Alix and CD81) or Santa Cruz, USA (CD9 and CD63) (FIGS. 13 A, B and C).

Example 1.18: Mouse Immunization with Isolated EVs

In the following figure, EVs preferably comprise exosomes to the highest amount: First, immunization and boosting of mice (n=1) and rats (n=2) with 10 µg of isolated EVs occurs. Then, spleen cells from rats and mice were harvested, B-cells were isolated and fused with immortal myeloma cells to generate hybridomas. Selection of antibody producing hybridoma cell clones in HAT media is then followed, before isolation of antibody containing supernatants occurs.

Example 1.19: Screening for Adipocyte EV Specific Antibodies

In the following figure, EVs preferably comprise exosomes to the highest amount: After immunization (see Example 1.18) a two-step antibody screening (96 well format) is established by applying a first step screening and a second step screening. The first step screening comprises that each antibody containing hybridoma supernatant is applied on: Differentiated SGBS cells (first positive selection) and HepG2 cells (first negative selection). The second step screening comprises that each selected antibody from the first screening is applied on: Differentiated SGBS cells (verification of the first selection) and undifferentiated SGBS cells (second negative selection) (FIG. 14).

Example 1.20: Specificity Testing and Further Selection for Adipocyte EV Specific Antibodies In the following figure, EVs preferably comprise exosomes to the highest amount: After screening for adipocyte EV specific antibodies, where 5 clones were selected (14H5, 15G1, 18G1, 23A11 and 29H2) dot blot analysis was performed. For dot blot analyses EVs from SGBS cells (SGBS EVs), EVs from HepG2 cells (HepG2 EVs), EVs from the adipocyte fraction of human liposuction samples (hAT EVs), EVs from blood serum of the same liposuction patient (hSerum EVs) as well as cell lysates from SGBS and HepG2 cells were spotted on nitrocellulose membranes: 2 µg SGBS EVs, HepG2 EVs, and hAT EVs, 10 µg for said cell lysate sample and 10 µg for said serum EVs. Spotted membranes were incubated with 5 selected antibody clones (14H5, 15G1, 18G1, 23A11 and 29H2). The presence of loaded protein (loading controls) was proven by Ponceau staining (FIG. 15).

Example 1.21: Target Identification by Mass Spectrometry

In the following figure, EVs preferably comprise exosomes to the highest amount: Target identification by mass spectrometry according to the recommendation of the International Working Group for Antibody Validation (Uhlemetal, Nature Methods 2016) was performed. First, immunoprecipitation (IP) of SGBS cell EVs using antibody containing primary supernatants bound to subclass-specific antibodies, which are bound to CNBr-activated sepharose beads, was applied (FIG. 16A). Elute bound epitopes were then prepared for mass spectrometry LTQ Orbitrap XL (see Example 1.13).

Target verification using purified monoclonal antibodies from stabilized clones (23A11, 15G1 and 14H5) were also used in another IP of SGBS cell EVs. This time the purified antibodies were directly bound to CNBr-activated sepharose beads and there was no subclass-specific antibody. Elute bound epitopes were then prepared for mass spectrometry LTQ Orbitrap XL again. Purified antibodies from stabilized monoclonal antibody producing clones (23A11, 15G1 and 14H5) were then reinvestigated via mass spectrometry for target verification (FIG. 16B).

Example 1.22: Antibody Characterization

In the following figure, EVs preferably comprise exosomes to the highest amount: For the first dot blot analyses regarding antibody 23A11 the following extracellular vesicles (EVs) and cell or tissue lysate samples were spotted on nitrocellulose membranes: SGBS cells; adipocyte fraction of human liposuction samples (hAT) of three different patients with different body mass indices (Patient 1: 19.6, patient 2: 23.3, patient 3: 28.1); blood serum (hSerum) of three different liposuction patients with different body mass indices (Patient 1: 19.6, patient 2: 23.3, patient 3: 28.1), HepG2 cells, Caco2 cells, Panc1 cells, Saos2 cells, MCF-7 cells, primary human skeletal muscle cells (hSkMC), HUVEC cells, blood cells, peripheral blood mononuclear cells (PBMC) and stromal vascular fraction (SVF) of human adipose tissue (FIG. 17). Spotted amounts were 2 µg for cellular and tissue derived EVs, 10 µg for lysates, 20 µg for serum EVs.

For the second and the third dot blot analysis regarding to antibody 15G1 (FIG. 18) and regarding to antibody 14H5 (FIG. 19) the following extracellular vesicles (EVs) and cell or tissue lysate samples were spotted on nitrocellulose membranes again: SGBS cells; adipocyte fraction of human liposuction samples (hAT) of three different patients with different body mass indices (Patient 1: 19.6, patient 2: 23.3, patient 3: 28.1), blood serum (hSerum) of three different liposuction patients with different body mass indices (Patient 1: 19.6, patient 2: 23.3, patient 3: 28.1), HepG2 cells, Caco2 cells, Panc1 cells, Saos2 cells and MCF-7 cells. Spotted amounts were 2 µg for cellular and tissue derived EVs, 10 µg for lysates, 20 µg for serum EVs.

Example 2: Results

Example 2.1: Adipocyte Exosomes Carry Distinct Membrane Markers

Figure 1:
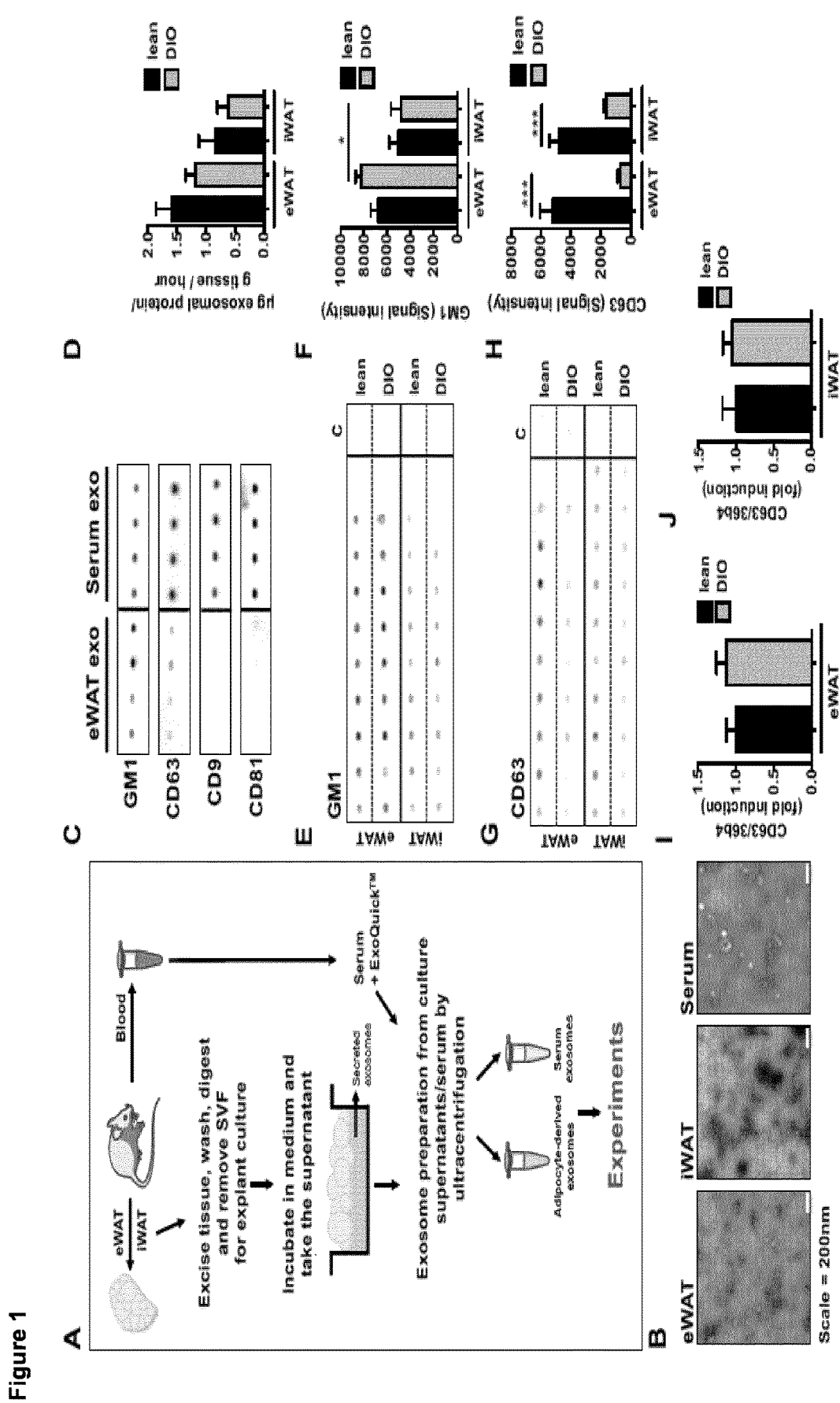
FIG. 1: Similar release rates but differential organ-specific membrane protein profiles in adipocyte and serum exosomes from lean and obese mice.

Exosome isolation protocols are mainly described for cell culture supernatants or biological fluids[16]. Only few reports exist for adipose tissue explant samples[17, 18, 19, 20], and the majority of these studies describe exosome isolation protocols for visceral adipose tissue with retaining stromal vascular fractions (SVF). The SVF includes several exosome secreting cell types, such as mesenchymal stem cells, endothelial cells, fibroblasts and a variety of immune cells[21]. In contrast to these studies, we established here a robust protocol to isolate exosomes from the pure adipocyte fraction of tissue explants of inguinal white adipose tissue (iWAT) and epididymal white adipose tissue (eWAT) that excludes the SVF (FIG. 1A). We further improved standard precipitation based serum exosome isolation procedures (FIG. 1A) to reduce contamination with non-exosomal serum proteins (FIGS. 6A and B). Transmission electron microscopy of isolated eWAT—(FIG. 1B, left panel), iWAT—(FIG. 1B, middle panel) and serum exosomes (FIG. 1B, right panel) of mice reveals the typical cup-shaped and double-membrane structure with a size of approximately 30-120 nm. To corroborate the exosomal identity, we immuno-stained for the presence of currently known exosomal selection markers such as the tetraspanins CD9, CD63 and CD81[16]. In addition, Choleratoxin B (CTB) was used to stain ganglioside M1 (GM1) positive lipid rafts, which are enriched in exosomal membranes[22]. Serum exosomes were isolated from lean mice, and stain highly positive for all exosomal markers investigated (FIG. 1C, right panel). In contrast, exosomes from eWAT adipocytes display strong staining for GM1, weak staining for CD63 and no staining for CD81 and CD9 (FIG. 1C), indicating differential surface expression profiles for adipocyte and serum exosomes.

Example 2.2: Adipocyte Exosome Secretion Rates Correlate with Adipose Tissue Mass To compare exosomal secretion rates from adipose tissue in response to metabolic challenges, we isolated adipocyte exosomes from eWAT and iWAT of chow-fed lean and high fat diet induced obese (DIO) mice that differed greatly in body weight (mean body weights±SEM: lean mice 33.26 g±0.20 g; DIO mice 47.48 g±0.79 g, p<0.0001). By quantifying total exosomal protein contents (FIG. 1D), we found similar exosome secretion rates from iWAT (p=0.15) and eWAT (p=0.20) in lean compared to obese mice. GM1 staining, although independent from the body weight, was higher in eWAT compared to iWAT exosomes of obese mice (FIGS. 1E and F). Interestingly, we detected significantly higher CD63 signal intensities in lean vs. obese exosomes for both eWAT and iWAT (FIGS. 1G and H), indicating that the amount of exosomal CD63 depends on the state of adiposity and/or diet. Notably, unchanged Cd63 mRNA levels in lean and DIO eWAT (FIG. 1I) and iWAT tissue samples (FIG. 1J) suggest a selected enrichment of CD63 in adipocyte exosomes. Body weight had no effect on serum exosome quantities or exosomal marker expression (Supplemental FIG. 1C-E). Overall, similar secretion rates from lean and obese adipocytes suggest a direct correlation between circulating adipocyte derived exosome concentrations and overall fat mass.

Example 2.3: Dietary Interventions Elicit Unique Exosome Proteome Profiles

To assess qualitative changes in exosomes undergoing a metabolic challenge, we isolated exosomes from eWAT and iWAT of lean chow-fed mice, DIO mice and previously obese mice that underwent a 9-day caloric restriction (CR) by switching their HFD to one pellet of chow diet (approx. 1 g) per mouse per day (FIGS. 7A and B). Proteome analyses revealed distinct protein signatures in adipocyte exosomes depending on the tissue of origin (iWAT vs. eWAT) and the dietary intervention (lean vs. DIO vs. CR) (FIG. 2A). Venn diagrams in FIG. 2B display the total numbers of eWAT and iWAT exosomal proteins detected in each dietary group. Total protein recovery rates following mass spectrometry were slightly higher in eWAT (detected proteins: lean: 931, DIO: 1108, CR: 1002) than in iWAT (detected proteins: lean: 749, DIO: 772, CR: 754) exosomes. Statistical analyses revealed 198 proteins in eWAT and iWAT that are differentially regulated by at least one dietary condition, with a broad overlap of 136 proteins in both tissue types (FIG. 2C). KEGG pathway enrichment analyses identifies 21 (eWAT) and 27 (iWAT) enriched pathways that are mainly assigned to lipid metabolism (FIG. 2D, pathways labeled with numbers 1-6), inflammation (FIG. 2D, pathways labeled with numbers 7-11), changes in membrane lipid metabolism (FIG. 2D, pathways labeled with numbers 12-14) and others (pathways 15-23), including diabetic complications (pathway number 15) and cancer (pathways 17-19). Pathway specific regulations were stronger and proteins more up-regulated in iWAT compared to eWAT exosomes isolated from mice undergoing dietary challenges (DIO, CR), compared to lean mice (FIG. 2E). Overall, these findings suggest that environmental conditions such as nutrition and body composition are reflected by the adipocyte exosome proteome.

Example 2.4: Adipocyte Exosomes Represent the Metabolic State of the Tissue of Origin To assess whether adipocyte exosomes provide a metabolic snapshot of the secreting tissue of origin, we compared the proteomes of eWAT exosomes from lean and obese mice with proteomes of eWAT tissue lysates and serum. Based on our assumption that adipocyte exosomes are secreted to the blood stream, we hypothesized that the comparison of eWAT exosomes with serum exosomes should reveal a significant overlap of proteins. Total protein recovery depended on the sample matrix and was slightly higher in eWAT tissue lysates (1125 detected proteins) compared to eWAT exosomes (793 detected proteins). In contrast, protein recovery was rather low in serum-derived exosomes with only 257 detected proteins. Despite lower recovery rates in serum, we found an overlap of 65 detected proteins in all conditions (FIG. 3A). Interestingly, among these 65 proteins, we identified adiponectin, an adipose tissue specific protein involved in the development of metabolic diseases (FIG. 3B). We next compared exosomal proteins with significantly regulated expression upon a dietary challenge (lean vs. DIO) and found an overlap of 36 proteins between eWAT exosomes and eWAT tissue, but no overlap between eWAT exosomes, eWAT tissue and serum exosomes (FIGS. 3C and D). Spearman rank correlation testing confirmed a highly significant association between tissue lysates and eWAT exosomes, indicating that eWAT exosomes reflect the metabolic condition of the adipose tissue (FIG. 3E). In contrast, the comparison between eWAT exosomes and serum exosomes revealed no significant association (FIG. 3F). KEGG pathway enrichment analyses of 482 (eWAT exosomes) and 144 (eWAT tissue lysates) differentially regulated proteins demonstrated a significant enrichment of general metabolic pathways as well as pathways involved in lipid metabolism, complement regulation and non-alcoholic fatty liver disease (manually selected from 53 exosome specific and 26 tissue specific pathways) (FIG. 3G). Importantly, enrichment tests revealed a more pronounced overrepresentation of pathways in eWAT exosomes compared to eWAT tissue lysates, suggesting that adipocyte exosomes depicted a more accurate footprint of the metabolic state of adipocytes compared to tissue biopsies (FIG. 3H). This is in line with previous findings demonstrating an enrichment of distinct RNAs relative to the originating cells[23]. Overall, the presence of adipose tissue specific proteins in serum exosomes provides first evidence that adipocyte exosomes are indeed secreted into the circulation.

Example 2.5: Adipocyte Exosomes Specifically Home in on Distinct Target Organs

We next aimed to elucidate whether circulating adipocyte exosomes accumulate in specific tissues. Lean mice were treated with an intraperitoneal (ip.) bolus injection of eWAT (also called gWAT) exosomes that were preloaded with the lipophilic near-infrared fluorescent cyanine dye DiR, and sacrificed 4 or 24 h after injections. Subsequent cryo-slicing of the whole murine torso along the axial planes followed by automated fluorescence analysis of each slice revealed minor background staining in dye injected control mice (FIG. 4A) and a clear organ specific delivery of DiR by eWAT exosomes 4 hours after injection (FIG. 4B). The signal was highest in the pancreas>gallbladder> eWAT=spleen>kidney. No signal was found in iWAT and muscle. After 24 hours, DiR was detected in the pancreas>gallbladder>liver>eWAT=spleen>kidney>muscle, while iWAT was still negative (FIG. 4C). Organ specific adipocyte exosome delivery is corroborated by comparing the organotrophic distribution of adipocyte exosomes and pancreatic cancer derives exosomes; 4 hours after injection, the DiR-delivery pattern of exosomes isolated from Panc02 pancreatic cancer cells displayed lower uptake into the liver and early uptake into the muscle, compared to the adipocyte exosomes (FIG. 4D).

The targeted delivery of eWAT exosomes to metabolically active target organs such as liver, pancreas and eWAT directed us towards assessing a potential role of adipocyte exosomes in glucoregulation. However, in an intraperitoneal glucose tolerance test (ipGTT), we could not detect any significant differences in glucose excursion when mice were pre-injected with eWAT exosomes from lean or obese mice (FIG. 8).

Example 2.6: Inflammatory miRNAs Signatures are Enriched in Adipocyte Exosomes of Obese Mice To better specify how adipocyte exosomes could affect distinct target organs, we isolated and compared exosomal miRNA contents from eWAT adipocytes of lean and obese mice. Micro RNAs (miRNAs) are regulators of gene expression, and exosomal transfer of miRNAs represents a mechanism of gene expression control across cells and tissues[24]. We found 53 miRNAs significantly deregulated between groups (t-test p-value<0.05) and 31 significantly de-regulated miRNAs after additional Benjamini Hochberg correction (false discover rate (FDR)<10%), as displayed in Table 2 and FIG. 9. Although macrophage containing SVF have been removed from the adipose tissue before exosome isolation, we found numerous miRNAs associated with pro- and anti-inflammatory signaling (Table 2 with references). Obese eWAT adipocyte exosomes further contained miR-NAs with a purported role in adipose tissue browning or adipogenesis (Table 2) that point towards a paracrine or endocrine role in distinct target organs.

TABLE 2

Functional analysis of miRNAs from eWAT adipocyte exosomes.

| miRNA from adipocyte exosomes | FC (obese vs. lean | t-test p-value | Benjamini Hochberg FDR | Metabolic impact | Predicted targets |
|---|---|---|---|---|---|
| mmu-miR-31-5p | 7.61 | 0.01012 | 0.06546 | Enhancer of adipogenesis[R 46] | — |
| mmu-miR-139-3p | 5.66 | 0.00066 | 0.01827 | Inhibitor of adipogenesis*[47] | Notch1 * IRS1 * |
| mmu-miR-342-5p | 4.99 | 0.01664 | 0.09567 | Activation of inflammatory macrophages in atherosclerosis[48] | AKT1 |
| mmu-miR-504-5p | 4.41 | 0.01439 | 0.08510 | Unknown | — |
| mmu-miR-342-3p | 4.36 | 0.00321 | 0.04401 | Enhancer of adipogenesis[H 49] Increased in WAT of DIO[50] and Lep[ob] mice[51] | CtBP2 |
| mmu-miR-335-5p | 4.19 | 0.00669 | 0.05772 | Enhancer of adipogenesis, responsive to leptin, resistin, TNF-α, and IL-6[H 52] | — |
| mmu-miR-222-3p | 4.09 | 0.00025 | 0.01368 | Mitochondrial dysfunction and ROS**[53] Increased in WAT of DIO mice[50] | Pgc1α |
| mmu-miR-296-5p | 3.99 | 0.00986 | 0.06546 | Hepatocyte lipoapoptosis[H 54] | PUMA HGS |
| mmu-miR-376a-3p | 3.37 | 0.00286 | 0.04401 | Decreased in serum of obese individuals[H 55] | — |
| mmu-miR-382-5p | 2.98 | 0.00656 | 0.05772 | Unknown | — |
| mmu-miR-142-3p | 2.43 | 0.00091 | 0.01891 | Anti-inflammatory[56] Macrophage polarization[57] Increased in WAT of DIO mice[50] Increased in serum of obese individuals[H 58] | HMGB1 |
| mmu-miR-379-5p | 2.12 | 0.00923 | 0.06366 | Increased in WAT of DIO mice[56] Increased in livers of db/db mice[59] Hepatic lipid homeostasis[59] | — |
| mmu-miR-744-5p | 2.10 | 0.00590 | 0.05772 | Unknown | — |
| mmu-miR-139-5p | 1.94 | 0.01087 | 0.06816 | Inhibitor of adipogenesis[47] | Notch1 |

TABLE 2-continued

Functional analysis of miRNAs from eWAT adipocyte exosomes.

| miRNA from adipocyte exosomes | FC (obese vs. lean) | t-test p-value | Benjamini Hochberg FDR | Metabolic impact | Predicted targets |
|---|---|---|---|---|---|
| mmu-miR-18a-5p | 1.79 | 0.00383 | 0.04401 | Unknown | — |
| mmu-miR-146b-5p | 1.77 | 0.00363 | 0.04401 | Enhancer of adipogenesis [60] Increased in WAT of DIO mice [50] Increased in human adipocytes in response to IL-6 and TNF[H 61] | SIRT1 |
| mmu-miR-27b-3p | 1.61 | 0.00056 | 0.01827 | Anti-adipogenic** [62] Suppressor of WAT browning [63] | PPARγ Prdm16 |
| mmu-miR-24-3p | 1.58 | 0.00156 | 0.02689 | Hepatic lipid accumulation [64] Decreased in RYGB patients[H 65] | Insig1 |
| mmu-miR-26a-5p | −1.59 | 0.00528 | 0.05465 | BrowningH [66] Decreased in livers of obese mice and humansH [67] Enhancer of insulin sensitivity [67] | ADAM17 |
| mmu-miR-10a-5p | −1.60 | 0.00881 | 0.06289 | Anti-inflammatory[R], Glucose homeostasis[R 68] | Il6, Tnf |
| mmu-miR-143-3p | −1.62 | 0.00021 | 0.01368 | Enhancer and inhibitor of adipogenesis (stage dependent) [69] Enhancer of adipogenesis [70]** Enhancer of adipogenesis [71] Obesity associated insulin resistance [72] | Map2k5 ERK5 Pref-1 Orp8 |
| mmu-miR-101a-3p | −1.67 | 0.00007 | 0.01368 | Cytokine-mediated β-cell dysfunction [73] | Onecut2 |
| mmu-miR-328-3p | −1.67 | 0.00813 | 0.06179 | Repressed in palmitate-induced ER stress [74] | — |
| mmu-miR-181a-5p | −1.67 | 0.00071 | 0.01827 | Enhancer of adipogenesis[P 75] Decreased expression in monocytes of obese individuals[H 76] | Tnfα |
| mmu-miR-126a-3p | −1.71 | 0.00139 | 0.02621 | Reduced in plasma of T2D patient[H 77] | — |
| mmu-miR-322-5p | −1.74 | 0.00089 | 0.01891 | Insulin secretion from murine β-cells [78] | Stxbp1 |
| mmu-miR-497-5p | −1.83 | 0.00836 | 0.06179 | Increased during the progression of arteriosclerosis [79] | — |
| mmu-miR-150-5p | −2.40 | 0.00028 | 0.01368 | Negative regulator of adipose tissue browning [80] | Prdm16 Pgc1α |
| mmu-miR-218-5p | −2.53 | 0.00613 | 0.05772 | Inhibitor of insulin secretion from β-cells [78] | Stxbp1 |
| mmu-miR-345-5p | −2.53 | 0.00033 | 0.01368 | Unknown | — |
| mmu-miR-450a-5p | −2.61 | 0.00447 | 0.04869 | Unknown | — |

Functional analysis of 31 significantly deregulated miRNAs in eWAT adipocyte exosomes from lean (n = 5) and DIO (n = 5) mice. For statistical analyses the moderated limma t-test was applied in combination with the Benjamini-Hochberg correction for multiple testing.
Probe Sets with a False Discovery Rate (FDR) <10% and a fold change (FC) <1.5 were considered as significant.
[R] Shown for the *rattus norvegicus* analogue
[H] Shown for the human analogue
[P] Shown for the porcine analogue
* shown for the -5p sequence

Example 2.7: iWAT Adipocyte Exosomes are not Linked with Adipocyte Browning

In order to elucidate possible effects of adipocyte exosomes on adipocyte browning we treated primary subcutaneous adipocytes with iWAT exosomes from lean and obese mice but could not detect any effects on Ucp1 expression in response to exosome treatment (FIG. 5A, upper left panels). Cells treated with lean adipocyte exosomes displayed a significant down-regulation of Ppargc1 α compared to vehicle-treated control cells, but such differences vanish after treatment with DIO adipocyte exosomes. Stimulation with isoprotenerol 6 h post exosome treatment induced a clear increase of Ucp1 and Ppargc1α expression (FIGS. 10A and B). However, as confirmed in three independent experiments, the addition of iWAT exosomes did not affect Ucp1 expression (FIG. 5A, upper right panel). Co-treatment of isoprotenerol with iWAT exosomes from obese mice revealed a trend towards increased Ppargc1α expression (FIG. 5A, lower right panel).

Example 2.8: Adipocyte Exosomes Reveal Paracrine Effects on Macrophage Polarization The inflammatory miRNA signatures present in obese adipocyte exosomes prompted us towards investigating a possible role of adipocyte exosomes on macrophage polarity. DiR labeled exosomes from lean and obese eWAT are efficiently taken up by bone marrow derived M0 macrophages (BMDM) 24 h hours after treatment (FIG. 5B). Treatment of M0 macrophages with increasing concentrations of lean and obese eWAT derived exosomes had no effect on M1 or M2 marker expression (FIG. 5C, left panels). We next stimulated M0 macrophages with either interferon gamma (INF-γ) or interleukin 4 (IL-4) to induce polarization towards a pro-inflammatory M1 or anti-inflammatory M2 phenotype. INFγ induced M1 polarization was not affected by any exosome treatment (FIG. 5C, upper right panel). In contrast, exosomes from both lean and DIO eWAT donors decreased the expression of M2 markers Arg1, Clec10a and Fizz1 upon IL-4 treatment (FIG. 5C, three lower panels), suggesting that adipocyte derived exosomes can blunt the anti-inflammatory M2 response. Moreover, the addition of eWAT exosomes led to a slight but significant decrease of the phagocytotic activity of bone marrow derived macrophages (FIG. 5D). This effect appeared to be independent of the state of adiposity or nutritional status of the eWAT exosome donor.

To sensitively characterize exosome-mediated effects on M2 macrophages, we next analyzed whole genome gene expression of exosome treated macrophages. Treatment of M0 BMDM macrophages with adipocyte exosomes from lean and DIO mice resulted in 169 differentially expressed genes (FIG. 5E). Upstream regulator prediction revealed Map3K8 (Tpl2) and IKBKB as major nexus for the expression differences in macrophages treated with exosomes from obese adipocytes (Table 3). Interestingly, both putative upstream regulators were linked to the development of metabolic inflammation[25, 26, 27]. Besides Map3K8 and IKBKB, active Oncostatin M (OSM) may contribute to the regulation of several downstream genes involved in inflammatory responses (Table 3). Additional IL-4 stimulation resulted in a smaller set of 114 differentially regulated genes (FIG. 5F), but no predictions for activated or inhibited upstream regulators. Together, these finding suggest that adipocyte derived exosomes may serve as important paracrine mediators of adipose tissue homeostasis by regulating macrophage function and polarity.

TABLE 3

Upstream regulator analysis of vehicle treated bone marrow derived macrophages (BMDM) treated with 5 µg eWAT exosomes from lean or obese mice.

| | Upstream regulator | Predicted activation state | Activation z-score | p-value of overlap | Target molecules |
|---|---|---|---|---|---|
| Vehicle treated BMDM | Map3k8 | activated | 2.21 | 9.41E–04 | Ccl20, Ciita, Htra4, Il10, Tdrkh, Timeless |
| | IKBKB | activated | 2.16 | 2.47E–03 | Ccl2, Ccl20, Cdh13, HLA-A, Il10 |
| | OSM | activated | 2.18 | 3.99E–02 | Ccl2, Ccl20, HLA-A, Il10, SerpinB1 |

Gene expression data are derived from three independent BMDM and exosome preparations, respectively. The p-value of overlap depicts a ranking of physiological upstream regulators according to their p-values for the comparison of gene expression data after treatment with lean and obese exosomes (see FIG. 5E). Upstream regulators with a p-value of overlap<0.05 and an activation z-score>2 were considered as activated.

Example 2.9: Characterization of Human Adipocyte Derived EVs

In the following example, EVs preferably comprise exosomes to the highest amount: Purity and presence of classical exosome markers were tested using specific antibodies against GM1 as well as CD63 and CD9. Said antibodies bound to adipose derived EVs (upper lane), to SVF EVs (middle lane) and also to serum EVs (lower lane for CD63 and CD9) in both subjects (564 and 565) (FIG. 12A).

Additionally, dynamic light scattering (DLS) revealed that explant adipocytes from human liposuction samples release a population of vesicles ranging in size from 30 to 300 nm with an average size of 101.5±53.0 nm (FIG. 12B).

Representative transmission electron microscopy images of EVs isolated from human adipocytes from a liposuction sample of a patient revealed a typical cup-shaped and double-membrane structure with a size of approximately 40-180 nm. This reveals that EVs preferably comprises exosomes, since exosomes have a size of around 30-120 nm (FIG. 12C).

Example 2.10: Antigen (SGBS-EVs) Characterization

In the following example, EVs preferably comprise exosomes to the highest amount: Basic characterization of EVs isolated from cell culture media of differentiated SGBS cells using Western Blot analysis showed the detection of the typical marker enrichment in EVs compared to SGBS lysates. Blots were immunostained using antibodies against the EV surface markers TSG101, Alix, CD9, CD63, CD81 and the endoplasmatic reticulum-protein Calnexin as negative control (FIG. 13A).

Dynamic light scattering (DLS) revealed that differentiated SGBS cells release a population of vesicles ranging in size from 30 to 300 nm with an average size of 101.1±67.04 nm (FIG. 13B).

EVs show a typical round and cup-shaped morphology with a size of approximately 40-150 nm using representative transmission electron microscopy image of EVs isolated from differentiated SGBS cells. This reveals that EVs preferably comprises exosomes, since exosomes have a size of around 30-120 nm (FIG. 13C).

Example 2.11: Selection and Specificity Testing of Adipocyte EV Specific Antibodies In the following example, EVs preferably comprise exosomes to the highest amount: After the two-step antibody screening, where 5 clones (14H5, 15G1, 18G1, 23A11 and 29H2) were selected, dot blot analysis showed that three antibodies (23A11, 15G1 and 14H5; marked by brown boxes) had a highly specific binding to SGBS and hAT EVs and SGBS lysate as positive control. Weak signal was detected in human serum EV samples, which may represent the fraction of adipocyte secreted EVs. Antibodies (18G1 and 29H2; without box) failed to demonstrate organ specificity (FIG. 15).

Example 2.12: Target Identification

In the following example, EVs preferably comprise exosomes to the highest amount: After immunoprecipitation of SGBS cell EVs for mass spectrometry, also purified antibodies from stabilized monoclonal antibody producing clones (23A11, 15G1 and 14H5) were reinvestigated via mass spectrometry for target verification (FIG. 16B). For each antibody producing clone its specific antibody target was investigated. The antibody target of the antibody producing clones 15G1 and 14H5 is the amine oxidase, copper containing 3 protein (AOC3). AOC3 is mostly expressed in adipose tissue (AT). The antibody targets of the antibody producing clone 23A11 is Collagen Type VI alpha 1/2/3 (here as COL6A1/2/3), which according to the Human Protein Atlas is also highly expressed in adipose tissue in comparison to other organs such as liver, colon, pancreas etc.

Example 2.13: Antibody Characterization

In the following example, EVs preferably comprise exosomes to the highest amount: Spotted membranes, incubated with our selected antibody clone 23A11 demonstrating a weak positive signal in SGBS-EVs (used as antigen for mouse immunization), a weak positive signal in all hAT samples and a strong positive signal in hAT EV. No antibody binding was observed for EVs isolated from other human non-adipose tissue cell lines (liver, colon, pancreas, bone, breast or skeletal muscle cells), thus demonstrating that antibody 23A11 is specific for adipose derived EVs. A weak positive staining was observed for hSerum and hSerum EVs in combination with the absence of antibody binding to endothelial HUVEC EVs, blood cell lysates and PBMC lysates is indicative for the presence of circulating hAT EVs. Additionally, the incubation with a commercially available antibody (Santa Cruz: 172C2) against the top hit antibody target identified via mass spectrometry: Collagen Type VI alpha 1/2/3 (Col 6A1/2/3), demonstrating non-specific binding to non-adipose tissue derived EVs. Since the commercially available antibody was not generated through the process of exosome immunization in mice and rats, this might explain the fact that said antibody did not bind to hAT EVs and was cross reactive to other non-adipocyte EVs in comparison to antibody 23A11, which was generated through the process of exosome immunization (FIG. 17).

Spotted membranes incubated with our selected antibody clone 14H5 (FIG. 18) and 15G1 (FIG. 19) demonstrating a positive signal in SGBS-EVs (used as antigen for mouse immunization) and SGBS lysates and hAT EVs. No antibody binding was observed for HepG2 lysates or HepG2 EVs. Further, a positive signal in SGBS-EVs (used as antigen for mouse immunization) and SGBS lysates and hAT EVs, but no binding to lysates or EVs from other human non-adipose tissue cell lines (besides liver, also colon, pancreas, bone or breast).

Example 3: Discussion

Recent advances in protein biochemistry suggest that adipose tissue can secrete more than 600 potentially bioactive factors termed adipokines[28]. Here we provide evidence that adipocyte exosomes represent an additional and potentially more targeted route of conveying information between adipose tissue and target organs. Our data further demonstrate that adipocyte exosomes hold great promise as circulating biomarkers that visualize the metabolic and pathophysiological state of adipose tissue.

We here established a protocol for exosome isolation from the adipocyte fraction of the adipose tissue by removing the SVF. The latter is composed of a large variety of other cell types such as fibroblasts or endothelial and immune cells, which can make up to 60% of the adipose tissue[21]. Immune cells secrete high amounts of exosomes[29], which may conceal characteristic profiles of adipocyte-derived exosomes. We also avoided the addition of agents that stimulate stress dependent exosome release, namely hydrogen peroxide, insulin or palmitate[30, 31]. Accordingly, we isolated pure and un-stimulated exosomes from adipocytes of different fat pads from mouse with characteristic exosome features, as evidenced by typical cup-shapes and diameters in TEM and positive immunostaining for basic exosomal markers such as GM1 or CD63. The isolation of exosomes from human adipose tissue was also demonstrated. Adipose tissue samples were obtained from liposuction patients with different BMIs and the human adipocyte derived EVs (hAT EVs) were also characterized as having cup-shaped and double-membrane structure and were positive immunostained for basic exosomal markers such as GM1, CD63 and CD9. Thus, revealing that EVs preferably comprise exosomes to the highest amount.

Using our established isolation procedure, we here demonstrate that eWAT and iWAT fat pads of lean, DIO and CR mice release similar amounts of exosomes from their adipocyte fractions. Deng and coworkers[19] described higher secretion rates from whole obese adipose tissue explants from DIO and $Lep^{ob}$ mice compared to lean adipose tissue of WT controls. Whether the differences observed in adipose tissue exosome secretion rates in $Lep^{ob}$ mice result from the shift towards an increased number of inflammatory immune cells[32] and thus enhanced SVF exosome release remains to be determined. Our finding of a directly correlated adipocyte exosome release rate in response to fat pad mass nevertheless supports the notion that circulating adipocyte exosomes may be massively increased in a state of obesity.

Upon secretion, the fate of adipocyte exosomes remains obscure. A few articles have reported the tissue distribution of exogenously administered melanoma derived exosomes in vivo that pointed towards a rapid uptake into the liver, lung, kidney, and spleen[33, 34]. Similar to melanoma exosomes, we demonstrate rapid clearance of DiR labeled adipocyte exosomes from the blood. However, the organ distribution pattern differed profoundly, with highest and time-dependent accumulation of DiR in pancreas, gallbladder, liver and spleen. Surface markers residing on adipocyte exosomes may mediate such a selective accumulation pattern. For instance, distinct integrin patterns were recently described for the uptake of tumor-derived exosomes by organ-specific cells[6]. Our exosomal proteome contained a cluster of integrins from the integrin alpha and beta family, and their potential role in the organotrophic uptake of adipocyte exosomes warrants further study.

The selective uptake in metabolically active tissues suggests potential paracrine and/or endocrine functions of adipocyte exosomes. This hypothesis is supported by our finding that adipocyte exosomes contain functional miRNAs with a predicted function in adipogenesis, adipose tissue browning, and adipose tissue inflammation. Differential amounts of these miRNAs in exosomes from adipocytes of lean and obese mice further point towards a metabolic function. Unexpectedly, despite promising miRNA candidates we did not observe any browning in our cell culture system, using adipocyte exosomes from iWAT and primary inguinal adipocytes. Nonetheless, M2 macrophage polarization was blunted upon adipocyte exosome administration, suggesting a paracrine role in the etiology of obesity. A shift from an M2 to an M1 macrophage phenotype in adipose tissue is often considered as an early step in the development of low-grade systemic inflammation and glucose intolerance[35]. Although M1 macrophages were not directly affected by adipocyte exosomes, a reduced M2 response could shift the balance towards a more inflammatory phenotype. In line with this assumption, gene enrichment revealed Map3K8 (Tpl2) and its activator IKBKB as major upstream regulator of many of the differentially expressed genes in bone marrow derived macrophages treated with exosomes from lean or DIO derived eWAT adipocytes. Map3K8 is required for lipopolysaccharide (LPS) and Toll Like Receptor 4-mediated activation of the MAPK/ERK pathway in macrophages[36], and its ablation attenuated immune cell infiltration into the adipose tissue as well as obesity-associated metabolic dysfunction[26]. Co-culture studies revealed that Map3K8 in macrophages is importantly involved in the cross talk between adipocytes and macrophages that promotes inflammatory changes and alteration of insulin signaling in adipocytes[25]. Similarly, IKBKB especially in myeloid cells may link inflammation to obesity-induced insulin resistance[27]. Overall, our data suggest that adipocyte exosomes constitute paracrine effectors of macrophage polarization and thus adipose tissue inflammation.

Contrary to the effect of adipocyte exosomes on macrophage polarization, we did not detect systemic effects of intraperitoneally injected adipocyte exosomes on glucose tolerance. Deng et al. demonstrated that injection of adipose tissue exosomes from Lep$^{ob}$ mice but not WT mice resulted in significant alterations of glucose excursions following an ipGTT[19]. These discrepant findings may result from different dosing regimen (30 μg exosomes/mouse every 3 days for 21 days compared to one injection of 10 μg exosomes/mouse in our studies), the genetic background (Lep$^{ob}$ instead of DIO mice), or from a potentially stronger systemic impact of exosomes derived from the SVF fraction, which are efficiently removed in our adipocyte exosome isolation. Novel models with genetic disruption of adipocyte exosome secretion, their loading with bioactive molecules, or their organ specific uptake will help to clarify whether adipocyte exosomes impair systemic glucose control.

However, the main finding was the generation of adipocyte EV specific antibodies. Specificity testing revealed that three antibodies (23A11, 15G1 and 14H5) showed a highly specific binding to SGBS EVs and hAT EVs, which were isolated earlier from liposuction patients. Those three antibodies were organ-specific to adipose tissue derived EVs since non-specific binding to non-adipose tissue derived EVs (e.g. liver, colon, pancreas, bone and breast) was detected for all three antibodies. Target identification via mass spectrometry further showed the antibody targets for each clone, having COL6A1/2/3 as a target for clone 23A11 and having AOC3 as a target for clones 15G1 and 14H5, all targets being highly expressed in adipose tissue.

Since antibody 23A11 also binds adipose derived EVs in the serum (hSerum EVs) as well as EVs from adipocyte fraction of human liposuction samples (hAT), this reveals that EVs from serum have a similar protein profile compared to EVs from adipocyte fraction. Thus, antibody 23A11 may perfectly be used to isolate adipose derived EVs from a serum sample.

Strikingly, our exosomal proteome data demonstrate that adipocyte derived exosomes provide a valuable tool to assess the health status of adipocytes within their intact tissue context. Isolation of secreted adipocyte exosomes from the blood could therefore provide a "liquid biopsy" that mirrors the metabolic state of the adipose tissue. Specific markers for adipocytes such as adiponectin were identified in the serum exosome fraction, thereby providing clear evidence that adipocyte exosomes are released into circulation. However, despite an optimized protocol and reduced residual protein in serum exosomes, the recovery of adipose tissue specific proteins in our proteome analysis of serum exosomes was low, suggesting a relative underrepresentation of adipocyte exosomes in the serum exosome fraction. Nevertheless, enrichment of adipocyte exosomes from the blood, e.g. by specific surface marker antibodies, combined with increasingly cost-efficient omic technologies could serve as tailored personalized diagnostics of adipose tissue function. In this setting, adipocyte exosomes may help stratifying comorbidity risks in obese individuals by distinguishing healthy adipose tissue from yet-to-be-defined stages of adipose tissue inflammation and pathophysiology. The present invention can also be characterized by the following items:

1. Tissue-specific exosomes for use in a method of diagnosing, monitoring and/or predicting the risk for developing a metabolic disease in a subject, wherein said tissue-specific exosomes are preferably isolatable by an antibody capable of specifically binding to a tissue-specific exosomal surface marker, wherein said antibody comprises
   a) the following $V_H$ and $V_L$ domain CDRs having the amino acid sequence shown in SEQ ID Nos. 1 to 3 and 4 to 6;
   b) the following $V_H$ and $V_L$ domain CDRs having the amino acid sequence shown in SEQ ID Nos. 7 to 9 and 10 to 12;
   c) the following $V_H$ and $V_L$ domain CDRs having the amino acid sequence shown in SEQ ID Nos. 13 to 15 and 16 to 18.

2. The tissue-specific exosomes for use in a method according to claim 1, wherein monitoring comprises evaluating treatment efficacy and/or progression of the metabolic disease.

3. The tissue-specific exosomes for use in a method according to claim 1 or 2, wherein said tissue is selected from white and brown adipose tissue, liver tissue, pancreas tissue, bowel tissue, muscular tissue, stomach tissue, kidney tissue, hypothalamus tissue.

4. The tissue-specific exosomes for use in a method according to any one of the preceding claims, wherein said metabolic disease is selected from obesity, hyperglycaemia, insulin resistance, prediabetes, type 1 or type 2 diabetes, pancreatic hypertrophy, adipose tissue inflammation, adipose tissue browning, fatty liver disease (FLD), glycogen storage disease (GSD), galactosemia, lactose intolerance, fructose intolerance, sucrose intolerance, phenylketonuria (PKU), glutaric aciduria type 1, organic acidemia, lysosomal storage diseases, including lipid storage disorders, mucopolysaccharidoses, mucolipidoses, Systemic primary carnitine deficiency, (SPCD), haemochromatosis, and glycoproteinosis.

5. The tissue-specific exosomes for use in a method according to any one of the preceding claims, wherein said tissue-specific exosomes are isolated from a sample of the subject.

6. The tissue-specific exosomes for use in a method according to claim 5, wherein said sample is selected from a blood sample, a plasma sample, a serum sample, lymph, saliva, bile, feces, an organ or tissue biopsy, breast milk, urine sample, cerebrospinal fluid sample, and amniotic fluid.

7. The tissue-specific exosomes for use in a method according to claim 5 or 6, wherein said exosomes are isolated from the sample by contacting the sample with a binding molecule capable of specifically binding to said exosomes.

8. The tissue-specific exosomes for use in a method according to claim 7, wherein said binding molecule specifically binds to an exosomal surface marker.

9. The tissue-specific exosomes for use in a method according to any one of the preceding claims, wherein said method comprising detecting an exosomal biomarker indicative for said metabolic disease.

10. The tissue-specific exosomes for use in a method according to claim 9, wherein said biomarker is selected from a protein, peptide, and a nucleic acid, or lipid.

11. The tissue-specific exosomes for use in a method according to claim 10, wherein said nucleic acid is selected from a messenger RNA (mRNA), non-coding (nc-)RNAs (including anti-sense-RNAs, silencer RNAs, micro-RNAs (miRNAs), short hairpin RNAs (shRNAs), small interfering RNAs (siRNAs), repeat-associated small interfering RNA (rasiRNA), piwi-interacting RNAs (piRNA), Y RNA, ILong non-coding RNAs (long ncRNAs, IncRNA)), transfer RNAs (tRNA), ribosomal RNAs (rRNA), small nuclear RNA (snRNA), small nucleolar ribonucleic acid (snoRNA), spliced leader RNAs (SL RNA).

12. The tissue-specific exosomes for use in a method according to any one of the preceding claims, wherein the subject is a mammal, in particular a human, non-human primate, dog, cat, guinea pig, rabbit, rat or mouse.

13. Use of a tissue-specific exosomal surface marker for isolation of exosomes, wherein said tissue-specific exosomes are preferably isolatable by an antibody capable of specifically binding to a tissue-specific exosomal surface marker, wherein said antibody comprises
    a) the following $V_H$ and $V_L$ domain CDRs having the amino acid sequence shown in SEQ ID Nos. 1 to 3 and 4 to 6;
    b) the following $V_H$ and $V_L$ domain CDRs having the amino acid sequence shown in SEQ ID Nos. 7 to 9 and 10 to 12;
    c) the following $V_H$ and $V_L$ domain CDRs having the amino acid sequence shown in SEQ ID Nos. 13 to 15 and 16 to 18.

14. A binding molecule capable of specifically binding to a tissue-specific exosomal surface marker, preferably being an antibody, wherein (i) said antibody comprises,
    a) the following $V_H$ and $V_L$ domain CDRs having the amino acid sequence shown in SEQ ID Nos. 1 to 3 and 4 to 6;
    b) the following $V_H$ and $V_L$ domain CDRs having the amino acid sequence shown in SEQ ID Nos. 7 to 9 and 10 to 12;
    c) the following $V_H$ and $V_L$ domain CDRs having the amino acid sequence shown in SEQ ID Nos. 13 to 15 and 16 to 18,
or (ii) wherein said antibody competes for the same epitope as that recognized by the antibody of (i) and wherein the antibody can block the binding of the antibody of (i) by at least 20% compared with the affinity obtained in a control test performed in the absence of the competing antibody.

15. The binding molecule according to claim 14, wherein said tissue is selected from white and brown adipose tissue, liver tissue, pancreas tissue, bowel tissue, muscular tissue, stomach tissue, kidney tissue, hypothalamus tissue.

16. The binding molecule according to claim 14 or 15, wherein said binding molecule is an antibody, in particular a monoclonal or polyclonal antibody.

17. The binding molecule according to claim 16, wherein said monoclonal antibody is a chimeric, humanized or human antibody or antigen-binding fragment thereof.

18. A Kit for performing the method as defined in any one of claims 1 to 12, comprising means for detecting the presence of a tissue-specific exosomal surface marker and optionally means for isolating tissue-specific exosomes, wherein said tissue-specific exosomes are preferably isolatable by an antibody capable of specifically binding to a tissue-specific exosomal surface marker, wherein said antibody comprises
    a) the following $V_H$ and $V_L$ domain CDRs having the amino acid sequence shown in SEQ ID Nos. 1 to 3 and 4 to 6;
    b) the following $V_H$ and $V_L$ domain CDRs having the amino acid sequence shown in SEQ ID Nos. 7 to 9 and 10 to 12;
    c) the following $V_H$ and $V_L$ domain CDRs having the amino acid sequence shown in SEQ ID Nos. 13 to 15 and 16 to 18,
and detecting the presence of at least one exosomal biomarker indicative for a metabolic disease.

19. The kit according to claim 18, comprising a binding molecule capable of specifically binding to a tissue-specific exosomal surface marker.

20. An in vitro method of diagnosing or monitoring a metabolic disease in a subject or predicting the risk of a subject of developing a metabolic disease, comprising (i) isolating tissue-specific exosomes from a sample of the subject, wherein said tissue-specific exosomes are preferably isolatable by an antibody capable of specifically binding to a tissue-specific exosomal surface marker, wherein said antibody comprises
    a) the following $V_H$ and $V_L$ domain CDRs having the amino acid sequence shown in SEQ ID Nos. 1 to 3 and 4 to 6;
    b) the following $V_H$ and $V_L$ domain CDRs having the amino acid sequence shown in SEQ ID Nos. 7 to 9 and 10 to 12;
    c) the following $V_H$ and $V_L$ domain CDRs having the amino acid sequence shown in SEQ ID Nos. 13 to 15 and 16 to 18,
and (ii) determining the presence of at least one biomarker in said exosomes that is indicative for a metabolic disease and/or its co-morbidities or for the risk of developing a metabolic disease.

21. The in vitro method according to claim 20, wherein step (i) comprises contacting the sample with a binding molecule capable of specifically binding to a tissue-specific exosomal biomarker.

22. A method for isolating tissue-specific exosomes from a sample, said method comprising a step of contacting said sample with a binding molecule capable of specifically binding to a tissue-specific exosomal surface marker, preferably being an antibody, wherein (i) said antibody comprises,
    a) the following $V_H$ and $V_L$ domain CDRs having the amino acid sequence shown in SEQ ID Nos. 1 to 3 and 4 to 6;
    b) the following $V_H$ and $V_L$ domain CDRs having the amino acid sequence shown in SEQ ID Nos. 7 to 9 and 10 to 12;
    c) the following $V_H$ and $V_L$ domain CDRs having the amino acid sequence shown in SEQ ID Nos. 13 to 15 and 16 to 18.

23. The binding molecule according to any one of claims 14 to 17, the kit according to claims 18 to 19, the method according to claims 20 to 21 or 22, wherein said tissue is selected from white and brown adipose tissue, liver tissue, pancreas tissue, bowel tissue, muscular tissue, stomach tissue, kidney tissue, hypothalamus tissue.

24. The binding molecule according to any one of claims 14 to 17 or 23, the kit according to claims 18 to 19 or 23, the method according to claims 20 to 21 or 22 to 23, wherein said binding molecule is a monoclonal or polyclonal antibody.

25. The binding molecule according to any one of claims 14 to 17 or 23 to 24, the kit according to claims 18 to 19 or 23 to 24, the method according to claim 20 to 21, 22 to 24, wherein said monoclonal antibody is a chimeric, humanized, or human antibody or antigen-binding fragment thereof.

REFERENCES

1. Vlassov A V, Magdaleno S, Setterquist R, Conrad R. Exosomes: current knowledge of their composition, biological functions, and diagnostic and therapeutic potentials. Biochim Biophys Acta 1820, 940-948 (2012).
2. Valadi H, Ekstrom K, Bossios A, Sjostrand M, Lee J J, Lotvall J O. Exosome-mediated transfer of mRNAs and microRNAs is a novel mechanism of genetic exchange between cells. Nat Cell Biol 9, 654-659 (2007).
3. Thery C, Ostrowski M, Segura E. Membrane vesicles as conveyors of immune responses. Nat Rev Immunol 9, 581-593 (2009).
4. Zhang H G, Grizzle W E. Exosomes: a novel pathway of local and distant intercellular communication that facilitates the growth and metastasis of neoplastic lesions. Am J Pathol 184, 28-41 (2014).
5. Raposo G, Stoorvogel W. Extracellular vesicles: exosomes, microvesicles, and friends. J Cell Biol 200, 373-383 (2013).
6. Hoshino A, et al. Tumour exosome integrins determine organotropic metastasis. Nature 527, 329-335 (2015).
7. Peinado H, et al. Melanoma exosomes educate bone marrow progenitor cells toward a pro-metastatic phenotype through MET. Nat Med 18, 883-891 (2012).
8. Rahman M J, Regn D, Bashratyan R, Dai Y D. Exosomes released by islet-derived mesenchymal stem cells trigger autoimmune responses in NOD mice. Diabetes 63, 1008-1020 (2014).
9. Robbins P D, Morelli A E. Regulation of immune responses by extracellular vesicles. Nat Rev Immunol 14, 195-208 (2014).
10. Coleman B M, Hill A F. Extracellular vesicles—Their role in the packaging and spread of misfolded proteins associated with neurodegenerative diseases. Semin Cell Dev Biol 40, 89-96 (2015).
11. Fasshauer M, Bluher M. Adipokines in health and disease. Trends Pharmacol Sci 36, 461-470 (2015).
12. Kloting N, Bluher M. Adipocyte dysfunction, inflammation and metabolic syndrome. Rev Endocr Metab Disord 15, 277-287 (2014).
13. Khandekar M J, Cohen P, Spiegelman B M. Molecular mechanisms of cancer development in obesity. Nat Rev Cancer 11, 886-895 (2011).
14. Bluher M, et al. Two patterns of adipokine and other biomarker dynamics in a long-term weight loss intervention. Diabetes Care 35, 342-349 (2012).
15. Deng Y, Scherer P E. Adipokines as novel biomarkers and regulators of the metabolic syndrome. Ann N Y Acad Sci 1212, E1-E19 (2010).
16. Thery C, Amigorena S, Raposo G, Clayton A. Isolation and characterization of exosomes from cell culture supernatants and biological fluids. Curr Protoc Cell Biol Chapter 3, Unit 3 22 (2006).
17. Ferrante S C, et al. Adipocyte-derived exosomal miR-NAs: a novel mechanism for obesity-related disease. Pediatr Res 77, 447-454 (2015).
18. Koeck E S, et al. Adipocyte exosomes induce transforming growth factor beta pathway dysregulation in hepatocytes: a novel paradigm for obesity-related liver disease. J Surg Res 192, 268-275 (2014).
19. Deng Z B, et al. Adipose tissue exosome-like vesicles mediate activation of macrophage-induced insulin resistance. Diabetes 58, 2498-2505 (2009).
20. Muller G, Jung C, Straub J, Wied S, Kramer W. Induced release of membrane vesicles from rat adipocytes containing glycosylphosphatidylinositol-anchored microdomain and lipid droplet signalling proteins. Cell Signal 21, 324-338 (2009).
21. Kanneganti T D, Dixit V D. Immunological complications of obesity. Nat Immunol 13, 707-712 (2012).
22. de Gassart A, Geminard C, Fevrier B, Raposo G, Vidal M. Lipid raft-associated protein sorting in exosomes. Blood 102, 4336-4344 (2003).
23. Ratajczak J, et al. Embryonic stem cell-derived microvesicles reprogram hematopoietic progenitors: evidence for horizontal transfer of mRNA and protein delivery. Leukemia 20, 847-856 (2006).
24. Ebert M S, Sharp P A. Roles for microRNAs in conferring robustness to biological processes. Cell 149, 515-524 (2012).
25. Ceppo F, Berthou F, Jager J, Dumas K, Cormont M, Tanti J F. Implication of the Tpl2 kinase in inflammatory changes and insulin resistance induced by the interaction between adipocytes and macrophages. Endocrinology 155, 951-964 (2014).
26. Perfield J W, 2nd, et al. Tumor progression locus 2 (TPL2) regulates obesity-associated inflammation and insulin resistance. Diabetes 60, 1168-1176 (2011).
27. Arkan M C, et al. IKK-beta links inflammation to obesity-induced insulin resistance. Nat Med 11, 191-198 (2005).
28. Lehr S, Hartwig S, Sell H. Adipokines: a treasure trove for the discovery of biomarkers for metabolic disorders. Proteomics Clin Appl 6, 91-101 (2012).
29. Bobrie A, Colombo M, Raposo G, Thery C. Exosome secretion: molecular mechanisms and roles in immune responses. Traffic 12, 1659-1668 (2011).
30. Muller G, Jung C, Straub J, Wied S, Kramer W. Induced release of membrane vesicles from rat adipocytes containing glycosylphosphatidylinositol-anchored microdomain and lipid droplet signalling proteins. Cell Signal 21, 324-338 (2009).
31. Muller G, Jung C, Wied S, Biemer-Daub G. Induced translocation of glycosylphosphatidylinositol-anchored proteins from lipid droplets to adiposomes in rat adipocytes. Br J Pharmacol 158, 749-770 (2009).
32. Weisberg S P, McCann D, Desai M, Rosenbaum M, Leibel R L, Ferrante A W, Jr. Obesity is associated with macrophage accumulation in adipose tissue. J Clin Invest 112, 1796-1808 (2003).
33. Sun D, et al. A novel nanoparticle drug delivery system: the anti-inflammatory activity of curcumin is enhanced when encapsulated in exosomes. Mol Ther 18, 1606-1614 (2010).
34. Takahashi Y, et al. Visualization and in vivo tracking of the exosomes of murine melanoma B16-BL6 cells in mice after intravenous injection. J Biotechnol 165, 77-84 (2013).
35. Ouchi N, Parker J L, Lugus J J, Walsh K. Adipokines in inflammation and metabolic disease. Nat Rev Immunol 11, 85-97 (2011).
36. Dumitru C D, et al. TNF-alpha induction by LPS is regulated posttranscriptionally via a Tpl2/ERK-dependent pathway. Cell 103, 1071-1083 (2000).
37. Partecke L I, et al. A syngeneic orthotopic murine model of pancreatic adenocarcinoma in the C57/BL6 mouse using the Panc02 and 6606PDA cell lines. Eur Surg Res 47, 98-107 (2011).
38. Wisniewski J R, Zougman A, Nagaraj N, Mann M. Universal sample preparation method for proteome analysis. Nat Methods 6, 359-362 (2009).

39. Grosche A, et al. The proteome of native adult Muller glial cells from murine retina. Mol Cell Proteomics, (2015).
40. Hauck S M, et al. Deciphering membrane-associated molecular processes in target tissue of autoimmune uveitis by label-free quantitative mass spectrometry. Mol Cell Proteomics 9, 2292-2305 (2010).
41. Merl J, Ueffing M, Hauck S M, von Toerne C. Direct comparison of MS-based label-free and SILAC quantitative proteome profiling strategies in primary retinal Muller cells. Proteomics 12, 1902-1911 (2012).
42. Barapatre N, et al. Quantitative detection of drug dose and spatial distribution in the lung revealed by Cryoslicing Imaging. J Pharm Biomed Anal 102, 129-136 (2015).
43. Pfaffl M W. A new mathematical model for relative quantification in real-time RT-PCR. Nucleic Acids Res 29, e45 (2001).
44. Dean C B, Nielsen J D. Generalized linear mixed models: a review and some extensions. Lifetime Data Anal 13, 497-512 (2007).
45. Rainer J, Sanchez-Cabo F, Stocker G, Sturn A, Trajanoski Z. CARMAweb: comprehensive R- and bioconductor-based web service for microarray data analysis. Nucleic Acids Res 34, W498-503 (2006).
46. Tang Y F, Zhang Y, Li XY, Li C, Tian W, Liu L. Expression of miR-31, miR-125b-5p, and miR-326 in the adipogenic differentiation process of adipose-derived stem cells. OMICS 13, 331-336 (2009).
47. Mi L, et al. MicroRNA-139-5p Suppresses 3T3-L1 Preadipocyte Differentiation Through Notch and IRS1/PI3K/Akt Insulin Signaling Pathways. J Cell Biochem 116, 1195-1204 (2015).
48. Wei Y, et al. The microRNA-342-5p fosters inflammatory macrophage activation through an Aktl- and microRNA-155-dependent pathway during atherosclerosis. Circulation 127, 1609-1619 (2013).
49. Wang L, et al. Obesity-Associated MiR-342-3p Promotes Adipogenesis of Mesenchymal Stem Cells by Suppressing CtBP2 and Releasing C/EBPalpha from CtBP2 Binding. Cell Physiol Biochem 35, 2285-2298 (2015).
50. Chartoumpekis D V, et al. Differential expression of microRNAs in adipose tissue after long-term high-fat diet-induced obesity in mice. PLoS One 7, e34872 (2012).
51. Oger F, et al. Cell-specific dysregulation of microRNA expression in obese white adipose tissue. J Clin Endocrinol Metab 99, 2821-2833 (2014).
52. Zhu L, et al. MiR-335, an adipogenesis-related microRNA, is involved in adipose tissue inflammation. Cell Biochem Biophys 68, 283-290 (2014).
53. Xue Y, et al. MicroRNA-19b/221/222 induces endothelial cell dysfunction via suppression of PGC-1alpha in the progression of atherosclerosis. Atherosclerosis 241, 671-681 (2015).
54. Cazanave S C, et al. A role for miR-296 in the regulation of lipoapoptosis by targeting PUMA. J Lipid Res 52, 1517-1525 (2011).
55. Pescador N, Perez-Barba M, Ibarra J M, Corbaton A, Martinez-Larrad M T, Serrano-Rios M. Serum circulating microRNA profiling for identification of potential type 2 diabetes and obesity biomarkers. PLoS One 8, e77251 (2013).
56. Yuan Z, Luo G, Li X, Chen J, Wu J, Peng Y. PPARgamma inhibits HMGB1 expression through upregulation of miR-142-3p in vitro and in vivo. Cell Signal 28, 158-164 (2015).
57. Fordham J B, Naqvi A R, Nares S. Regulation of miR-24, miR-30b, and miR-142-3p during macrophage and dendritic cell differentiation potentiates innate immunity. J Leukoc Biol 98, 195-207 (2015).
58. Ortega F J, et al. Targeting the circulating microRNA signature of obesity. Clin Chem 59, 781-792 (2013).
59. de Guia R M, et al. microRNA-379 couples glucocorticoid hormones to dysfunctional lipid homeostasis. EMBO J 34, 344-360 (2015).
60. Ahn J, Lee H, Jung C H, Jeon T I, Ha T Y. MicroRNA-146b promotes adipogenesis by suppressing the SIRT1-FOXO1 cascade. EMBO Mol Med 5, 1602-1612 (2013).
61. Shi C, et al. IL-6 and TNF-alpha induced obesity-related inflammatory response through transcriptional regulation of miR-146b. J Interferon Cytokine Res 34, 342-348 (2014).
62. Karbiener M, et al. microRNA miR-27b impairs human adipocyte differentiation and targets PPARgamma. Biochem Biophys Res Commun 390, 247-251 (2009).
63. Kong X, et al. Glucocorticoids transcriptionally regulate miR-27b expression promoting body fat accumulation via suppressing the browning of white adipose tissue. Diabetes 64, 393-404 (2015).
64. Ng R, et al. Inhibition of microRNA-24 expression in liver prevents hepatic lipid accumulation and hyperlipidemia. Hepatology 60, 554-564 (2014).
65. Lirun K, Sewe M, Yong W. A Pilot Study: The Effect of Roux-en-Y Gastric Bypass on the Serum MicroRNAs of the Type 2 Diabetes Patient. Obes Surg 25, 2386-2392 (2015).
66. Karbiener M, et al. MicroRNA-26 family is required for human adipogenesis and drives characteristics of brown adipocytes. Stem Cells 32, 1578-1590 (2014).
67. Fu X, et al. MicroRNA-26a regulates insulin sensitivity and metabolism of glucose and lipids. J Clin Invest 125, 2497-2509 (2015).
68. Zhang Q, et al. Acarbose reduces blood glucose by activating miR-10a-5p and miR-664 in diabetic rats. PLoS One 8, e79697 (2013).
69. Chen L, et al. MicroRNA-143 regulates adipogenesis by modulating the MAP2K5-ERK5 signaling. Sci Rep 4, 3819 (2014).
70. Esau C, et al. MicroRNA-143 regulates adipocyte differentiation. J Biol Chem 279, 52361-52365 (2004).
71. Kim Y J, Min T S, Seo K S, Kim S H. Expression of pref-1/dlk-1 is regulated by microRNA-143 in 3T3-L1 cells. Mol Biol Rep 42, 617-624 (2015).
72. Jordan S D, et al. Obesity-induced overexpression of miRNA-143 inhibits insulin-stimulated AKT activation and impairs glucose metabolism. Nat Cell Biol 13, 434-446 (2011).
73. Zheng Y, et al. miR-101a and miR-30b contribute to inflammatory cytokine-mediated beta-cell dysfunction. Lab Invest 95, 1387-1397 (2015).
74. Miyamoto Y, Mauer A S, Kumar S, Mott J L, Malhi H. Mmu-miR-615-3p regulates lipoapoptosis by inhibiting C/EBP homologous protein. PLoS One 9, e109637 (2014).
75. Li H, et al. MiRNA-181a regulates adipogenesis by targeting tumor necrosis factor-alpha (TNF-alpha) in the porcine model. PLoS One 8, e71568 (2013).
76. Hulsmans M, Sinnaeve P, Van der Schueren B, Mathieu C, Janssens S, Holvoet P. Decreased miR-181a expression in monocytes of obese patients is associated with the occurrence of metabolic syndrome and coronary artery disease. J Clin Endocrinol Metab 97, E1213-1218 (2012).

77. Zampetaki A, et al. Plasma microRNA profiling reveals loss of endothelial miR-126 and other microRNAs in type 2 diabetes. Circ Res 107, 810-817 (2010).
78. Lang H, et al. Characterization of miR-218/322-Stxbp1 pathway in the process of insulin secretion. J Mol Endocrinol 54, 65-73 (2015).
79. Shan Z, et al. Differentially expressed microRNAs at different stages of atherosclerosis in ApoE-deficient mice. Chin Med J (Engl) 126, 515-520 (2013).
80. Chou C F, et al. KSRP ablation enhances brown fat gene program in white adipose tissue through reduced miR-150 expression. Diabetes 63, 2949-2961 (2014).

The invention claimed is:

1. An antibody capable of specifically binding to a tissue-specific exosomal surface marker, wherein said antibody comprises
   a) VH and VL domain CDRs comprising the amino acid sequences SEQ ID Nos. 1 to 3 and 4 to 6;
   b) VH and VL domain CDRs comprising the amino acid sequences SEQ ID Nos. 7 to 9 and 10 to 12; or
   c) VH and VL domain CDRs comprising the amino acid sequences SEQ ID Nos. 13 to 15 and 16 to 18.

2. A kit comprising a reagent for detecting the presence of a tissue-specific exosomal surface marker and for isolating tissue-specific exosomes from a sample of a subject, wherein said reagent comprises an antibody capable of specifically binding to said tissue-specific exosomal surface marker, wherein said antibody comprises
   a) VH and VL domain CDRs comprising the amino acid sequences SEQ ID Nos. 1 to 3 and 4 to 6;
   b) VH and VL domain CDRs comprising the amino acid sequences SEQ ID Nos. 7 to 9 and 10 to 12; or
   c) VH and VL domain CDRs comprising the amino acid sequences SEQ ID Nos. 13 to 15 and 16 to 18.

3. A composition comprising the antibody of claim 1 and a biological sample comprising tissue-specific exosome.

4. The composition of claim 3, wherein the biological sample is selected from the group consisting of a blood sample, a plasma sample, a serum sample, lymph, saliva, bile, feces, breast milk, a urine sample, a cerebrospinal fluid sample, amniotic fluid, and an organ or tissue biopsy sample.

5. A method for isolating a tissue-specific exosome comprising obtaining the composition of claim 3, and isolating tissue-specific exosomes using the antibody.

6. The method of claim 5, further comprising a step of detecting the tissue-specific exosomes that are isolated using the antibody.

* * * * *

```
                       SEQUENCE LISTING

<160> NUMBER OF SEQ ID NOS: 66

<210> SEQ ID NO 1
<211> LENGTH: 7
<212> TYPE: PRT
<213> ORGANISM: Artificial sequence
<220> FEATURE:
<223> OTHER INFORMATION: CDR1 in the VH domain of antibody 23A11

<400> SEQUENCE: 1

Gly Phe Thr Phe Thr Asp Phe
1               5

<210> SEQ ID NO 2
<211> LENGTH: 8
<212> TYPE: PRT
<213> ORGANISM: Artificial sequence
<220> FEATURE:
<223> OTHER INFORMATION: CDR2 in the VH domain of antibody 23A11

<400> SEQUENCE: 2

Arg Asn Lys Ala Asn Gly Tyr Thr
1               5

<210> SEQ ID NO 3
<211> LENGTH: 13
<212> TYPE: PRT
<213> ORGANISM: Artificial sequence
<220> FEATURE:
<223> OTHER INFORMATION: CDR3 in the VH domain of antibody 23A11

<400> SEQUENCE: 3

Gly Gly Phe Asp Val Tyr Ser Gly Leu Leu Pro Asp Tyr
1               5                   10

<210> SEQ ID NO 4
<211> LENGTH: 17
<212> TYPE: PRT
<213> ORGANISM: Artificial sequence
<220> FEATURE:
<223> OTHER INFORMATION: CDR1 in the VL domain of antibody 23A11

<400> SEQUENCE: 4

Lys Ser Ser Gln Asn Leu Leu Tyr Arg Gly Asn Gln Lys Asn Tyr Leu
1               5                   10                  15

Ala

<210> SEQ ID NO 5
<211> LENGTH: 7
<212> TYPE: PRT
<213> ORGANISM: Artificial sequence
<220> FEATURE:
<223> OTHER INFORMATION: CDR2 in the VL domain of antibody 23A11

<400> SEQUENCE: 5

Trp Thr Ser Thr Arg Gln Pro
1               5

<210> SEQ ID NO 6
```

```
<211> LENGTH: 9
<212> TYPE: PRT
<213> ORGANISM: Artificial sequence
<220> FEATURE:
<223> OTHER INFORMATION: CDR3 in the VL domain of antibody 23A11

<400> SEQUENCE: 6

Gln Gln Tyr Tyr Gly Thr Pro Phe Thr
1               5

<210> SEQ ID NO 7
<211> LENGTH: 7
<212> TYPE: PRT
<213> ORGANISM: Artificial sequence
<220> FEATURE:
<223> OTHER INFORMATION: CDR1 in the VH domain of antibody 15G1

<400> SEQUENCE: 7

Gly Phe Asn Phe Asn Asp Tyr
1               5

<210> SEQ ID NO 8
<211> LENGTH: 8
<212> TYPE: PRT
<213> ORGANISM: Artificial sequence
<220> FEATURE:
<223> OTHER INFORMATION: CDR2 in the VH domain of antibody 15G1

<400> SEQUENCE: 8

Arg Asn Lys His Tyr Asn Tyr Ala
1               5

<210> SEQ ID NO 9
<211> LENGTH: 9
<212> TYPE: PRT
<213> ORGANISM: Artificial sequence
<220> FEATURE:
<223> OTHER INFORMATION: CDR3 in the VH domain of antibody 15G1

<400> SEQUENCE: 9

Ser Ser Tyr Leu Arg Tyr Phe Asp Phe
1               5

<210> SEQ ID NO 10
<211> LENGTH: 11
<212> TYPE: PRT
<213> ORGANISM: Artificial sequence
<220> FEATURE:
<223> OTHER INFORMATION: CDR1 in the VL domain of antibody 15G1

<400> SEQUENCE: 10

Gln Ala Ser Gln Asp Ile Gly Asn Trp Leu Ala
1               5                   10

<210> SEQ ID NO 11
<211> LENGTH: 7
<212> TYPE: PRT
<213> ORGANISM: Artificial sequence
<220> FEATURE:
<223> OTHER INFORMATION: CDR2 in the VL domain of antibody 15G1

<400> SEQUENCE: 11

Asp Ala Thr Thr Leu Ala Asp
1               5

<210> SEQ ID NO 12
<211> LENGTH: 9
```

```
<212> TYPE: PRT
<213> ORGANISM: Artificial sequence
<220> FEATURE:
<223> OTHER INFORMATION: CDR3 in the VL domain of antibody 15G1

<400> SEQUENCE: 12

Gln Gln Ala Ser Ser Ala Pro Trp Thr
 1               5

<210> SEQ ID NO 13
<211> LENGTH: 7
<212> TYPE: PRT
<213> ORGANISM: Artificial sequence
<220> FEATURE:
<223> OTHER INFORMATION: CDR1 in the VH domain of antibody 14H5

<400> SEQUENCE: 13

Gly Phe Thr Phe Thr Gly Tyr
 1               5

<210> SEQ ID NO 14
<211> LENGTH: 6
<212> TYPE: PRT
<213> ORGANISM: Artificial sequence
<220> FEATURE:
<223> OTHER INFORMATION: CDR2 in the VH domain of antibody 14H5

<400> SEQUENCE: 14

Asn Thr Gly Ser Gly Gly
 1               5

<210> SEQ ID NO 15
<211> LENGTH: 9
<212> TYPE: PRT
<213> ORGANISM: Artificial sequence
<220> FEATURE:
<223> OTHER INFORMATION: CDR3 in the VH domain of antibody 14H5

<400> SEQUENCE: 15

Thr Tyr Trp Arg Arg Tyr Phe Asp Tyr
 1               5

<210> SEQ ID NO 16
<211> LENGTH: 11
<212> TYPE: PRT
<213> ORGANISM: Artificial sequence
<220> FEATURE:
<223> OTHER INFORMATION: CDR1 in the VL domain of antibody 14H5

<400> SEQUENCE: 16

Gln Ala Ser Gln Asp Ile Gly Asn Trp Leu Ala
 1               5                  10

<210> SEQ ID NO 17
<211> LENGTH: 7
<212> TYPE: PRT
<213> ORGANISM: Artificial sequence
<220> FEATURE:
<223> OTHER INFORMATION: CDR2 in the VL domain of antibody 14H5

<400> SEQUENCE: 17

Gly Ala Thr Ser Leu Ala Asp
 1               5

<210> SEQ ID NO 18
<211> LENGTH: 9
<212> TYPE: PRT
```

-continued

<213> ORGANISM: Artificial sequence
<220> FEATURE:
<223> OTHER INFORMATION: CDR3 in the VL domain of antibody 14H5

<400> SEQUENCE: 18

Gln Gln Ala Ser Ser Ala Pro Leu Thr
1               5

<210> SEQ ID NO 19
<211> LENGTH: 143
<212> TYPE: PRT
<213> ORGANISM: Artificial sequence
<220> FEATURE:
<223> OTHER INFORMATION: Variable domain heavy chain 23A11

<400> SEQUENCE: 19

Met Lys Leu Trp Leu Asn Trp Ile Phe Leu Leu Thr Leu Leu Asn Gly
1               5                   10                  15

Ile Gln Cys Glu Val Lys Leu Leu Glu Ser Gly Gly Gly Leu Val Gln
                20                  25                  30

Pro Gly Gly Ser Met Arg Leu Ser Cys Ala Ala Ser Gly Phe Thr Phe
            35                  40                  45

Thr Asp Phe Tyr Met Asn Trp Ile Arg Gln Pro Ser Lys Ala Pro
    50                  55                  60

Glu Trp Leu Gly Phe Ile Arg Asn Lys Ala Asn Gly Tyr Thr Thr Glu
65                  70                  75                  80

Ser Asn Pro Ser Val Lys Gly Arg Phe Thr Ile Ser Arg Asp Asn Thr
                85                  90                  95

Gln Ser Met Leu Tyr Leu Gln Met Asn Thr Leu Arg Val Glu Asp Thr
                100                 105                 110

Ala Thr Tyr Tyr Cys Ala Arg Gly Gly Phe Asp Val Tyr Ser Gly Leu
            115                 120                 125

Leu Pro Asp Tyr Trp Gly Gln Gly Val Met Thr Val Ser Ser
        130                 135                 140

<210> SEQ ID NO 20
<211> LENGTH: 133
<212> TYPE: PRT
<213> ORGANISM: Artificial sequence
<220> FEATURE:
<223> OTHER INFORMATION: Variable domain light chain 23A11

<400> SEQUENCE: 20

Met Glu Ser Gln Thr Gln Val Leu Met Ser Leu Leu Leu Trp Ile Ser
1               5                   10                  15

Gly Thr Cys Gly Asp Ile Val Met Thr Gln Ser Pro Ser Ser Leu Ala
                20                  25                  30

Val Ser Ala Gly Glu Thr Val Thr Ile Asn Cys Lys Ser Ser Gln Asn
            35                  40                  45

Leu Leu Tyr Arg Gly Asn Gln Lys Asn Tyr Leu Ala Trp Tyr Gln Gln
        50                  55                  60

Lys Pro Gly Gln Ser Pro Lys Leu Leu Ile Phe Trp Thr Ser Thr Arg
65                  70                  75                  80

Gln Pro Gly Val Pro Asp Arg Phe Ile Gly Ser Gly Ser Gly Thr Asp
                85                  90                  95

Phe Thr Leu Thr Ile Ser Ser Val Gln Ala Glu Asp Leu Ala Ile Tyr
            100                 105                 110

Tyr Cys Gln Gln Tyr Tyr Gly Thr Pro Phe Thr Phe Gly Ser Gly Thr
        115                 120                 125

Lys Leu Glu Ile Arg
    130

<210> SEQ ID NO 21
<211> LENGTH: 139
<212> TYPE: PRT
<213> ORGANISM: Artificial sequence
<220> FEATURE:
<223> OTHER INFORMATION: Variable domain heavy chain 15G1

<400> SEQUENCE: 21

Met Lys Leu Trp Leu Ser Trp Ile Phe Leu Val Val Leu Phe Lys Gly
1               5                   10                  15

Val Arg Cys Glu Val Gln Ile Leu Glu Thr Gly Gly Gly Leu Val Lys
            20                  25                  30

Pro Gly Gly Ser Leu Arg Leu Ser Cys Ala Thr Ser Gly Phe Asn Phe
        35                  40                  45

Asn Asp Tyr Phe Met Asn Trp Val Arg Gln Ala Pro Gly Lys Gly Leu
    50                  55                  60

Glu Trp Val Ala Gln Ile Arg Asn Lys His Tyr Asn Tyr Ala Thr Tyr
65                  70                  75                  80

Tyr Gly Glu Ser Leu Glu Gly Arg Val Thr Ile Ser Arg Asp Asp Ser
                85                  90                  95

Lys Ser Asn Val Tyr Leu Gln Val Asn Ser Leu Arg Pro Glu Asp Thr
            100                 105                 110

Ala Ile Tyr Tyr Cys Ser Arg Ser Ser Tyr Leu Arg Tyr Phe Asp Phe
        115                 120                 125

Trp Gly Pro Gly Thr Met Val Thr Val Ser Ser
    130                 135

<210> SEQ ID NO 22
<211> LENGTH: 128
<212> TYPE: PRT
<213> ORGANISM: Artificial sequence
<220> FEATURE:
<223> OTHER INFORMATION: Variable domain light chain 15G1

<400> SEQUENCE: 22

Met Asn Val Pro Thr Gln Leu Leu Gly Leu Leu Ile Leu Trp Leu Thr
1               5                   10                  15

Gly Gly Lys Cys Asp Ile Gln Met Thr Gln Ser Pro Ala Ser Leu Ser
            20                  25                  30

Ala Ser Leu Glu Glu Ile Val Thr Ile Thr Cys Gln Ala Ser Gln Asp
        35                  40                  45

Ile Gly Asn Trp Leu Ala Trp Tyr Gln Gln Lys Pro Gly Lys Ser Pro
    50                  55                  60

Gln Leu Leu Ile Tyr Asp Ala Thr Thr Leu Ala Asp Gly Val Pro Ser
65                  70                  75                  80

Arg Phe Ser Gly Ser Arg Ser Gly Thr Gln Phe Ser Leu Lys Ile Ser
                85                  90                  95

Arg Leu Gln Val Glu Asp Ile Gly Ile Tyr Tyr Cys Gln Gln Ala Ser
            100                 105                 110

Ser Ala Pro Trp Thr Phe Gly Gly Gly Thr Asn Leu Glu Leu Lys Arg
        115                 120                 125

<210> SEQ ID NO 23
<211> LENGTH: 137
<212> TYPE: PRT

<213> ORGANISM: Artificial Sequence
<220> FEATURE:
<223> OTHER INFORMATION: Variable domain heavy chain 14H5

<400> SEQUENCE: 23

```
Met Glu Trp Asn Trp Val Phe Leu Phe Leu Ser Val Thr Ala Glu
1               5                   10                  15

Val His Ser Gln Val Gln Leu Gln Gln Ser Gly Ala Glu Leu Ala Lys
            20                  25                  30

Pro Gly Ser Ser Val Lys Ile Ser Cys Lys Ala Ser Gly Phe Thr Phe
        35                  40                  45

Thr Gly Tyr Tyr Ile Ser Trp Ile Lys Gln Thr Thr Gly Gln Gly Leu
    50                  55                  60

Asp Tyr Ile Gly Tyr Ile Asn Thr Gly Ser Gly Gly Thr Asn Tyr Asn
65                  70                  75                  80

Glu Lys Phe Lys Gly Lys Ala Thr Leu Thr Val Asp Lys Ser Ser Ser
                85                  90                  95

Thr Ala Phe Met Gln Leu Ser Ser Leu Thr Pro Asp Asp Ser Ala Val
            100                 105                 110

Tyr Tyr Cys Ala Arg Thr Tyr Trp Arg Arg Tyr Phe Asp Tyr Trp Gly
        115                 120                 125

Gln Gly Val Met Val Thr Val Ser Ser
    130                 135
```

<210> SEQ ID NO 24
<211> LENGTH: 128
<212> TYPE: PRT
<213> ORGANISM: Artificial sequence
<220> FEATURE:
<223> OTHER INFORMATION: Variable domain light chain 14H5

<400> SEQUENCE: 24

```
Met Asn Val Pro Thr Gln Leu Leu Gly Leu Leu Ile Leu Trp Leu Thr
1               5                   10                  15

Gly Gly Lys Cys Asp Ile Gln Met Thr Gln Ser Pro Ala Ser Leu Ser
            20                  25                  30

Val Ser Leu Glu Lys Ile Val Thr Ile Thr Cys Gln Ala Ser Gln Asp
        35                  40                  45

Ile Gly Asn Trp Leu Ala Trp Tyr Gln Gln Lys Pro Gly Lys Ser Pro
    50                  55                  60

Gln Leu Leu Ile Tyr Gly Ala Thr Ser Leu Ala Asp Gly Val Pro Ser
65                  70                  75                  80

Arg Phe Ser Gly Ser Arg Ser Gly Thr Gln Tyr Ser Leu Lys Ile Ser
                85                  90                  95

Arg Leu Gln Val Glu Asp Ile Gly Ile Tyr Tyr Cys Gln Gln Ala Ser
            100                 105                 110

Ser Ala Pro Leu Thr Phe Gly Ser Gly Thr Lys Leu Glu Ile Lys Arg
        115                 120                 125
```

<210> SEQ ID NO 25
<211> LENGTH: 25
<212> TYPE: PRT
<213> ORGANISM: Artificial sequence
<220> FEATURE:
<223> OTHER INFORMATION: Framework region 1 variable domain heavy chain 23A11

<400> SEQUENCE: 25

```
Glu Val Lys Leu Leu Glu Ser Gly Gly Gly Leu Val Gln Pro Gly Gly
```

```
1               5                   10                  15
Ser Met Arg Leu Ser Cys Ala Ala Ser
            20                  25

<210> SEQ ID NO 26
<211> LENGTH: 19
<212> TYPE: PRT
<213> ORGANISM: Artificial sequence
<220> FEATURE:
<223> OTHER INFORMATION: Framework region 2 variable domain heavy chain
      23A11

<400> SEQUENCE: 26

Tyr Met Asn Trp Ile Arg Gln Pro Ser Gly Lys Ala Pro Glu Trp Leu
1               5                   10                  15

Gly Phe Ile

<210> SEQ ID NO 27
<211> LENGTH: 41
<212> TYPE: PRT
<213> ORGANISM: Artificial Sequence
<220> FEATURE:
<223> OTHER INFORMATION: Framework region 3 variable domain heavy chain
      23A11

<400> SEQUENCE: 27

Thr Glu Ser Asn Pro Ser Val Lys Gly Arg Phe Thr Ile Ser Arg Asp
1               5                   10                  15

Asn Thr Gln Ser Met Leu Tyr Leu Gln Met Asn Thr Leu Arg Val Glu
            20                  25                  30

Asp Thr Ala Thr Tyr Tyr Cys Ala Arg
        35                  40

<210> SEQ ID NO 28
<211> LENGTH: 11
<212> TYPE: PRT
<213> ORGANISM: Artificial sequence
<220> FEATURE:
<223> OTHER INFORMATION: Framework region 4 variable domain heavy chain
      23A11

<400> SEQUENCE: 28

Trp Gly Gln Gly Val Met Val Thr Val Ser Ser
1               5                   10

<210> SEQ ID NO 29
<211> LENGTH: 23
<212> TYPE: PRT
<213> ORGANISM: Artificial sequence
<220> FEATURE:
<223> OTHER INFORMATION: Framework region 1 variable domain light chain
      23A11

<400> SEQUENCE: 29

Asp Ile Val Met Thr Gln Ser Pro Ser Ser Leu Ala Val Ser Ala Gly
1               5                   10                  15

Glu Thr Val Thr Ile Asn Cys
            20

<210> SEQ ID NO 30
<211> LENGTH: 15
<212> TYPE: PRT
<213> ORGANISM: Artificial sequence
<220> FEATURE:
<223> OTHER INFORMATION: Framework region 2 variable domain light chain
```

23A11

<400> SEQUENCE: 30

Trp Tyr Gln Gln Lys Pro Gly Gln Ser Pro Lys Leu Leu Ile Phe
1               5                   10                  15

<210> SEQ ID NO 31
<211> LENGTH: 32
<212> TYPE: PRT
<213> ORGANISM: Artificial sequence
<220> FEATURE:
<223> OTHER INFORMATION: Framework region 3 variable domain light chain
      23A11

<400> SEQUENCE: 31

Gly Val Pro Asp Arg Phe Ile Gly Ser Gly Ser Gly Thr Asp Phe Thr
1               5                   10                  15

Leu Thr Ile Ser Ser Val Gln Ala Glu Asp Leu Ala Ile Tyr Tyr Cys
            20                  25                  30

<210> SEQ ID NO 32
<211> LENGTH: 10
<212> TYPE: PRT
<213> ORGANISM: Artificial sequence
<220> FEATURE:
<223> OTHER INFORMATION: Framework region 4 variable domain light chain
      23A11

<400> SEQUENCE: 32

Phe Gly Ser Gly Thr Lys Leu Glu Ile Arg
1               5                   10

<210> SEQ ID NO 33
<211> LENGTH: 25
<212> TYPE: PRT
<213> ORGANISM: Artificial sequence
<220> FEATURE:
<223> OTHER INFORMATION: Framework region 1 variable domain heavy chain
      15G1

<400> SEQUENCE: 33

Glu Val Gln Ile Leu Glu Thr Gly Gly Gly Leu Val Lys Pro Gly Gly
1               5                   10                  15

Ser Leu Arg Leu Ser Cys Ala Thr Ser
            20                  25

<210> SEQ ID NO 34
<211> LENGTH: 19
<212> TYPE: PRT
<213> ORGANISM: Artificial sequence
<220> FEATURE:
<223> OTHER INFORMATION: Framework region 2 variable domain heavy chain
      15G1

<400> SEQUENCE: 34

Phe Met Asn Trp Val Arg Gln Ala Pro Gly Lys Gly Leu Glu Trp Val
1               5                   10                  15

Ala Gln Ile

<210> SEQ ID NO 35
<211> LENGTH: 41
<212> TYPE: PRT
<213> ORGANISM: Artificial sequence
<220> FEATURE:
<223> OTHER INFORMATION: Framework region 3 variable domain heavy chain
      15G1

<400> SEQUENCE: 35

Thr Tyr Tyr Gly Glu Ser Leu Glu Gly Arg Val Thr Ile Ser Arg Asp
1               5                   10                  15

Asp Ser Lys Ser Asn Val Tyr Leu Gln Val Asn Ser Leu Arg Pro Glu
            20                  25                  30

Asp Thr Ala Ile Tyr Tyr Cys Ser Arg
            35                  40

<210> SEQ ID NO 36
<211> LENGTH: 11
<212> TYPE: PRT
<213> ORGANISM: Artificial sequence
<220> FEATURE:
<223> OTHER INFORMATION: Framework region 4 variable domain heavy chain
      15G1

<400> SEQUENCE: 36

Trp Gly Pro Gly Thr Met Val Thr Val Ser Ser
1               5                   10

<210> SEQ ID NO 37
<211> LENGTH: 23
<212> TYPE: PRT
<213> ORGANISM: Artificial sequence
<220> FEATURE:
<223> OTHER INFORMATION: Framework region 1 variable domain light chain
      15G1

<400> SEQUENCE: 37

Asp Ile Gln Met Thr Gln Ser Pro Ala Ser Leu Ser Ala Ser Leu Glu
1               5                   10                  15

Glu Ile Val Thr Ile Thr Cys
            20

<210> SEQ ID NO 38
<211> LENGTH: 15
<212> TYPE: PRT
<213> ORGANISM: Artificial sequence
<220> FEATURE:
<223> OTHER INFORMATION: Framework region 2 variable domain light chain
      15G1

<400> SEQUENCE: 38

Trp Tyr Gln Gln Lys Pro Gly Lys Ser Pro Gln Leu Leu Ile Tyr
1               5                   10                  15

<210> SEQ ID NO 39
<211> LENGTH: 32
<212> TYPE: PRT
<213> ORGANISM: Artificial sequence
<220> FEATURE:
<223> OTHER INFORMATION: Framework region 3 variable domain light chain
      15G1

<400> SEQUENCE: 39

Gly Val Pro Ser Arg Phe Ser Gly Ser Arg Ser Gly Thr Gln Phe Ser
1               5                   10                  15

Leu Lys Ile Ser Arg Leu Gln Val Glu Asp Ile Gly Ile Tyr Tyr Cys
            20                  25                  30

<210> SEQ ID NO 40
<211> LENGTH: 10
<212> TYPE: PRT
<213> ORGANISM: Artificial sequence

```
<220> FEATURE:
<223> OTHER INFORMATION: Framework region 4 variable domain light chain
      15G1

<400> SEQUENCE: 40

Phe Gly Gly Gly Thr Asn Leu Glu Leu Lys
1               5                   10

<210> SEQ ID NO 41
<211> LENGTH: 25
<212> TYPE: PRT
<213> ORGANISM: Artificial sequence
<220> FEATURE:
<223> OTHER INFORMATION: Framework region 1 variable domain heavy chain
      14H5

<400> SEQUENCE: 41

Gln Val Gln Leu Gln Gln Ser Gly Ala Glu Leu Ala Lys Pro Gly Ser
1               5                   10                  15

Ser Val Lys Ile Ser Cys Lys Ala Ser
            20                  25

<210> SEQ ID NO 42
<211> LENGTH: 19
<212> TYPE: PRT
<213> ORGANISM: Artificial sequence
<220> FEATURE:
<223> OTHER INFORMATION: Framework region 2 variable domain heavy chain
      14H5

<400> SEQUENCE: 42

Tyr Ile Ser Trp Ile Lys Gln Thr Thr Gly Gln Gly Leu Asp Tyr Ile
1               5                   10                  15

Gly Tyr Ile

<210> SEQ ID NO 43
<211> LENGTH: 41
<212> TYPE: PRT
<213> ORGANISM: Artificial sequence
<220> FEATURE:
<223> OTHER INFORMATION: Framework region 3 variable domain heavy chain
      14H5

<400> SEQUENCE: 43

Thr Asn Tyr Asn Glu Lys Phe Lys Gly Lys Ala Thr Leu Thr Val Asp
1               5                   10                  15

Lys Ser Ser Ser Thr Ala Phe Met Gln Leu Ser Ser Leu Thr Pro Asp
            20                  25                  30

Asp Ser Ala Val Tyr Tyr Cys Ala Arg
        35                  40

<210> SEQ ID NO 44
<211> LENGTH: 11
<212> TYPE: PRT
<213> ORGANISM: Artificial sequence
<220> FEATURE:
<223> OTHER INFORMATION: Framework region 4 variable domain heavy chain
      14H5

<400> SEQUENCE: 44

Trp Gly Gln Gly Val Met Val Thr Val Ser Ser
1               5                   10

<210> SEQ ID NO 45
<211> LENGTH: 23
```

```
<212> TYPE: PRT
<213> ORGANISM: Artificial sequence
<220> FEATURE:
<223> OTHER INFORMATION: Framework region 1 variable domain light chain
      14H5

<400> SEQUENCE: 45

Asp Ile Gln Met Thr Gln Ser Pro Ala Ser Leu Ser Val Ser Leu Glu
1               5                   10                  15

Lys Ile Val Thr Ile Thr Cys
            20

<210> SEQ ID NO 46
<211> LENGTH: 15
<212> TYPE: PRT
<213> ORGANISM: Artificial sequence
<220> FEATURE:
<223> OTHER INFORMATION: Framework region 2 variable domain light chain
      14H5

<400> SEQUENCE: 46

Trp Tyr Gln Gln Lys Pro Gly Lys Ser Pro Gln Leu Leu Ile Tyr
1               5                   10                  15

<210> SEQ ID NO 47
<211> LENGTH: 32
<212> TYPE: PRT
<213> ORGANISM: Artificial sequence
<220> FEATURE:
<223> OTHER INFORMATION: Framework region 3 variable domain light chain
      14H5

<400> SEQUENCE: 47

Gly Val Pro Ser Arg Phe Ser Gly Ser Arg Ser Gly Thr Gln Tyr Ser
1               5                   10                  15

Leu Lys Ile Ser Arg Leu Gln Val Glu Asp Ile Gly Ile Tyr Tyr Cys
            20                  25                  30

<210> SEQ ID NO 48
<211> LENGTH: 12
<212> TYPE: PRT
<213> ORGANISM: Artificial sequence
<220> FEATURE:
<223> OTHER INFORMATION: Framework region 4 variable domain light chain
      14H5

<400> SEQUENCE: 48

Phe Gly Ser Gly Thr Lys Leu Glu Ile Lys Arg Ala
1               5                   10

<210> SEQ ID NO 49
<211> LENGTH: 22
<212> TYPE: DNA
<213> ORGANISM: artificial
<220> FEATURE:
<223> OTHER INFORMATION: Primer

<400> SEQUENCE: 49
agattcggga tatgctgttg gc                                              22

<210> SEQ ID NO 50
<211> LENGTH: 21
<212> TYPE: DNA
<213> ORGANISM: artificial
<220> FEATURE:
<223> OTHER INFORMATION: Primer
```

```
<400> SEQUENCE: 50
tcgggtccta gaccagtgtt c                                              21

<210> SEQ ID NO 51
<211> LENGTH: 22
<212> TYPE: DNA
<213> ORGANISM: artificial
<220> FEATURE:
<223> OTHER INFORMATION: Primer

<400> SEQUENCE: 51
ctccaagcca aagtccttag ag                                             22

<210> SEQ ID NO 52
<211> LENGTH: 22
<212> TYPE: DNA
<213> ORGANISM: artificial
<220> FEATURE:
<223> OTHER INFORMATION: Primer

<400> SEQUENCE: 52
aggagctgtc attagggaca tc                                             22

<210> SEQ ID NO 53
<211> LENGTH: 21
<212> TYPE: DNA
<213> ORGANISM: artificial
<220> FEATURE:
<223> OTHER INFORMATION: Primer

<400> SEQUENCE: 53
agagaccagg tgaagtcaga g                                              21

<210> SEQ ID NO 54
<211> LENGTH: 23
<212> TYPE: DNA
<213> ORGANISM: artificial
<220> FEATURE:
<223> OTHER INFORMATION: Primer

<400> SEQUENCE: 54
agtctgtgta gttagaagct cca                                            23

<210> SEQ ID NO 55
<211> LENGTH: 20
<212> TYPE: DNA
<213> ORGANISM: artificial
<220> FEATURE:
<223> OTHER INFORMATION: Primer

<400> SEQUENCE: 55
ctctggagag cacagtggag                                                20

<210> SEQ ID NO 56
<211> LENGTH: 19
<212> TYPE: DNA
<213> ORGANISM: artificial
<220> FEATURE:
<223> OTHER INFORMATION: Primer

<400> SEQUENCE: 56
acttccgagc cgttgttct                                                 19

<210> SEQ ID NO 57
<211> LENGTH: 19
```

```
<212> TYPE: DNA
<213> ORGANISM: artificial
<220> FEATURE:
<223> OTHER INFORMATION: Primer

<400> SEQUENCE: 57
atggtcaacc ccaccgtgt                                                  19

<210> SEQ ID NO 58
<211> LENGTH: 25
<212> TYPE: DNA
<213> ORGANISM: artificial
<220> FEATURE:
<223> OTHER INFORMATION: Primer

<400> SEQUENCE: 58
tttctgctgt ctttggaact ttgtc                                           25

<210> SEQ ID NO 59
<211> LENGTH: 21
<212> TYPE: DNA
<213> ORGANISM: artificial
<220> FEATURE:
<223> OTHER INFORMATION: Primer

<400> SEQUENCE: 59
ccctccactg taacgaagac t                                               21

<210> SEQ ID NO 60
<211> LENGTH: 20
<212> TYPE: DNA
<213> ORGANISM: artificial
<220> FEATURE:
<223> OTHER INFORMATION: Primer

<400> SEQUENCE: 60
cagtggtcca gtcaacgagt                                                 20

<210> SEQ ID NO 61
<211> LENGTH: 20
<212> TYPE: DNA
<213> ORGANISM: artificial
<220> FEATURE:
<223> OTHER INFORMATION: Primer

<400> SEQUENCE: 61
ccccgctact actccatcag                                                 20

<210> SEQ ID NO 62
<211> LENGTH: 20
<212> TYPE: DNA
<213> ORGANISM: artificial
<220> FEATURE:
<223> OTHER INFORMATION: Primer

<400> SEQUENCE: 62
ccactgacac ttcgcacaaa                                                 20

<210> SEQ ID NO 63
<211> LENGTH: 22
<212> TYPE: DNA
<213> ORGANISM: artificial
<220> FEATURE:
<223> OTHER INFORMATION: Primer

<400> SEQUENCE: 63
```

-continued

```
agccgtgacc actgacaacg ag                                            22

<210> SEQ ID NO 64
<211> LENGTH: 23
<212> TYPE: DNA
<213> ORGANISM: artificial
<220> FEATURE:
<223> OTHER INFORMATION: Primer

<400> SEQUENCE: 64
gctgcatggt tctgagtgct aag                                           23

<210> SEQ ID NO 65
<211> LENGTH: 20
<212> TYPE: DNA
<213> ORGANISM: artificial
<220> FEATURE:
<223> OTHER INFORMATION: Primer

<400> SEQUENCE: 65
ggcctctacg actcagtcca                                               20

<210> SEQ ID NO 66
<211> LENGTH: 20
<212> TYPE: DNA
<213> ORGANISM: artificial
<220> FEATURE:
<223> OTHER INFORMATION: Primer

<400> SEQUENCE: 66
taagccggct gagatcttgt                                               20
```